(12) United States Patent
Corbera-Arjona et al.

(10) Patent No.: US 8,492,563 B2
(45) Date of Patent: Jul. 23, 2013

(54) 4,5,6,7-TETRAHYDROBENZO[B]THIOPHENE DERIVATIVES AND THEIR USE AS SIGMA RECEPTOR LIGANDS

(75) Inventors: Jordi Corbera-Arjona, Barcelona (ES);
Daniel Martinez-Olmo, Barcelona (ES);
David Vano-Domenech, Barcelona (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 13/483,170

(22) Filed: May 30, 2012

(65) Prior Publication Data
US 2012/0238567 A1   Sep. 20, 2012

Related U.S. Application Data

(62) Division of application No. 12/281,317, filed as application No. PCT/EP2007/001824 on Mar. 2, 2007, now Pat. No. 8,227,625.

(30) Foreign Application Priority Data

Mar. 2, 2006   (EP) .................................... 06004286

(51) Int. Cl.
*C07D 333/00*   (2006.01)
*C07D 409/00*   (2006.01)
*A61K 31/397*   (2006.01)

(52) U.S. Cl.
USPC ........................... 549/49; 546/202; 514/233.5

(58) Field of Classification Search
USPC ........................... 549/49; 546/202; 514/233.5
See application file for complete search history.

(56) References Cited

FOREIGN PATENT DOCUMENTS

WO   94/00441 A1   1/1994
WO   01/32655 A2   5/2001

OTHER PUBLICATIONS

Jacques H. Poupaert Chemistry and Molecular Aspects of Drug Design and Action (2008), 93-100.*
Maurice et al. Pharmacology & Therapeutics 124 (2009) 195-206.*
Wolff, Burger's medicinal Chemistry and Drug Discovery, vol. 1, Principles and Practice, John Wiley & sons, New York, 1997.*
West, Solid State Chemistry and Its Applications, John Wiley & Sons, 1984.*
International Search Report issued in PCT/EP2007/001824, mailed Jul. 18, 2007.
CAPLUS STN Database Accession No. 1992:128652 (1991).
Berardi et al., "Novel Potent $\sigma_1$ Ligands: N-[ω-(Tetralin-1-yl)alkyl]piperidine Derivatives," *Journal of Medicinal Chemistry*, 39(21):4255-4260 (1996).
Berardi et al., "A Multireceptorial Binding Reinvestigation on an Extended class of σ Ligands: N-[ω-(Indan-1-yl and Tetralin-1-yl)alkyl] Derivatives of 3,3-Dimethylpiperdine Reveal High Affinities Towards $\sigma_1$ and EBP Sites," *Bioorganic & Medicinal Chemistry*, 9(5):1325-1335 (2001).
Berardi et al., "4-(Tetralin-1-yl)- and 4-(Naphthalen-1-yl)alkyl Derivatives of 1-Cyclohexylpiperazine as σ Receptor Ligands with Agonist $\sigma_2$ Activity," *Journal of Medicinal Chemistry*, 47(9):2308-2317 (2004).
West, Solid State Chemistry and Its Applications, John Wiley & Sons (1984).

* cited by examiner

*Primary Examiner* — Nizal Chandrakumar
(74) *Attorney, Agent, or Firm* — Heslin Rothenberg Farley & Mesiti P.C.; Andrew K. Gonsalves

(57) ABSTRACT

The present invention relates to compounds having pharmacological activity towards the sigma (σ) receptor, and more particularly to some 4, 5, 6, 7 tetrahydrobenzo[b]thiophene derivatives, wherein n is selected from 0, 1, 2, 3 or 4; m is selected from 0, 1 or 2; the dotted line represents either a single or a double bond; to processes of preparation of such compounds, to pharmaceutical compositions comprising them, and to their use in therapy and prophylaxis, in particular for the treatment of psychosis.

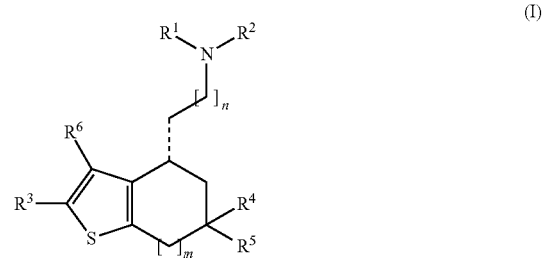

(I)

11 Claims, No Drawings

4,5,6,7-TETRAHYDROBENZO[B]THIOPHENE DERIVATIVES AND THEIR USE AS SIGMA RECEPTOR LIGANDS

CROSS REFERENCE TO RELATED APPLICATIONS

This application is a divisional of U.S. patent application Ser. No. 12/281,317, filed Aug. 29, 2008, published as US-2009/0221572 on Sep. 3, 2009, which is a U.S. National Phase filing under 35 U.S.C. §371 of International Application No. PCT/EP2007/001824, filed Mar. 2, 2007, and published as WO 2007/098961 on Sep. 7, 2007, which claims the benefit of priority from European Patent Application No. EP 0-600-4286.8, filed on Mar. 2, 2006, the disclosures of which are hereby incorporated by reference in their entirety.

FIELD OF THE INVENTION

The present invention relates to compounds having pharmacological activity towards the sigma (σ) receptor, and more particularly to some 4,5,6,7-tetrahydrobenzo[b]thiophene derivatives, to processes of preparation of such compounds, to pharmaceutical compositions comprising them, and to their use in therapy and prophylaxis, in particular for the treatment of psychosis.

BACKGROUND OF THE INVENTION

The search for new therapeutic agents has been greatly aided in recent years by better understanding of the structure of proteins and other biomolecules associated with target diseases. One important class of these proteins is the sigma (σ) receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews*, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol.

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma (σ-2) site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.*, 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Sci.*, 1996, 93:8072-8077). The existence of sigma receptors in the CNS, immune and endocrine systems have suggested a likelihood that it may serve as link between the three systems.

There is still a need to find compounds that have pharmacological activity towards the sigma receptor, being both effective and selective, and having good "drugability" properties, i.e. good pharmaceutical properties related to administration, distribution, metabolism and excretion.

SUMMARY OF THE INVENTION

We have now found a family of structurally distinct 4,5,6,7-tetrahydrobenzo[b]thiophene derivatives which are particularly selective inhibitors of the sigma receptor.

The invention is directed to compounds of general formula (I),

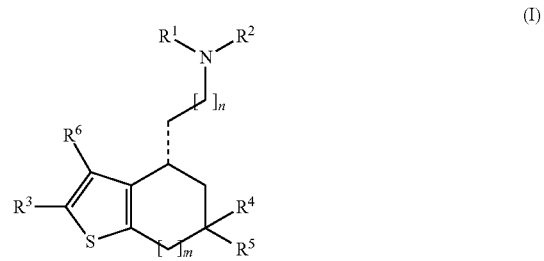

wherein
n is selected from 0, 1, 2, 3 or 4;
m is selected from 0, 1 or 2;
the dotted line ------ represents either a single or a double bond;
$R^1$ and $R^2$, identical or different, represent a hydrogen atom; $S(O)_2$—$R_{11}$; $C(O)$—$R_{11}$; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or form together with the bridging nitrogen atom an optionally at least mono-substituted heterocyclyl group which is optionally condensed with an optionally at least mono-substituted mono- or polycyclic ring system; or which is optionally bound through a spirocyclic binding to an optionally at least mono-substituted mono- or polycyclic ring system;

$R^3$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^4$ and $R^5$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or form together a 3 to 6-membered, optionally at least mono-substituted ring system;

$R^6$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^7$ represents a hydrogen atom; a linear or branched, optionally at least mono-substituted aliphatic radical;

$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment the following proviso applies:
if n is 0 and the dotted line ------ represents a single bond,
$R^1$ and $R^2$ may at the same time not represent a hydrogen atom; or may not represent a substituted methyl group substituted with 3 phenyl groups, while the other represents H.

In another embodiment the following proviso applies:
if n is 1
$R^1$ and $R^2$ may not form, together with their bridging nitrogen atom, an imidazole group.

In another embodiment the following proviso applies:
if n is 0
$R^1$ and $R^2$ may not form, together with their bridging nitrogen atom, an imidazole group.

In another embodiment the following proviso applies:
if n is 2
$R^1$ and $R^2$ may not form, together with their bridging nitrogen atom, an imidazole group.

In another embodiment the following proviso applies:
if n is 0, 1 or 2
$R^1$ and $R^2$ may not form, together with their bridging nitrogen atom, an imidazole group.

In another embodiment the following proviso applies:
if n is 2 and the dotted line ------ represents a single bond,
$R^1$ and $R^2$ may not form, together with their bridging nitrogen atom, an unsubstituted, mono- or di-alkylsubstituted piperidine group or an optionally at least monosubstituted piperazine group.

In another embodiment the following proviso applies:
if m is 1, n is 1 and the dotted line ------ represents a double bond,
$R^1$ and $R^2$ may not form, together with their bridging nitrogen atom, 5-Etoxy-2-Pyrrolidinone or 2,5-pyrrolidinedione.

In another embodiment the following proviso applies:
if n is 0 and the dotted line ------ represents a single bond,
$R^1$ and $R^2$ may at the same time not represent a hydrogen atom; or may not represent a substituted methyl group substituted with 3 phenyl groups, while the other represents H;
if n is 0, 1 or 2
$R^1$ and $R^2$ may not form, together with their bridging nitrogen atom, an imidazole group;
if n is 2 and the dotted line ------ represents a single bond,
$R^1$ and $R^2$ may not form, together with their bridging nitrogen atom, an unsubstituted or alkylsubstituted piperidine group or an optionally at least monosubstituted piperazine group.

In another embodiment the following proviso applies:
if n is 0 and the dotted line ------ represents a single bond,
$R^1$ and $R^2$ may at the same time not represent a hydrogen atom; or may not represent a substituted methyl group substituted with 3 phenyl groups, while the other represents H;
if n is 0, 1 or 2
$R^1$ and $R^2$ may not form, together with their bridging nitrogen atom, an imidazole group;
if n is 2 and the dotted line ------ represents a single bond,
$R^1$ and $R^2$ may not form, together with their bridging nitrogen atom, an unsubstituted, mono- or di-alkylsubstituted piperidine group or an optionally at least monosubstituted piperazine group;
if m is 1, n is 1 and the dotted line ------ represents a double bond, R¹ and R² may not form, together with their bridging nitrogen atom, 5-Etoxy-2-Pyrrolidinone or 2,5-pyrrolidinedione.

In another embodiment the following proviso applies:

if n is 0 and the dotted line ------ represents a single bond,

R¹ and R² may at the same time not represent a hydrogen atom; or may not represent a substituted methyl group substituted with 3 phenyl groups, while the other represents H;

if n is 0, 1 or 2

R¹ and R² may not form, together with their bridging nitrogen atom, an imidazole group;

if m is 1, n is 1 and the dotted line ------ represents a double bond,

R¹ and R² may not form, together with their bridging nitrogen atom, 5-Etoxy-2-Pyrrolidinone or 2,5-pyrrolidinedione.

In the context of this invention, alkyl radical or group is understood as meaning saturated and unsaturated, linear or branched hydrocarbons, which can be unsubstituted or mono- or polysubstituted. Thus unsaturated alkyl is understood to encompass alkenyl and alkinyl groups, like e.g. —CH=CH—CH₃ or —C≡C—CH₃, while saturated alkyl encompasses e.g. —CH₃ and —CH₂—CH₃. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also CHF₂, CF₃ or CH₂OH etc.

In the context of this invention aliphatic group or radical includes alkyl (saturated), alkenyl (unsaturated alkyl) and alkinyl (unsaturated alkyl) and thus is synonymous for: saturated or unsaturated alkyl (see above).

In the context of this invention cycloalkyl radical or group is understood as meaning saturated and unsaturated (but not aromatic) cyclic hydrocarbons (without a heteroatom in the ring), which can be unsubstituted or mono- or polysubstituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. However, mono- or polyunsaturated, preferably monounsaturated, cycloalkyls also in particular fall under the term cycloalkyl as long as the cycloalkyl is not an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, and also adamantly.

In the context of this invention alkyl-cycloalkyl is understood as meaning a cycloalkyl group (see above) being connected to another atom through an alkyl group (see above), whereas the alkyl is always saturated and linear or branched always refers to the alkyl.

In connection with alkyl or aliphatic group—unless defined otherwise—the term substituted in the context of this invention is understood as meaning replacement of at least one hydrogen radical by F, Cl, Br, I, NH₂, SH or OH, "polysubstituted" radicals being understood as meaning that the replacement takes effect both on different and on the same atoms several times with the same or different substituents, for example three times on the same C atom, as in the case of CF₃, or at different places, as in the case of e.g. —CH(OH)—CH=CH—CHCl₂.

The term $(CH_2)_{3-6}$ is to be understood as meaning —CH₂—CH₂—CH₂—, —CH₂—CH₂—CH₂—CH₂—, —CH₂—CH₂—CH₂—CH₂—CH₂— and —CH₂—CH₂—CH₂—CH₂—CH₂—CH₂—, $(CH_2)_{1-4}$ is to be understood as meaning —CH₂—, —CH₂—CH₂—, —CH₂—CH₂—CH₂— and —CH₂—CH₂—CH₂—CH₂—, $(CH_2)_{4-5}$ is to be understood as meaning —CH₂—CH₂—CH₂—CH₂— and —CH₂—CH₂—CH₂—CH₂—CH₂—, etc.

An aryl radical or group is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or monosubstituted or polysubstituted.

In the context of this invention alkyl-aryl is understood as meaning an aryl group (see above) being connected to another atom through an alkyl-group (see above), whereas the alkyl is always saturated and linear or branched always refers to the alkyl.

A heterocyclyl radical or group is understood as meaning heterocyclic ring systems, saturated or unsaturated ring which contains one or more heteroatoms from the group consisting of nitrogen, oxygen and/or sulfur in the ring and can also be mono- or polysubstituted. Examples which may be mentioned from the group of heteroaryls are furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole and quinazoline.

In the context of this invention alkyl-heterocylyl is understood as meaning a heterocyclyl group (see above) being connected to another atom through an alkyl group (see above), whereas the alkyl is always saturated and linear or branched always refers to the alkyl.

In connection with aryl or alkyl-aryl, cycloalkyl or alkyl-cycloalkyl, heterocyclyl or alkyl-heterocylyl, substituted is understood—unless defined otherwise—as meaning substitution of the ring-system of the aryl or alkyl-aryl, cycloalkyl or alkyl-cycloalkyl; heterocyclyl or alkyl-heterocyclyl by OH, SH, =O, halogen (F, Cl, Br, I), CN, NO₂, COOH; NR$_x$R$_y$, with R$_x$, and R$_y$ independently being either H or a saturated or unsaturated, linear or branched, substituted or unsubstituted $C_{1-6}$-alkyl; a saturated or unsaturated, linear or branched, substituted or unsubstituted $C_{1-6}$alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—C$_{1-6}$-alkyl-group; a saturated or unsaturated, linear or branched, substituted or unsubstituted —C(O)—O—C$_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl.

The term "ring system" according to the present invention refers to ring systems comprising saturated or unsaturated or aromatic carbocyclic ring systems which contain optionally at least one heteroatom selected from N, O or S as ring member and which are optionally at least mono-substituted. Said ring systems may be condensed to other carbocyclic ring systems such as aryl groups, heterocyclyl groups, cycloalkyl groups, etc.

The term "condensed" according to the present invention means that a ring or ring-system is attached to another ring or ring-system, whereby the terms "annulated" or "annelated" are also used by those skilled in the art to designate this kind of attachment.

The term "bound through a spirocyclic binding to an optionally at least mono-substituted mono- or polycyclic ring system" means a binding through one C-Atom between two ring systems, like e.g. in below structure where the spirocyclic binding is marked by an arrow:

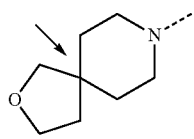

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid— as an anion with at least one, preferably inorganic, cation which is physiologically tolerated—especially if used on humans and/or mammals. The salts of the alkali metals and alkaline earth metals are particularly preferred, and also those with NH$_4$, but in particular (mono)- or (di)sodium, (mono)- or (di)potassium, magnesium or calcium salts.

These physiologically acceptable salts can also be formed with anions or acids in the context of this invention is understood as meaning salts of at least one of the compounds used according to the invention—usually protonated, for example on the nitrogen—as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be in crystalline form or either as free compounds or as solvates and it is intended that those forms are within the scope of the present invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon or $^{15}$N-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or, or of its salts, solvates or prodrugs.

The term "pharmacological tool" refers to the property of compounds of the invention through which they are particularly selective ligands for Sigma receptors which implies that compound of formula (I), described in this invention, can be used as a model for testing other compounds as sigma ligands, ex. a radiactive ligands being replaced, and can also be used for modeling physiological actions related to sigma receptors.

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In a preferred embodiment (according to subtype A) of the invention the compounds according to the invention are of general formula (I)

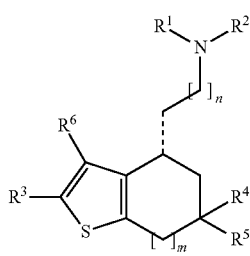

(I)

wherein
n is selected from 0 or 1;
m is selected from 0, 1 or 2;
the dotted line ------ represents either a single or a double bond;
$R^1$ and $R^2$, identical or different, represent a hydrogen atom; $S(O)_2$—$R_{11}$; $C(O)$—$R_{11}$; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;
or
form together with the bridging nitrogen atom an optionally at least mono-substituted heterocyclyl group which is optionally condensed with an optionally at least mono-substituted mono- or polycyclic ring system; or which is optionally bound through a spirocyclic binding to an optionally at least mono-substituted mono- or polycyclic ring system;
$R^3$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;
$R^4$ and $R^5$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;
or
form together a 3 to 6-membered, optionally at least mono-substituted ring system;
$R^6$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;
$R^7$ represents a hydrogen atom; a linear or branched, optionally at least mono-substituted aliphatic radical;
$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment (according to subtype A) of the invention the following proviso applies:
$R^1$ and $R^2$ may not form, together with their bridging nitrogen atom, an imidazole group;

In another preferred embodiment (according to subtype A) of the invention the following proviso applies:
if n is 0 and the dotted line ------ represents a single bond,
$R^1$ and $R^2$ may at the same time not represent a hydrogen atom; or may not represent a substituted methyl group substituted with 3 phenyl groups, while the other represents H;

In a preferred embodiment (according to subtype A) of the invention the compounds according to the invention are of general formula (I)
wherein
m is selected from 0, 1 or 2;
the dotted line ------ represents either a single or a double bond;
$R^1$ represents a hydrogen atom; $S(O)_2$—$R_{11}$; $C(O)$—$R_{11}$; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

$R^2$ represents $S(O)_2$—$R_{11}$; $C(O)$—$R_{11}$; a linear or branched, saturated or unsaturated, optionally at least mono-substituted aliphatic radical, with the substituents selected from OH, SH, $NH_2$, F, Cl, Br, I; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or $R^1$ and $R^2$ form together with the bridging nitrogen atom an optionally at least mono-substituted heterocyclyl group selected from:

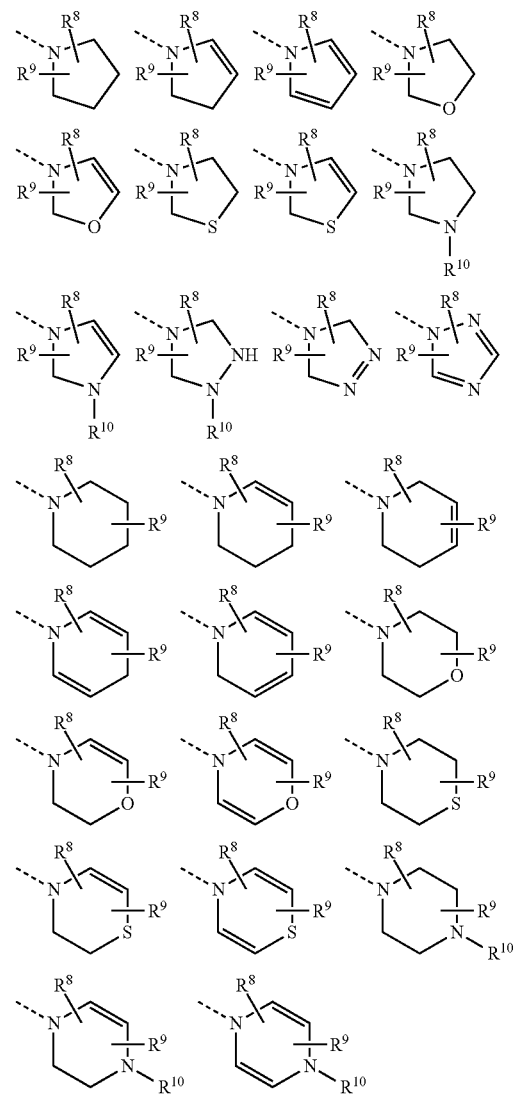

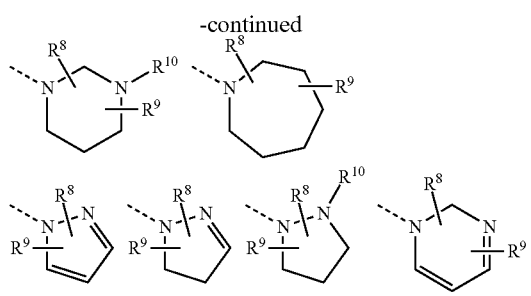

which is optionally condensed with an optionally at least mono-substituted mono- or polycyclic ring system; or which is optionally bound through a spirocyclic binding to an optionally at least mono-substituted mono- or polycyclic ring system;

$R^3$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^4$ and $R^5$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;
or
form together a 3 to 6-membered, optionally at least mono-substituted ring system;

$R^6$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^7$ represents a hydrogen atom; a linear or branched, optionally at least mono-substituted aliphatic radical;

$R^8$ and $R^9$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;
or
$R^8$ and $R^9$, binding to the same C-atom in the ring, form together with this C-atom in the ring an optionally at least mono-substituted mono- or polycyclic ring system;
or
$R^8$ and $R^9$, binding to different adjacent ring members; form together with these ring members an optionally at least mono-substituted mono- or polycyclic ring system;

$R^{10}$ represents hydrogen; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group.

In a preferred embodiment (according to subtype A) of the invention the compounds according to the invention are of general formula (I)
wherein
n is selected from 0 or 1;
m is selected from 0, 1 or 2;
the dotted line ------ represents either a single or a double bond;
$R^1$ represents a hydrogen atom; a linear or branched, saturated or unsaturated, optionally at least mono-substituted aliphatic radical;
$R^2$ represents $S(O)_2$—$R_{11}$; $C(O)$—$R_{11}$; a linear or branched, saturated or unsaturated, optionally at least mono-substituted aliphatic radical, with the substituents selected from OH, SH, $NH_2$, F, Cl, Br, I; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/ or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or $R^1$ and $R^2$ form together with the bridging nitrogen atom an optionally at least mono-substituted heterocyclyl group selected from:

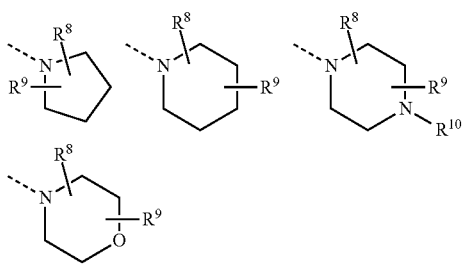

$R^3$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^4$ and $R^5$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or form together a 3 to 6-membered, optionally at least mono-substituted ring system;

$R^6$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^7$ represents a hydrogen atom; a linear or branched, optionally at least mono-substituted aliphatic radical;

$R^8$ and $R^9$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members; form together with these ring members an optionally at least mono-substituted mono- or polycyclic ring system;

$R^{10}$ represents hydrogen; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group.

In a preferred embodiment (according to subtype B) of the invention the compounds according to the invention are of general formula (I)

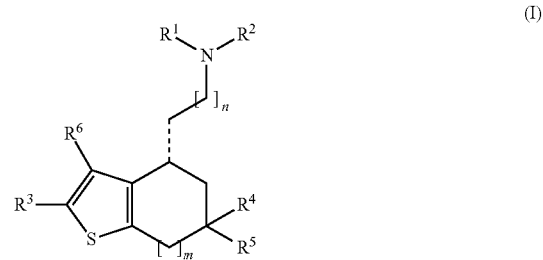

wherein n is 2;

m is selected from 0, 1 or 2;

the dotted line ------ represents either a single or a double bond;

$R^1$ and $R^2$, identical or different, represent a hydrogen atom; $S(O)_2$—$R_{11}$; $C(O)$—$R_{11}$; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or form together with the bridging nitrogen atom an optionally at least mono-substituted heterocyclyl group which is optionally condensed with an optionally at least mono-substituted mono- or polycyclic ring system; or which is optionally bound through a spirocyclic binding to an optionally at least mono-substituted mono- or polycyclic ring system;

$R^3$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^4$ and $R^5$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or form together a 3 to 6-membered, optionally at least mono-substituted ring system;

$R^6$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^7$ represents a hydrogen atom; a linear or branched, optionally at least mono-substituted aliphatic radical;

$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment (according to subtype B above) of the invention the following proviso applies:

$R^1$ and $R^2$ may not form, together with their bridging nitrogen atom, an imidazole group;

In another preferred embodiment (according to subtype B above) of the invention the following proviso applies:

if the dotted line ------ represents a single bond, $R^1$ and $R^2$ may not form, together with their bridging nitrogen atom, a piperidine group; or a piperazine group;

In a preferred embodiment (according to subtype B) of the invention the compounds according to the invention are of general formula (I)

wherein m is selected from 0, 1 or 2;

the dotted line ------ represents either a single or a double bond;

$R^1$ and $R^2$, identical or different, represent a hydrogen atom; $S(O)_2$—$R_{11}$; $C(O)$—$R_{11}$; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or form together with the bridging nitrogen atom an optionally at least mono-substituted heterocyclyl group selected from:

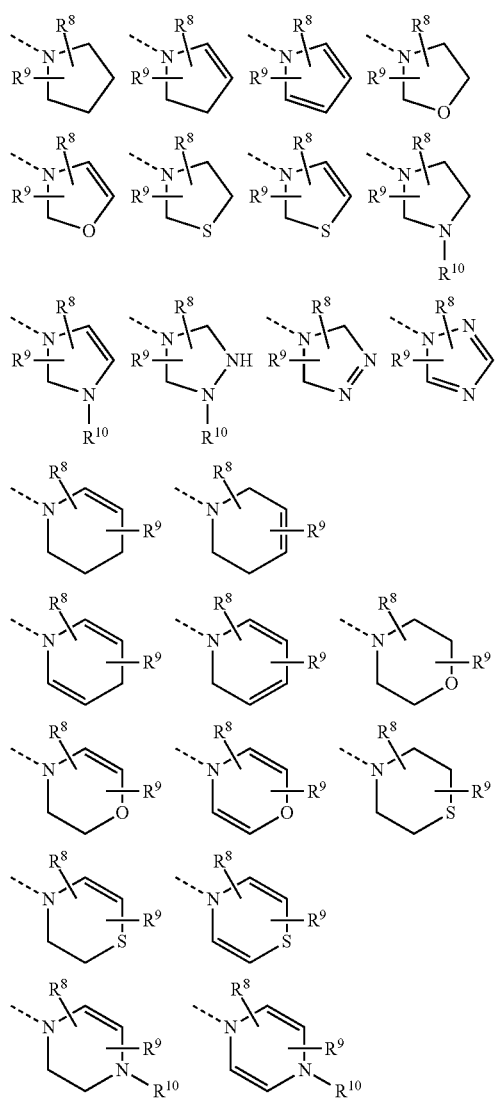

-continued

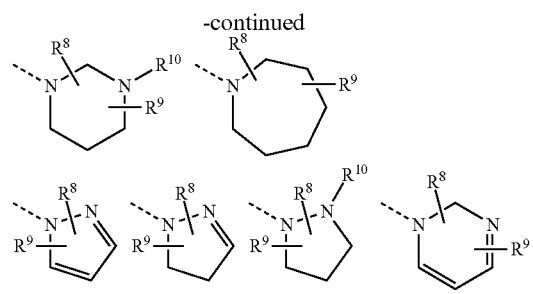

which is optionally condensed with an optionally at least mono-substituted mono- or polycyclic ring system; or which is optionally bound through a spirocyclic binding to an optionally at least mono-substituted mono- or polycyclic ring system;

$R^3$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^4$ and $R^5$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or form together a 3 to 6-membered, optionally at least mono-substituted ring system;

$R^6$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^7$ represents a hydrogen atom; a linear or branched, optionally at least mono-substituted aliphatic radical $R^8$ and $R^9$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^8$ and $R^9$, binding to the same C-atom in the ring, form together with this C-atom in the ring an optionally at least mono-substituted mono- or polycyclic ring system; or $R^8$ and $R^9$, binding to different adjacent ring members; form together with these ring members an optionally at least mono-substituted mono- or polycyclic ring system;

$R^{10}$ represents hydrogen; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group.

In a preferred embodiment (according to subtype B) of the invention the compounds according to the invention are of general formula (I)

wherein m is selected from 0, 1 or 2;

the dotted line ------ represents either a single or a double bond;

$R^1$ represents a hydrogen atom; a linear or branched, saturated or unsaturated, optionally at least mono-substituted aliphatic radical;

$R^2$ represents $S(O)_2$—$R_{11}$; $C(O)$—$R_{11}$; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or $R^1$ and $R^2$ form together with the bridging nitrogen atom an optionally at least mono-substituted heterocyclyl group selected from:

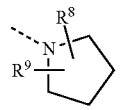

$R^3$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^4$ and $R^5$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or form together a 3 to 6-membered, optionally at least mono-substituted ring system;

$R^6$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^7$ represents a hydrogen atom; a linear or branched, optionally at least mono-substituted aliphatic radical;

$R^8$ and $R^9$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members; form together with these ring members an optionally at least mono-substituted mono- or polycyclic ring system;

$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group.

In a preferred embodiment (according to subtype C) of the invention the compounds according to the invention are of general formula (I)

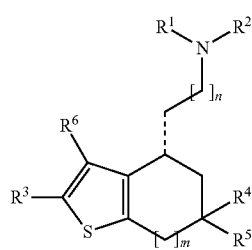

(I)

wherein n is selected from 3 or 4;

m is selected from 0, 1 or 2;

the dotted line ------ represents either a single or a double bond;

$R^1$ and $R^2$, identical or different, represent a hydrogen atom; $S(O)_2$—$R_{11}$; $C(O)$—$R_{11}$; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or form together with the bridging nitrogen atom an optionally at least mono-substituted heterocyclyl group which is optionally condensed with an optionally at least mono-substituted mono- or polycyclic ring system; or which is optionally bound through a spirocyclic binding to an optionally at least mono-substituted mono- or polycyclic ring system;

$R^3$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^4$ and $R^5$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or form together a 3 to 6-membered, optionally at least mono-substituted ring system;

$R^6$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^7$ represents a hydrogen atom; a linear or branched, optionally at least mono-substituted aliphatic radical;

$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment (according to subtype C) of the invention the compounds according to the invention are of general formula (I)

wherein m is selected from 0, 1 or 2;

the dotted line ------ represents either a single or a double bond;

$R^1$ and $R^2$, identical or different, represent a hydrogen atom; $S(O)_2$—$R_{11}$; $C(O)$—$R_{11}$; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or form together with the bridging nitrogen atom an optionally at least mono-substituted heterocyclyl group selected from:

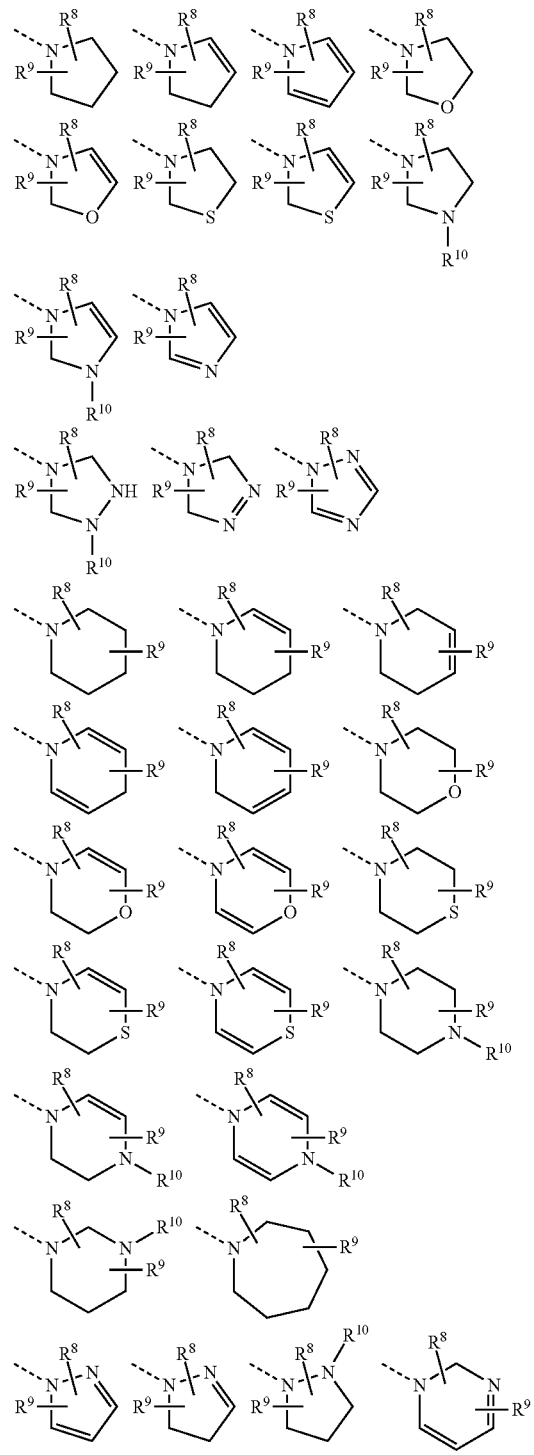

which is optionally condensed with an optionally at least mono-substituted mono- or polycyclic ring system; or which is optionally bound through a spirocyclic binding to an optionally at least mono-substituted mono- or polycyclic ring system;

$R^3$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^4$ and $R^5$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or form together a 3 to 6-membered, optionally at least mono-substituted ring system;

$R^6$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^7$ represents a hydrogen atom; a linear or branched, optionally at least mono-substituted aliphatic radical $R^8$ and $R^9$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members; form together with these ring members an optionally at least mono-substituted mono- or polycyclic ring system;

$R^{10}$ represents hydrogen; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group.

$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group.

In a preferred embodiment (according to subtype C) of the invention the compounds according to the invention are of general formula (I)

wherein m is selected from 0, 1 or 2;

the dotted line ------ represents either a single or a double bond;

$R^1$ represents a hydrogen atom; a linear or branched, saturated or unsaturated, optionally at least mono-substituted aliphatic radical;

$R^2$ represents $S(O)_2$—$R_{11}$; $C(O)$—$R_{11}$; a linear or branched, saturated or unsaturated, optionally at least mono-substituted aliphatic radical, with the substituents selected from OH, SH, $NH_2$, F, Cl, Br, I; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or $R^1$ and $R^2$ form together with the bridging nitrogen atom an optionally at least mono-substituted heterocyclyl group selected from:

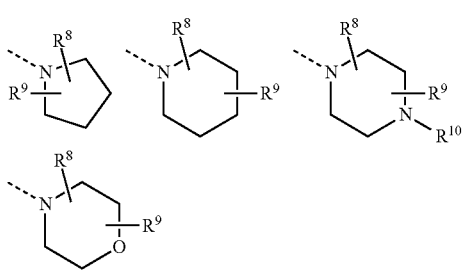

$R^3$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^4$ and $R^5$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or form together a 3 to 6-membered, optionally at least mono-substituted ring system;

$R^6$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^7$ represents a hydrogen atom; a linear or branched, optionally at least mono-substituted aliphatic radical;

$R^8$ and $R^9$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members, form together with these ring members an optionally at least mono-substituted mono- or polycyclic ring system;

$R^{10}$ represents hydrogen; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group.

In a preferred embodiment of the invention the compounds according to the invention are of general formula (I), wherein m is selected from 0 or 1; preferably is 1.

In a preferred embodiment of the invention the compounds according to the invention are of general formula (I), wherein the dotted line ------ represents single bond.

In a preferred embodiment of the invention the compounds according to the invention are of general formula (I), wherein the dotted line ------ represents a double bond.

In a preferred embodiment of the invention the compounds according to the invention are of general formula (I), wherein
$R^3$ represents a hydrogen atom; a halogen; $OR^7$; a linear or branched, saturated or unsaturated, optionally at least mono-substituted aliphatic radical;
preferably H, Cl, F, Br, I, $CF_3$, $CH_3$, $C_2H_5$, OH, $OCH_3$, $OC_2H_5$,
most preferably H.

In a preferred embodiment of the invention the compounds according to the invention are of general formula (I), wherein
$R^6$ represents a hydrogen atom; a halogen; $OR^7$; a linear or branched, saturated or unsaturated, optionally at least mono-substituted aliphatic radical;
preferably H, Cl, F, Br, I, $CF_3$, $CH_3$, $C_2H_5$, OH, $OCH_3$, $OC_2H_5$;
most preferably H.

In a preferred embodiment of the invention the compounds according to the invention are of general formula (I), wherein
$R^4$ and $R^5$, identical or different, represent a hydrogen atom; a halogen; $OR^7$; a linear or branched, saturated or unsaturated, optionally at least mono-substituted aliphatic radical;
preferably H, Cl, F, Br, I, $CF_3$, $CH_3$, $C_2H_5$, OH, $OCH_3$, $OC_2H_5$, $OCF_3$;
most preferably H.

In a preferred embodiment of the invention the compounds according to the invention are of general formula (I), wherein $R^7$ represents H, $CF_3$, $CH_3$ or $C_2H_5$.

In a preferred embodiment of the invention the compounds according to the invention are of general formula (I), wherein
$R^{10}$ represents H, $CF_3$, $CH_3$ or $C_2H_5$; an optionally at least mono-substituted phenyl or naphthyl radical; an optionally at least mono-substituted heterocyclyl group; an optionally at least mono-substituted —$CH_2$-phenyl, —CH$_2$-naphthyl —CH$_2$—CH$_2$-phenyl or —CH$_2$—CH$_2$-naphthyl; an optionally at least mono-substituted —CH$_2$-heterocyclyl group or —CH$_2$—CH$_2$-heterocyclyl group.

In a preferred embodiment of the invention the compounds according to the invention are of general formula (I), wherein R$^{11}$ represents an optionally at least mono-substituted phenyl or naphthyl radical; an optionally at least mono-substituted heterocyclyl group; an optionally at least mono-substituted —CH$_2$-phenyl, —CH$_2$-naphthyl, —CH$_2$—CH$_2$-phenyl or —CH$_2$—CH$_2$-naphthyl; an optionally at least mono-substituted —CH$_2$-heterocyclyl group or —CH$_2$—CH$_2$-heterocyclyl group.

In a preferred embodiment of the invention the compounds according to the invention are of general formula (I), wherein R$^8$ and R$^9$, identical or different, represent H; OH; an optionally at least mono-substituted phenyl or naphthyl radical; an optionally at least mono-substituted heterocyclyl group; an optionally at least mono-substituted —CH$_2$-phenyl, —CH$_2$-naphthyl, —CH$_2$—CH$_2$-phenyl or —CH$_2$—CH$_2$-naphthyl; an optionally at least mono-substituted —CH$_2$-heterocyclyl group or —CH$_2$—CH$_2$-heterocyclyl group.

In a preferred embodiment of the invention the compounds according to the invention are of general formula (I), wherein R$^8$ and R$^9$, binding to the same C-atom in the ring, form together with this C-atom in the ring an optionally at least mono-substituted mono- or polycyclic ring system.

In a preferred embodiment of the invention the compounds according to the invention are of general formula (I), wherein R$^8$ and R$^9$, binding to different adjacent ring members, form together with these ring members an optionally at least mono-substituted mono- or polycyclic ring system.

In a preferred embodiment of the invention (according to subtype A) the compounds according to the invention are of general formula (I)

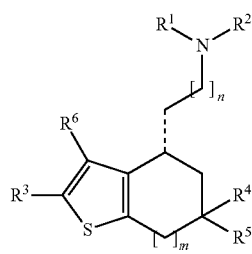

(I)

wherein
n is selected from 0 or 1;
m is selected from 0 or 1;
the dotted line ------ represents either a single or a double bond;
R$^1$ represents a hydrogen atom; a linear or branched, saturated or unsaturated, optionally at least mono-substituted aliphatic radical;
R$^2$ represents S(O)$_2$—R$_{11}$; C(O)—R$_{11}$; a linear or branched, saturated or unsaturated, optionally at least mono-substituted aliphatic radical, with the substituents selected from OH, SH, NH$_2$, F, Cl, Br, I; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or
R$^1$ and R$^2$ form together with the bridging nitrogen atom an optionally at least mono-substituted heterocyclyl group selected from:

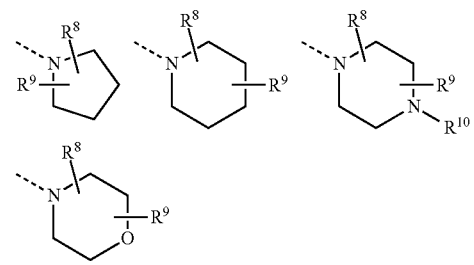

R$^3$ represents a hydrogen atom; a halogen; OR$^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

R$^4$ and R$^5$, identical or different, represent a hydrogen atom; a halogen; OR$^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or form together a 3 to 6-membered, optionally at least mono-substituted ring system;

$R^6$ represents a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^7$ represents a hydrogen atom; a linear or branched, optionally at least mono-substituted aliphatic radical;

$R^8$ and $R^9$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members; form together with these ring members an optionally at least mono-substituted mono- or polycyclic ring system;

$R^{10}$ represents hydrogen; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the invention (Subtype A)—especially of the embodiment directly above—the compounds according to the invention are of general formula (I), wherein n is selected from 0 or 1; preferably is 1;

m is selected from 0 or 1; preferably is 1;

the dotted line ------ represents either a single or a double bond; preferably is a single bond;

$R^1$ represents a hydrogen atom; a linear or branched, saturated or unsaturated, optionally at least mono-substituted aliphatic radical;

$R^2$ represents $S(O)_2$—$R_{11}$; $C(O)$—$R_{11}$; a linear or branched, saturated or unsaturated, optionally at least mono-substituted aliphatic radical, with the substituents selected from OH, SH, $NH_2$, F, Cl, Br, I; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or $R^1$ and $R^2$ form together with the bridging nitrogen atom an optionally at least mono-substituted heterocyclyl group selected from:

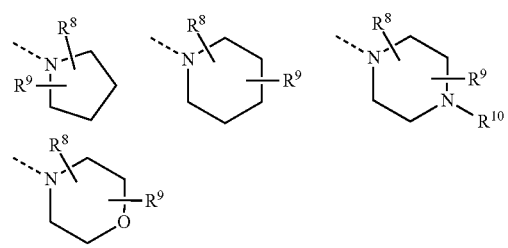

R³ represents a hydrogen atom; a halogen; OR⁷; a linear or branched, saturated or unsaturated, optionally at least mono-substituted aliphatic radical; preferably H, Cl, F, Br, I, CF₃, CH₃, C₂H₅, OH, OCH₃, OC₂H₅; most preferably H;

R⁶ represents a hydrogen atom; a halogen; OR⁷; a linear or branched, saturated or unsaturated, optionally at least mono-substituted aliphatic radical; preferably H, Cl, F, Br, I, CF₃, CH₃, C₂H₅, OH, OCH₃, OC₂H₅; most preferably H;

R⁴ and R⁵, identical or different, represent a hydrogen atom; a halogen; OR⁷; a linear or branched, saturated or unsaturated, optionally at least mono-substituted aliphatic radical; preferably H, Cl, F, Br, I, CF₃, CH₃, C₂H₅, OH, OCH₃, OC₂H₅, OCF₃; most preferably H;

R⁷ represents H, CF₃, CH₃ or C₂H₅;

R¹⁰ represents H, CF₃, CH₃ or C₂H₅; an optionally at least mono-substituted phenyl or naphthyl radical; an optionally at least mono-substituted heterocyclyl group; an optionally at least mono-substituted —CH₂-phenyl, —CH₂-naphthyl —CH₂—CH₂-phenyl or —CH₂—CH₂-naphthyl; an optionally at least mono-substituted —CH₂-heterocyclyl group or —CH₂—CH₂-heterocyclyl group;

R¹¹ represents an optionally at least mono-substituted phenyl or naphthyl radical; an optionally at least mono-substituted heterocyclyl group; an optionally at least mono-substituted —CH₂-phenyl, —CH₂-naphthyl, —CH₂—CH₂-phenyl or —CH₂—CH₂-naphthyl; an optionally at least mono-substituted —CH₂-heterocyclyl group or —CH₂—CH₂-heterocyclyl group.

R⁸ and R⁹, identical or different, represent H; OH; an optionally at least mono-substituted phenyl or naphthyl radical; an optionally at least mono-substituted heterocyclyl group; an optionally at least mono-substituted —CH₂-phenyl, —CH₂-naphthyl, —CH₂—CH₂-phenyl or —CH₂—CH₂-naphthyl; an optionally at least mono-substituted —CH₂-heterocyclyl group or —CH₂—CH₂-heterocyclyl group;

or

R⁸ and R⁹, binding to the same C-atom in the ring, form together with this C-atom in the ring an optionally at least mono-substituted mono- or polycyclic ring system;

or

R⁸ and R⁹, binding to different adjacent ring members, form together with these ring members an optionally at least mono-substituted mono- or polycyclic ring system.

In a preferred embodiment of the invention (Subtype A) the compounds according to the invention are of general formula (IA),

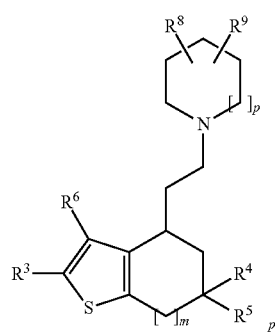

(IA)

wherein m is selected from 0 or 1;

p is selected from 0 or 1;

R³ represents a hydrogen atom; a halogen; OR⁷; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

R⁴ and R⁵, identical or different, represent a hydrogen atom; a halogen; OR⁷; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or form together a 3 to 6-membered, optionally at least mono-substituted ring system;

R⁶ represents a hydrogen atom; a halogen; OR⁷; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

R⁷ represents a hydrogen atom; a linear or branched, optionally at least mono-substituted aliphatic radical;

R⁸ and R⁹, identical or different, represent a hydrogen atom; a halogen; OR⁷; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or

R⁸ and R⁹, binding to the same C-atom in the ring, form together with this C-atom in the ring an optionally at least mono-substituted mono- or polycyclic ring system;

or

R⁸ and R⁹, binding to different adjacent ring members; form together with these ring members an optionally at least mono-substituted mono- or polycyclic ring system;

R¹¹ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the invention (Subtype A) the compounds according to the invention are of general formula (IA), wherein m is selected from 0 or 1; preferably is 1;
p is selected from 0 or 1;
$R^3$ represents a hydrogen atom; a halogen; $OR^7$; a linear or branched, saturated or unsaturated, optionally at least mono-substituted aliphatic radical; preferably H, Cl, F, Br, I, $CF_3$, $CH_3$, $C_2H_5$, OH, $OCH_3$, $OC_2H_5$; most preferably H;
$R^6$ represents a hydrogen atom; a halogen; $OR^7$; a linear or branched, saturated or unsaturated, optionally at least mono-substituted aliphatic radical; preferably H, Cl, F, Br, I, $CF_3$, $CH_3$, $C_2H_5$, OH, $OCH_3$, $OC_2H_5$; most preferably H;
$R^4$ and $R^5$, identical or different, represent a hydrogen atom; a halogen; $OR^7$; a linear or branched, saturated or unsaturated, optionally at least mono-substituted aliphatic radical; preferably H, Cl, F, Br, I, $CF_3$, $CH_3$, $C_2H_5$, OH, $OCH_3$, $OC_2H_5$, $OCF_3$; most preferably H;
$R^7$ represents H, $CF_3$, $CH_3$ or $C_2H_5$;
$R^{11}$ represents an optionally at least mono-substituted phenyl or naphthyl radical; an optionally at least mono-substituted heterocyclyl group; an optionally at least mono-substituted —$CH_2$-phenyl, —$CH_2$-naphthyl, —$CH_2$—$CH_2$-phenyl or —$CH_2$—$CH_2$-naphthyl; an optionally at least mono-substituted —$CH_2$-heterocyclyl group or —$CH_2$—$CH_2$-heterocyclyl group.
$R^8$ and $R^9$, identical or different, represent H; OH; an optionally at least mono-substituted phenyl or naphthyl radical; an optionally at least mono-substituted heterocyclyl group; an optionally at least mono-substituted —$CH_2$-phenyl, —$CH_2$-naphthyl, —$CH_2$—$CH_2$-phenyl or —$CH_2$—$CH_2$-naphthyl; an optionally at least mono-substituted —$CH_2$-heterocyclyl group or —$CH_2$—$CH_2$-heterocyclyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members, form together with these ring members an optionally at least mono-substituted mono- or polycyclic ring system.

In a preferred embodiment of the invention (Subtype A) the compounds according to the invention are of general formula (IA), wherein $R^8$ represents H or OH;
$R^9$ represents H; $CH_3$; an optionally at least mono-substituted phenyl; an optionally at least mono-substituted naphthyl radical; an optionally at least mono-substituted heterocyclyl group;
preferably
$R^8$ represents H or OH;
$R^9$ represents H, $CH_3$, an unsubstituted phenyl; a phenyl substituted by $C(O)CH_3$, COOH, $CH_3$, $OCH_3$, $CF_3$, Cl, F, $NH_2$, C(O)—O—$CH_3$, halogen (especially Cl or F);

an unsubstituted naphthyl; an optionally at least mono-substituted heterocyclyl group, selected from:

most preferably $R^8$ represents H or OH;

$R^9$ represents H or $CH_3$, an unsubstituted phenyl; a phenyl substituted by $C(O)CH_3$, COOH, $CH_3$, $OCH_3$, $CF_3$, Cl, F, $NH_2$, C(O)—O—$CH_3$, halogen (especially Cl or F); an unsubstituted naphthyl; an optionally at least mono-substituted heterocyclyl group, selected from:

with $R^8$ being a substitute in the ortho, meta or para position if p is 1 or in 2- or 3-position if p is 0.

In a preferred embodiment of the invention (Subtype A) the compounds according to the invention are of general formula (IA), wherein R⁸ and R⁹, binding to the same C-atom in the ring, form together with this C-atom in the ring an optionally at least mono-substituted mono- or polycyclic ring system,
preferably leading together with the substituted heterocycle according to formula 1B to spirocyclic structures selected from:

A (if p is 1)

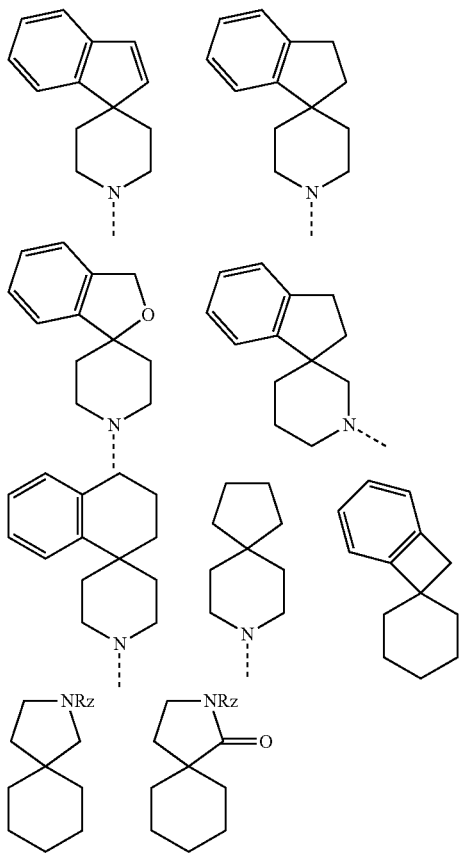

or B if p is 0

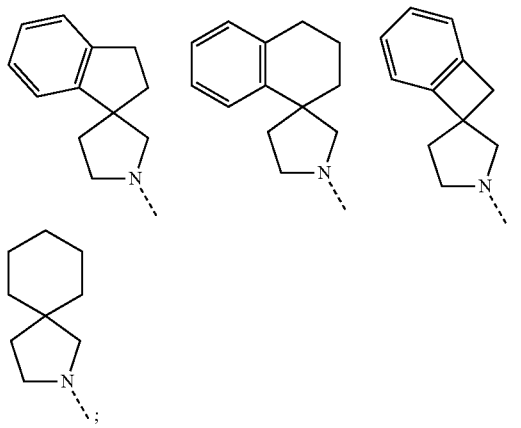

optionally at least mono-substituted, with Rz being preferably a substituted phenyl, an unsubstituted phenyl, a benzyl or an alkyl.

In a preferred embodiment of the invention (Subtype A) the compounds according to the invention are of general formula (IA), wherein R⁸ and R⁹, binding to the same C-atom in the ring, form together with this C-atom in the ring an optionally at least mono-substituted mono- or polycyclic ring system,
preferably leading together with the substituted heterocycle to the following structure (if p is 1):

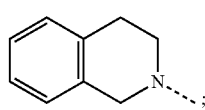

optionally at least mono-substituted, most preferably on the aromatic ring.

A very preferred embodiment of the invention are compounds according to general formula I

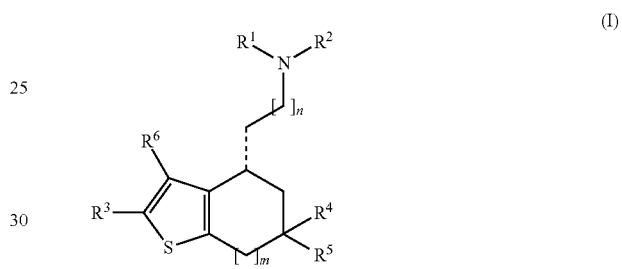

wherein
n is selected from 0 or 1;
m is selected from 0 or 1;
the dotted line ------ represents either a single or a double bond;
R¹ represents a hydrogen atom; a linear or branched, saturated or unsaturated, optionally at least mono-substituted aliphatic radical;
R² represents a linear or branched, saturated or unsaturated, optionally at least mono-substituted aliphatic radical, with the substituents selected from OH, SH, NH₂, F, Cl, Br, I; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or $R^1$ and $R^2$ form together with the bridging nitrogen atom an optionally at least mono-substituted heterocyclyl group selected from:

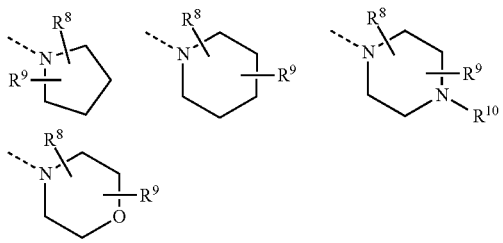

$R^3$ represents a hydrogen atom;
$R^4$ and $R^5$, identical or different, represent a hydrogen atom;
$R^6$ represents a hydrogen atom;
$R^7$ represents a hydrogen atom; a linear or branched, optionally at least mono-substituted aliphatic radical;
$R^8$ and $R^9$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members; form together with these ring members an optionally at least mono-substituted mono- or polycyclic ring system;

$R^{10}$ represents hydrogen; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment the following provisos apply:
if n is 0 and the dotted line ------ represents a single bond,
$R^1$ and $R^2$ may at the same time not represent a hydrogen atom; or may not represent a substituted methyl group substituted with 3 phenyl groups, while the other represents H;
if m is 1, n is 1 and the dotted line ------ represents a double bond,
$R^1$ and $R^2$ may not form, together with their bridging nitrogen atom, 5-Etoxy-2-Pyrrolidinone or 2,5-pyrrolidinedione.

In an embodiment the following proviso applies:
if n is 0 and the dotted line ------ represents a single bond,
$R^1$ and $R^2$ may at the same time not represent a hydrogen atom; or may not represent a substituted methyl group substituted with 3 phenyl groups, while the other represents H.

In an embodiment the following proviso applies:
if m is 1, n is 1 and the dotted line ------ represents a double bond,
$R^1$ and $R^2$ may not form, together with their bridging nitrogen atom, 5-Etoxy-2-Pyrrolidinone or 2,5-pyrrolidinedione.

Another very preferred embodiment of the invention are compounds according to general formula I, wherein
n is selected from 0 or 1; preferably is 1;
m is selected from 0 or 1; preferably is 1;
the dotted line ------ represents either a single or a double bond;
$R^1$ represents a hydrogen atom; a linear or branched, saturated or unsaturated, optionally at least mono-substituted aliphatic radical;
$R^2$ represents a linear or branched, saturated or unsaturated, optionally at least mono-substituted aliphatic radical, with the substituents selected from OH, SH, $NH_2$, F, Cl, Br, I; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or $R^1$ and $R^2$ form together with the bridging nitrogen atom an optionally at least mono-substituted heterocyclyl group selected from:

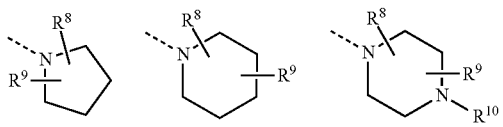

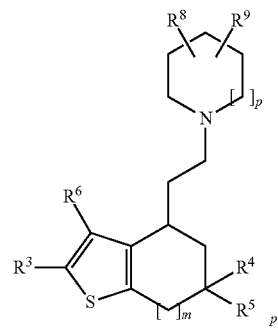

$R^3$ represents a hydrogen atom;
$R^6$ represents a hydrogen atom;
$R^4$ and $R^5$, identical or different, represent a hydrogen atom;
$R^7$ represents H, $CF_3$, $CH_3$ or $C_2H_5$;
$R^{10}$ represents H, $CF_3$, $CH_3$ or $C_2H_5$; an optionally at least mono-substituted phenyl or naphthyl radical; an optionally at least mono-substituted heterocyclyl group; an optionally at least mono-substituted —$CH_2$-phenyl, —$CH_2$-naphthyl —$CH_2$—$CH_2$-phenyl or —$CH_2$—$CH_2$-naphthyl; an optionally at least mono-substituted —$CH_2$-heterocyclyl group or —$CH_2$—$CH_2$-heterocyclyl group;
$R^8$ and $R^9$, identical or different, represent H; OH; an optionally at least mono-substituted phenyl or naphthyl radical; an optionally at least mono-substituted heterocyclyl group; an optionally at least mono-substituted —$CH_2$-phenyl, —$CH_2$-naphthyl, —$CH_2$—$CH_2$-phenyl or —$CH_2$—$CH_2$-naphthyl; an optionally at least mono-substituted —$CH_2$-heterocyclyl group or —$CH_2$—$CH_2$-heterocyclyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members, form together with these ring members an optionally at least mono-substituted mono- or polycyclic ring system.

Another very preferred embodiment of the invention are compounds according to general formula (IA), (IA)

wherein
m is selected from 0 or 1;
p is selected from 0 or 1;
$R^3$ represents a hydrogen atom;
$R^4$ and $R^5$, identical or different, represent a hydrogen atom;
$R^6$ represents a hydrogen atom;
$R^7$ represents a hydrogen atom; a linear or branched, optionally at least mono-substituted aliphatic radical;
$R^8$ and $R^9$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members; form together with these ring members an optionally at least mono-substituted mono- or polycyclic ring system;
$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another very preferred embodiment of the invention are compounds according to general formula (IA), wherein
m is selected from 0 or 1; preferably is 1;
p is selected from 0 or 1;
$R^3$ represents a hydrogen atom;
$R^6$ represents a hydrogen atom;

$R^4$ and $R^5$, identical or different, represent a hydrogen atom;

$R^7$ represents H, $CF_3$, $CH_3$ or $C_2H_5$;

$R^8$ and $R^9$, identical or different, represent H; OH; an optionally at least mono-substituted phenyl or naphthyl radical; an optionally at least mono-substituted heterocyclyl group; an optionally at least mono-substituted —$CH_2$-phenyl, —$CH_2$-naphthyl, —$CH_2$—$CH_2$-phenyl or —$CH_2$—$CH_2$-naphthyl; an optionally at least mono-substituted —$CH_2$-heterocyclyl group or —$CH_2$—$CH_2$-heterocyclyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members, form together with these ring members an optionally at least mono-substituted mono- or polycyclic ring system.

Another very preferred embodiment of the invention are compounds according to general formula (IA), wherein $R^8$ represents H or OH;

$R^9$ represents H; $CH_3$; an optionally at least mono-substituted phenyl; an optionally at least mono-substituted naphthyl radical; an optionally at least mono-substituted heterocyclyl group;

preferably $R^8$ represents H or OH;

$R^9$ represents H, $CH_3$, an unsubstituted phenyl; a phenyl substituted by $C(O)CH_3$, COOH, $CH_3$, $OCH_3$, $CF_3$, Cl, F, $NH_2$, C(O)—O—$CH_3$, halogen (especially Cl or F); an unsubstituted naphthyl; an optionally at least mono-substituted heterocyclyl group, selected from:

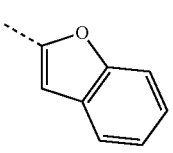 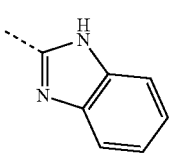 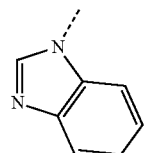

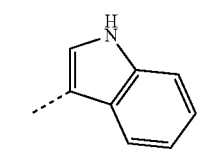 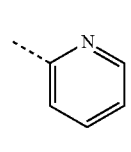 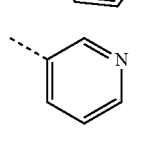

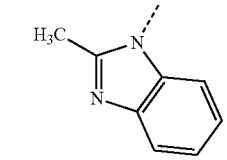 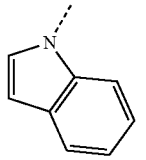 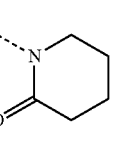

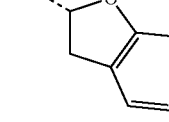  

most preferably $R^8$ represents H or OH;

$R^9$ represents H or $CH_3$, an unsubstituted phenyl; a phenyl substituted by $C(O)CH_3$, COOH, $CH_3$, $OCH_3$, $CF_3$, Cl, F, $NH_2$, C(O)—O—$CH_3$, halogen (especially Cl or F); an unsubstituted naphthyl; an optionally at least mono-substituted heterocyclyl group, selected from:

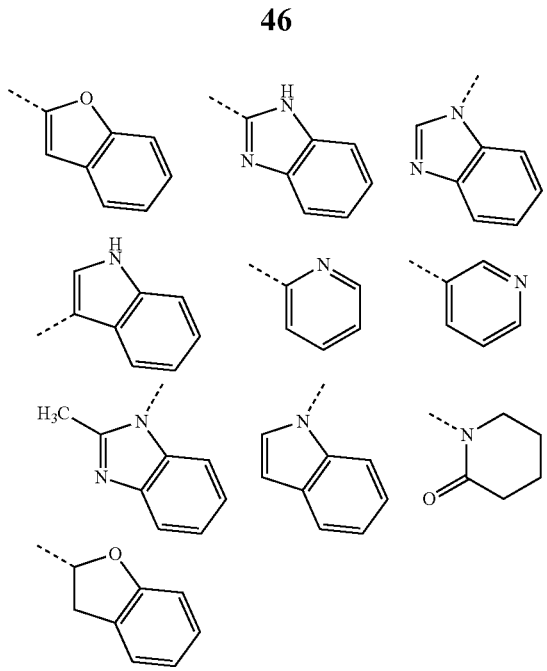

with $R^8$ being a substitute in the ortho, meta or para position if p is 1 or in 2- or 3-position if p is 0.

Another very preferred embodiment of the invention are compounds according to general formula (IA), wherein $R^8$ and $R^9$, binding to the same C-atom in the ring, form together with this C-atom in the ring an optionally at least mono-substituted mono- or polycyclic ring system, preferably leading together with the substituted heterocycle according to formula 1B to spirocyclic structures selected from:

A (if p is 1)

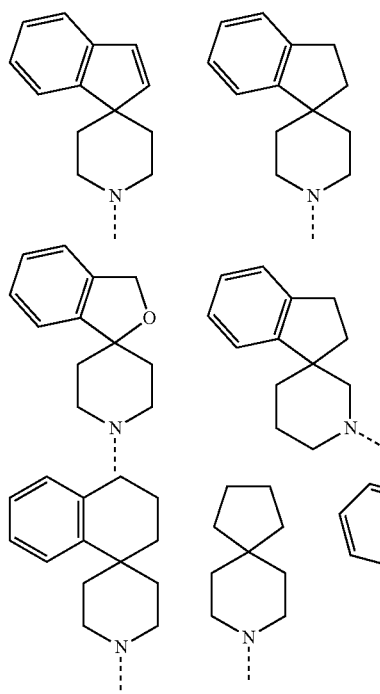

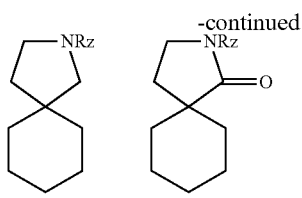

or B if p is 0

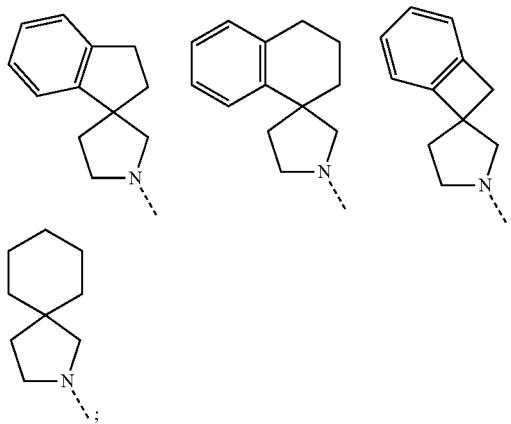

optionally at least mono-substituted, with Rz being preferably a substituted phenyl, an unsubstituted phenyl, a benzyl or an alkyl.

Another very preferred embodiment of the invention are compounds according to general formula (IA), wherein
$R^8$ and $R^9$, binding to different adjacent ring C-Atoms, form together with these C-atom in the ring an optionally at least mono-substituted mono- or polycyclic ring system,
preferably leading together with the substituted heterocycle to the following structures (if p is 1 or 0):

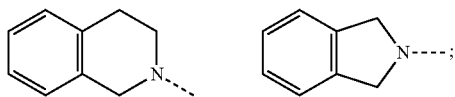

optionally at least mono-substituted, most preferably on the aromatic ring.

Highly preferred compounds according to the invention are compounds selected from
4-phenyl-1-(2-(4,5,6,7-tetrahydrobenzo[b]thiophen-4-yl)ethyl)piperidine.
4-phenyl-1-(2-(4,5,6,7-tetrahydrobenzo[b]thien-4-yl)ethyl)piperidine oxalate.
(E)-N-benzyl-2-(6,7-dihydrobenzo[b]thien-4(5H)-ylidene)-N-methylethanamine.
(E)-N-benzyl-2-(6,7-dihydrobenzo[b]thien-4(5H)-ylidene)-N-methylethanamine oxalate.
(E)-1-(2-(6,7-dihydrobenzo[b]thien-4(5H)-ylidene)ethyl)-4-phenylpiperidine.
(E)-1-(2-(6,7-dihydrobenzo[b]thien-4(5H)-ylidene)ethyl)-4-phenylpiperidine oxalate.
(E)-N-(2-(6,7-dihydrobenzo[b]thien-4(5H)-ylidene)ethyl)-N-methyl-2-phenylethanamine.
(E)-N-(2-(6,7-dihydrobenzo[b]thien-4(5H)-ylidene)ethyl)-N-methyl-2-phenylethanamine oxalate.
(E)-1-(2-(6,7-dihydrobenzo[b]thien-4(5H)-ylidene)ethyl)piperidine.
(E)-1-(2-(6,7-dihydrobenzo[b]thien-4(5H)-ylidene)ethyl)piperidine oxalate.
(E)-1-(2-(6,7-dihydrobenzo[b]thien-4(5H)-ylidene)ethyl)-4-methylpiperidine.
(E)-1-(2-(6,7-dihydrobenzo[b]thien-4(5H)-ylidene)ethyl)-4-methylpiperidine oxalate.
(E)-4-(2-(6,7-dihydrobenzo[b]thien-4(5H)-ylidene)ethyl)morpholine.
(E)-4-(2-(6,7-dihydrobenzo[b]thien-4(5H)-ylidene)ethyl)morpholine oxalate.
4-(2-[spiro[isobenzofuran-1(3H), 4'-piperidin]-1'-yl]-ethyl)-4,5,6,7-tetrahydrobenzo[b]thiophene.
4-(2-[spiro[isobenzofuran-1(3H), 4'-piperidin]-1'-yl]-ethyl)-4,5,6,7-tetrahydrobenzo[b]thiophene oxalate.
4-phenyl-1-(2-(4,5,6,7-tetrahydrobenzo[b]thien-4-yl)ethyl)piperidin-4-ol.
4-phenyl-1-(2-(4,5,6,7-tetrahydrobenzo[b]thien-4-yl)ethyl)piperidin-4-ol oxalate.
4-(4-chlorophenyl)-1-(2-(4,5,6,7-tetrahydrobenzo[b]thien-4-yl)ethyl)piperidin-4-ol.
4-(4-chlorophenyl)-1-(2-(4,5,6,7-tetrahydrobenzo[b]thien-4-yl)ethyl)piperidin-4-ol oxalate.
2-(2-(4,5,6,7-tetrahydrobenzo[b]thien-4-yl)ethyl)isoindoline.
2-(2-(4,5,6,7-tetrahydrobenzo[b]thien-4-yl)ethyl)isoindoline oxalate.
N-benzyl-N-methyl-2-(4,5,6,7-tetrahydrobenzo[b]thien-4-yl)ethanamine.
N-benzyl-N-methyl-2-(4,5,6,7-tetrahydrobenzo[b]thien-4-yl)ethanamine oxalate.
1-(2-(4,5,6,7-tetrahydrobenzo[b]thiophen-4-yl)ethyl)-4-(4-(trifluoromethyl)phenyl)piperidine.
1-(2-(4,5,6,7-tetrahydrobenzo[b]thiophen-4-yl)ethyl)-4-(4-(trifluoromethyl)phenyl)piperidine oxalate.
1-(2-(4,5,6,7-tetrahydrobenzo[b]thiophen-4-yl)ethyl)-4-o-tolylpiperidine.
1-(2-(4,5,6,7-tetrahydrobenzo[b]thiophen-4-yl)ethyl)-4-o-tolylpiperidine oxalate.
4-(3-fluorophenyl)-1-(2-(4,5,6,7-tetrahydrobenzo[b]thiophen-4-yl)ethyl)piperidine.
4-(3-fluorophenyl)-1-(2-(4,5,6,7-tetrahydrobenzo[b]thiophen-4-yl)ethyl)piperidine oxalate.
4-(naphthalen-1-yl)-1-(2-(4,5,6,7-tetrahydrobenzo[b]thiophen-4-yl)ethyl)piperidine.
4-(naphthalen-1-yl)-1-(2-(4,5,6,7-tetrahydrobenzo[b]thiophen-4-yl)ethyl)piperidine oxalate.
4-(4-chlorophenyl)-1-(2-(4,5,6,7-tetrahydrobenzo[b]thiophen-4-yl)ethyl)piperidine.
4-(4-chlorophenyl)-1-(2-(4,5,6,7-tetrahydrobenzo[b]thiophen-4-yl)ethyl)piperidine oxalate.
4-(2-methoxyphenyl)-1-(2-(4,5,6,7-tetrahydrobenzo[b]thiophen-4-yl)ethyl)piperidine.
4-(2-methoxyphenyl)-1-(2-(4,5,6,7-tetrahydrobenzo[b]thiophen-4-yl)ethyl)piperidine oxalate.
1-(2-(4,5,6,7-tetrahydrobenzo[b]thiophen-4-yl)ethyl)-4-p-tolylpiperidine.
1-(2-(4,5,6,7-tetrahydrobenzo[b]thiophen-4-yl)ethyl)-4-p-tolylpiperidine oxalate.
4-(2-(2,3-dihydrospiro[1H-indene-1,4'-piperidin]-1'-yl)ethyl)-4,5,6,7-tetrahydrobenzo[b]thiophene.
4-(2-(2,3-dihydrospiro[1H-indene-1,4'-piperidin]-1'-yl)ethyl)-4,5,6,7-tetrahydrobenzo[b]thiophene oxalate.
4-(3-chlorophenyl)-1-(2-(4,5,6,7-tetrahydrobenzo[b]thiophen-4-yl)ethyl)piperidine.

4-(3-chlorophenyl)-1-(2-(4,5,6,7-tetrahydrobenzo[b]thiophen-4-yl)ethyl)piperidine oxalate.
4-(3-methoxyphenyl)-1-(2-(4,5,6,7-tetrahydrobenzo[b]thiophen-4-yl)ethyl)piperidine.
4-(3-methoxyphenyl)-1-(2-(4,5,6,7-tetrahydrobenzo[b]thiophen-4-yl)ethyl)piperidine oxalate.
4-(4-fluorophenyl)-1-(2-(4,5,6,7-tetrahydrobenzo[b]thiophen-4-yl)ethyl)piperidine.
4-(4-fluorophenyl)-1-(2-(4,5,6,7-tetrahydrobenzo[b]thiophen-4-yl)ethyl)piperidine oxalate.
4-(3,5-bis(trifluoromethyl)phenyl)-1-(2-(4,5,6,7-tetrahydrobenzo[b]thiophen-4-yl)ethyl)piperidine.
4-(3,5-bis(trifluoromethyl)phenyl)-1-(2-(4,5,6,7-tetrahydrobenzo[b]thiophen-4-yl)ethyl)piperidine oxalate.
4-(naphthalen-2-yl)-1-(2-(4,5,6,7-tetrahydrobenzo[b]thiophen-4-yl)ethyl)piperidine.
4-(naphthalen-2-yl)-1-(2-(4,5,6,7-tetrahydrobenzo[b]thiophen-4-yl)ethyl)piperidine oxalate.
4-(benzofuran-2-yl)-1-(2-(4,5,6,7-tetrahydrobenzo[b]thiophen-4-yl)ethyl)piperidine.
4-(benzofuran-2-yl)-1-(2-(4,5,6,7-tetrahydrobenzo[b]thiophen-4-yl)ethyl)piperidine oxalate.
4-(2-fluorophenyl)-1-(2-(4,5,6,7-tetrahydrobenzo[b]thiophen-4-yl)ethyl)piperidine.
4-(2-fluorophenyl)-1-(2-(4,5,6,7-tetrahydrobenzo[b]thiophen-4-yl)ethyl)piperidine oxalate.
2-phenyl-1-(2-(4,5,6,7-tetrahydrobenzo[b]thiophen-4-yl)ethyl)piperidine.
4-(benzo[b]thiophen-3-yl)-1-(2-(4,5,6,7-tetrahydrobenzo[b]thiophen-4-yl)ethyl)piperidine
4-(benzo[b]thiophen-3-yl)-1-(2-(4,5,6,7-tetrahydrobenzo[b]thiophen-4-yl)ethyl)piperidine oxalate.
2-(1-(2-(4,5,6,7-tetrahydrobenzo[b]thiophen-4-yl)ethyl)piperidin-4-yl)-1H-benzo[d]imidazole.
2-(1-(2-(4,5,6,7-tetrahydrobenzo[b]thiophen-4-yl)ethyl)piperidin-4-yl)-1H-benzo[d]imidazole oxalate.
2-methyl-1-(1-(2-(4,5,6,7-tetrahydrobenzo[b]thiophen-4-yl)ethyl)piperidin-4-yl)-1H-benzo[d]imidazole.
2-methyl-1-(1-(2-(4,5,6,7-tetrahydrobenzo[b]thiophen-4-yl)ethyl)piperidin-4-yl)-1H-benzo[d]imidazole oxalate.
4-(4-methoxyphenyl)-1-(2-(4,5,6,7-tetrahydrobenzo[b]thiophen-4-yl)ethyl)piperidine.
4-(4-methoxyphenyl)-1-(2-(4,5,6,7-tetrahydrobenzo[b]thiophen-4-yl)ethyl)piperidine oxalate.
2-Methyl-8-[2-(4,5,6,7-tetrahydrobenzo[b]thiophen-4-yl)-ethyl]-2,8-diazaspiro[4.5]decan-1-one.
2-Methyl-8-[2-(4,5,6,7-tetrahydrobenzo[b]thiophen-4-yl)-ethyl]-2,8-diazaspiro[4.5]decan-1-one oxalate
1'-(2-(4,5,6,7-tetrahydrobenzo[b]thiophen-4-yl)ethyl)-spiro(isobenzofuran-1(3H), 4'-piperidin)-3-one.
1'-(2-(4,5,6,7-tetrahydrobenzo[b]thiophen-4-yl)ethyl)-spiro(isobenzofuran-1(3H), 4'-piperidin)-3-one oxalate.
2-(4-Chlorophenyl)-8-[2-(4,5,6,7-tetrahydrobenzo[b]thiophen-4-yl)-ethyl]-2,8-diazaspiro[4.5]decan-1-one.
2-(4-Chlorophenyl)-8-[2-(4,5,6,7-tetrahydrobenzo[b]thiophen-4-yl)-ethyl]-2,8-diazaspiro[4.5]decan-1-one oxalate.
8-[2-(4,5,6,7-Tetrahydrobenzo[b]thiophen-4-yl)-ethyl]-2,8-diazaspiro[4.5]decan-1-one.
8-[2-(4,5,6,7-Tetrahydrobenzo[b]thiophen-4-yl)-ethyl]-2,8-diazaspiro[4.5]decan-1-one oxalate
4-(2-(spiro[1H-indene-1,4'-piperidin]-1'-yl)ethyl)-4,5,6,7-tetrahydrobenzo[b]thiophene.
4-(2-(spiro[1H-indene-1,4'-piperidin]-1'-yl)ethyl)-4,5,6,7-tetrahydrobenzo[b]thiophene oxalate.
7-methoxy-2-(2-(4,5,6,7-tetrahydrobenzo[b]thiophen-4-yl)ethyl)-1,2,3,4-tetrahydroisoquinoline.
7-methoxy-2-(2-(4,5,6,7-tetrahydrobenzo[b]thiophen-4-yl)ethyl)-1,2,3,4-tetrahydroisoquinoline oxalate.
5,7-dichloro-2-(2-(4,5,6,7-tetrahydrobenzo[b]thiophen-4-yl)ethyl)-1,2,3,4-tetrahydroisoquinoline.
5,7-dichloro-2-(2-(4,5,6,7-tetrahydrobenzo[b]thiophen-4-yl)ethyl)-1,2,3,4-tetrahydroisoquinoline oxalate.
1-(1-(2-(4,5,6,7-tetrahydrobenzo[b]thiophen-4-yl)ethyl)piperidin-4-yl)-1H-indole.
1-(1-(2-(4,5,6,7-tetrahydrobenzo[b]thiophen-4-yl)ethyl)piperidin-4-yl)-1H-indole oxalate
2-tert-butyl-8-[2-(4,5,6,7-tetrahydrobenzo[b]thiophen-4-yl)-ethyl]-2,8-diazaspiro[4.5]decan-1-one.
2-tert-butyl-8-[2-(4,5,6,7-tetrahydrobenzo[b]thiophen-4-yl)-ethyl]-2,8-diazaspiro[4.5]decan-1-one oxalate.
2-benzyl-8-[2-(4,5,6,7-tetrahydrobenzo[b]thiophen-4-yl)-ethyl]-2,8-diazaspiro[4.5]decan-1-one.
2-benzyl-8-[2-(4,5,6,7-tetrahydrobenzo[b]thiophen-4-yl)-ethyl]-2,8-diazaspiro[4.5]decan-1-one oxalate.
2-(4-Methoxyphenyl)-8-[2-(4,5,6,7-tetrahydrobenzo[b]thiophen-4-yl)-ethyl]-2,8-diazaspiro[4.5]decan-1-one.
2-(4-Methoxyphenyl)-8-[2-(4,5,6,7-tetrahydrobenzo[b]thiophen-4-yl)-ethyl]-2,8-diazaspiro[4.5]decan-1-one oxalate.
2-phenyl-8-[2-(4,5,6,7-tetrahydrobenzo[b]thiophen-4-yl)-ethyl]-2,8-diazaspiro[4.5]decan-1-one.
2-phenyl-8-[2-(4,5,6,7-tetrahydrobenzo[b]thiophen-4-yl)-ethyl]-2,8-diazaspiro[4.5]decan-1-one oxalate.
2-(4-trifluoromethylphenyl)-8-[2-(4,5,6,7-tetrahydro-benzo[b]thiophen-4-yl)-ethyl]-2,8-diazaspiro[4.5]decan-1-one.
2-(4-trifluoromethylphenyl)-8-[2-(4,5,6,7-tetrahydrobenzo[b]thiophen-4-yl)-ethyl]-2,8-diazaspiro[4.5]decan-1-one oxalate.
5-bromo-2-(2-(4,5,6,7-tetrahydrobenzo[b]thiophen-4-yl)ethyl)-1,2,3,4-tetrahydroisoquinoline.
5-bromo-2-(2-(4,5,6,7-tetrahydrobenzo[b]thiophen-4-yl)ethyl)-1,2,3,4-tetrahydroisoquinoline oxalate.
2-(2-(4,5,6,7-tetrahydrobenzo[b]thiophen-4-yl)ethyl)-1,2,3,4-tetrahydroisoquinoline-7-carbonitrile
2-(2-(4,5,6,7-tetrahydrobenzo[b]thiophen-4-yl)ethyl)-1,2,3,4-tetrahydroisoquinoline-7-carbonitrile oxalate.
2-(4-Fluorophenyl)-8-[2-(4,5,6,7-tetrahydrobenzo[b]thiophen-4-yl)-ethyl]-2,8-diazaspiro[4.5]decan-1-one
2-(4-Fluorophenyl)-8-[2-(4,5,6,7-tetrahydrobenzo[b]thiophen-4-yl)-ethyl]-2,8-diazaspiro[4.5]decan-1-one oxalate;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another aspect of the invention refers to a process for the preparation of a compound of formula (I) according to the invention, or a salt, isomer or solvate thereof, which comprises the condensation of a compound of Formula (II):

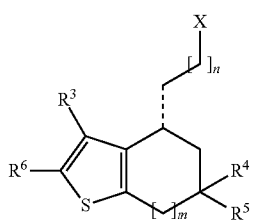
(II)

in which $R_3$, $R_4$, $R_5$ and $R_6$ as well as m and n are as defined above and X being a leaving group, with a compound of Formula (III):

(III)

in which $R^1$ and $R_2$ are as defined above.

In general the processes are described below in the experimental part. The starting materials are commercially available or can be prepared by conventional methods.

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention or a pharmaceutically acceptable salt, prodrug, isomer or solvate thereof, and a pharmaceutically acceptable carrier, adjuvant or vehicle. The present invention thus provides pharmaceutical compositions comprising a compound of this invention, or a pharmaceutically acceptable salt, derivative, prodrug or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound according to the invention in the manufacture of a medicament.

Another aspect of the invention refers to the use of a compound according to the invention in the manufacture of a medicament for the treatment or prophylaxis of a sigma receptor mediated disease or condition. A preferred embodiment of this is this use wherein the disease is diarrhea, lipoprotein disorders, metabolic syndrome, treatment of elevated triglyceride levels, chylomicronemia, hyperlipoproteinemia; hyperlipidemia, especially mixed hyperlipidemia; hypercholesterolemia, dysbetalipoproteinemia, hypertriglyceridemia including both the sporadic and familial disorder (inherited hypertriglyceridemia), migraine, obesity, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine, tardive diskinesia, ischemic stroke, epilepsy, stroke, depression, stress, psychotic condition, schizophrenia; inflammation, autoimmune diseases or cancer.

A preferred embodiment of this is this use wherein the disease is pain, especially neuropathic pain, inflammatory pain or other pain conditions, allodynia and/or hyperalgesia, especially mechanical allodynia.

Another aspect of the invention refers to the use of a compound according to the invention as pharmacological tool or as anxiolytic or immunosuppressant.

The term "pharmacological tool" refers to the property of compounds of the invention through which they are particularly selective ligands for Sigma receptors which implies that compound of formula I, described in this invention, can be used as a model for testing other compounds as Sigma ligands, ex. a radiactive ligands being replaced, and can also be used for modeling physiological actions related to Sigma receptors.

Another aspect of this invention relates to a method of treating or preventing a sigma receptor mediated disease which method comprises administering to a patient in need of such a treatment a therapeutically effective amount of a compound as above defined or a pharmaceutical composition thereof. Among the sigma mediated diseases that can be treated are diarrhea, lipoprotein disorders, metabolic syndrome, treatment of elevated triglyceride levels, chylomicronemia, hyperlipoproteinemia; hyperlipidemia, especially mixed hyperlipidemia; hypercholesterolemia, dysbetalipoproteinemia, hypertriglyceridemia including both the sporadic and familial disorder (inherited hypertriglyceridemia), migraine, obesity, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine, tardive diskinesia, ischemic stroke, epilepsy, stroke, depression, stress, pain, especially neuropathic pain, inflammatory pain or other pain conditions, allodynia and/or hyperalgesia, especially mechanical allodynia, psychotic condition, schizophrenia; inflammation, autoimmune diseases or cancer; disorders of food ingestion, the regulation of appetite, for the reduction, increase or maintenance of body weight, for the prophylaxis and/or treatment of obesity, bulimia, anorexia, cachexia or type II diabetes, preferably type II diabetes caused by obesity. The compounds of the invention can also be employed as pharmacological tool or as anxiolytic or immunosuppressant.

The present invention is illustrated below with the aid of examples. These illustrations are given solely by way of example and do not limit the general spirit of the present invention.

EXAMPLES

General Synthesis

Method A:

The compounds of formula (I) defined above can be obtained by available synthetic procedures. For example, they can be prepared according to the following scheme I:

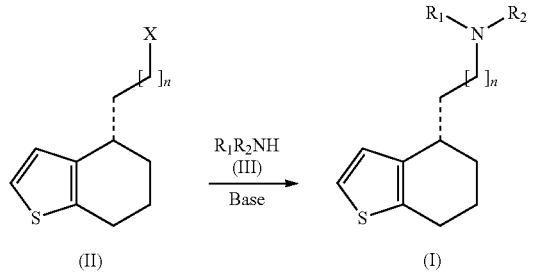

According to the Method A the compounds of formula (I) are prepared by coupling of a compound of Formula (II), in which A, and n are as defined above in formula (I) and X is a leaving group, preferably chlorine or bromine with a compound of formula (III), HNR$_1$R$_2$, in which R$_1$ and R$_2$ are as defined above in formula (I).

The reaction of compounds of formula (II) and (III) is preferably carried out in an aprotic solvent, but not limited to, such as N,N-dimethylformamide (DMF) in the presence of an inorganic base, such as K$_2$CO$_3$, or an organic base, such as triethylamine or ethyldiisopropylamine, and at an appropriated temperature between room temperature and the reflux temperature of the solvent.

Compounds of formula (II) are also commercially available or can be prepared by methods well known in the literature. See, Berardi, F.; Giudice, G.; Perrone, R.; Tortorella, V.; Govoni, S.; Lucchi, L. *J. Med, Chem.* 1996, 39 4255-4260 and Christoph, J.; Frotscher, M.; Dannhardt, G.; Hartmann, R. *J. Med, Chem.* 2000, 43 1841-1851.

Method B:

The compounds of formula (I) can also be obtained according to the synthetic process described by scheme II:

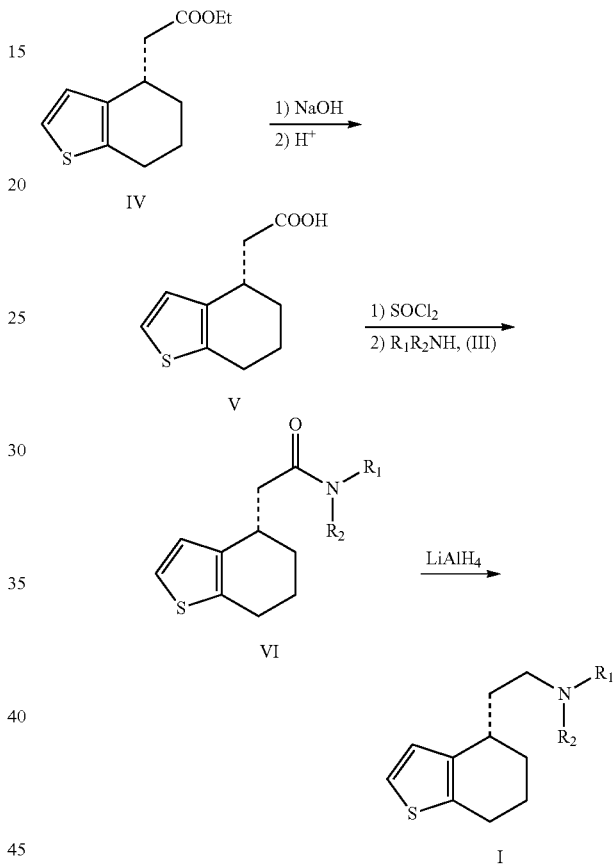

Following Method B, the compounds of formula (V) are prepared from the compounds of formula (IV) by hydrolysis of the ester group with a base such as NaOH, KOH or LiOH in a mixture of water and an alcohol such as methanol or ethanol, and at an appropriated temperature between room temperature and the reflux temperature of the solvent.

Following Method B, the compounds of formula (VI) are prepared by reaction of the compounds of formula (V) with thionyl chloride and subsequent treatment with amines of formula R$_1$R$_2$NH (III) in an inert solvent such as methylene chloride at a temperature that can be between 0° C. and room temperature. The compounds of formula (VI) are prepared by reaction of the compounds of formula (V) with alkyl chloroformate, such as methyl chloroformate, ethyl chloroformate, isoprenyl chloroformate, or isobutyl chloroformate, in the presence of a base such as triethylamine, ethyldiisopropylamine or N-methylmorpholine, and subsequent treatment with amines of the formula R$_1$R$_2$NH (III), in an inert solvent such as methylene chloride, tetrahydrofuran or N,N-dimethylformamide, and at an appropriated temperature between 0°

C. and room temperature. The compounds of formula (VI) can also be prepared from the compounds of formula (V) and the amines of formula $R_1R_2NH$ (III) in the presence of reactives which activate carbonyl groups such as N,N'-dicyclohexylcarbodiimide, 1-(3-dimethylaminopropyl)-3-ethylcarbodiimide hydrochloride or diisopropylcarbodiimide. This reaction can also be carried out using the carbodiimides in the presence of 1-benzotriazole or N-hydroxysuccinimide. The compounds of formula (VI) can also be prepared from the compounds of formula (V) and the amines of formula $R_1R_2NH$ (III) in the presence of N,N'-carbonyldiimidazole.

Following Method B, the compounds of formula (I) are prepared from the compounds of formula (VI) by reaction with reducing agents such as lithium aluminum hydride.

Example 1

Synthesis of 4-phenyl-1-(2-(4,5,6,7-tetrahydrobenzo[b]thiophen-4-yl)ethyl)piperidine Step 1: Synthesis of 4-(2-chloroethyl)-4,5,6,7-tetrahydrobenzo[b]thiophene

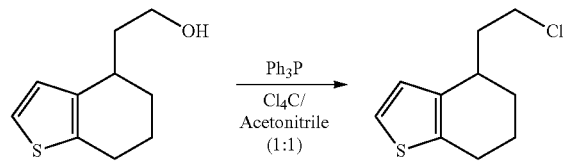

Triphenylphosphine (3.94 g, 15 mmol) is added to a solution of 2-(4,5,6,7-tetrahydrobenzo[b]thiophen-4-yl)ethanol (2.74 g, 15 mmol) in $Cl_4C$/Acetonitrile 1:1 (20 mL) at room temperature and the mixture is maintained under stirring for 3 hours monitoring the reaction by TLC. The solution is concentrated to half the volume at reduced pressure, $CH_2Cl_2$ is added and washed with water. The organic phase is separated and evaporated to dryness. The crude is treated with diethyl ether and the precipitate is filtered. The diethyl ether is evaporated to dryness, and the resulting crude is purified by column chromatography, giving 4-(2-chloroethyl)-4,5,6,7-tetrahydrobenzo[b]thiophene (1.7 g, 8.4 mmol, 56%, oil). $^1$H NMR (300 MHz, $CDCl_3$): δ 1.54 (m, 1H), 1.79 (m, 1H), 1.92 (m, 3H), 2.20 (m, 1H), 2.77 (m, 2H), 3.00 (m, 1H), 3.64 (m, 2H), 6.86 (d, J=5.2 Hz, 1H), 7.06 (d, J=5.2 Hz, 1H).

Step 2: 4-phenyl-1-(2-(4,5,6,7-tetrahydrobenzo[b]thien-4-yl)ethyl)piperidine

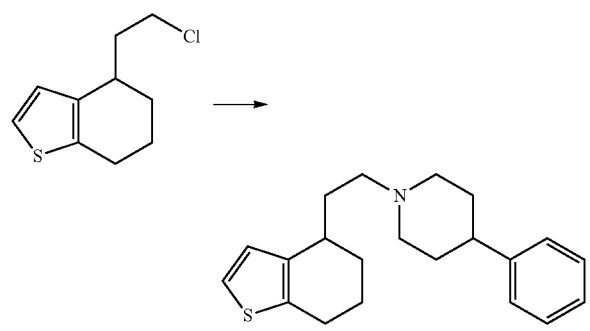

A mixture of 4-(2-chloroethyl)-4,5,6,7-tetrahydrobenzo[b]thiophene (0.25 g, 1.24 mmol), 4-phenylpiperidine hydrochloride (0.25 g, 1.25 mmol), $K_2CO_3$ (0.40 g, 2.89 mmol) and a catalytic amount of NaI in DMF (5 mL) is heated to 110° C. overnight. The solvent is removed at reduced pressure, diethyl ether is added to the residue and washed with water. The organic phase is dried and evaporated at reduced pressure and the resulting crude is purified by column chromatography, giving 4-phenyl-1-(2-(4,5,6,7-tetrahydrobenzo[b]thien-4-yl)ethyl)piperidine (0.24 g, 0.74 mmol, 59%, oil). $^1$H NMR (300 MHz, $CDCl_3$): δ 1.54 (m, 1H), 1.70-2.18 (m, 11H), 2.51 (m, 3H), 2.76 (m, 3H), 3.12 (m, 2H), 6.88 (d, J=5.2 Hz, 1H), 7.04 (d, J=5.2 Hz, 1H), 7.18-7.32 (m, 5H).

Example 2

Synthesis of 4-phenyl-1-(2-(4,5,6,7-tetrahydrobenzo[b]thien-4-yl)ethyl)piperidine oxalate

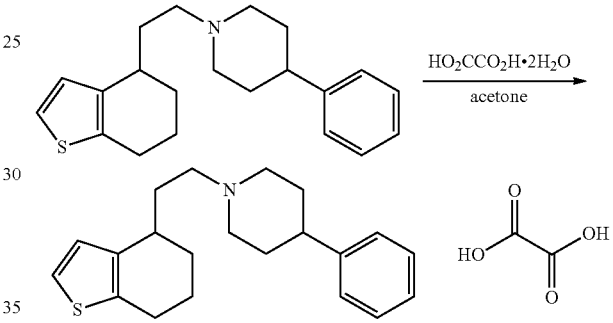

$HO_2CCO_2H\cdot 2H_2O$ (0.10 g, 0.8 mmol) is added to a solution de 4-phenyl-1-(2-(4,5,6,7-tetrahydrobenzo[b]thiophen-4-yl)ethyl)piperidine (0.23 g, 0.70 mmol) in acetone (3 mL) giving 4-phenyl-1-(2-(4,5,6,7-tetrahydrobenzo[b]thien-4-yl)ethyl)piperidine (0.25 g, 0.60 mmol, 86%, m.p.=176-179° C., white solid).

Example 3

Synthesis of (E)-N-benzyl-2-(6,7-dihydrobenzo[b]thien-4(5H)-ylidene)-N-methylethanamine Step 1: Synthesis of (E)-N-benzyl-2-(6,7-dihydrobenzo[b]thien-4(5H)-ylidene)-N-methylacetamide

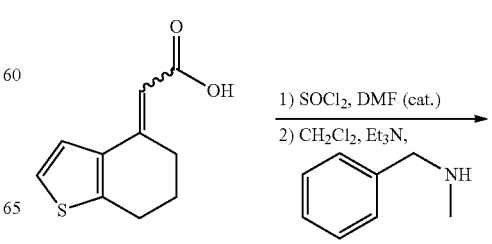

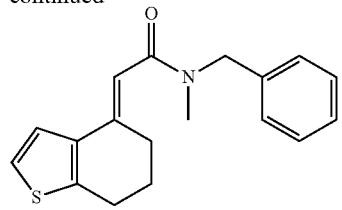

A solution of a mixture E/Z of 2-(6,7-dihydrobenzo[b]thiophen-4(5H)-ylidene)acetic acid (0.38 g, 1.96 mmol) in thionyl chloride (3 mL) and a catalytic amount of DMF is refluxed for 5 min. The solvent is evaporated at reduced pressure and the residue is slowly added to a solution of N-methyl-N-benzylamine (0.24 g, 1.96 mmol) and triethylamine (0.5 mL) in dry CH$_2$Cl$_2$ (15 mL) cooled in an ice bath and stirred at room temperature monitoring the reaction by TLC. The solution is washed with water and the organic phase is dried and evaporated under reduced pressure, and the resulting crude is purified by column chromatography, giving (E)-N-benzyl-2-(6,7-dihydrobenzo[b]thien-4(5H)-ylidene)-N-methylacetamide (0.35 g, 1.17 mmol, 60%, viscous oil). $^1$H NMR (300 MHz, CDCl$_3$): δ 1.95 (m, 2H), 2.87 (m, 4H), 3.00 (s, 3H), 4.65 (s, 2H), 6.34 (s, 1H), 7.04 (d, J=5.3 Hz, 1H), 7.09 (d, J=5.3 Hz, 1H), 7.23-7.38 (m, 5H).

Step 2: Synthesis of (E)-N-benzyl-2-(6,7-dihydrobenzo[b]thien-4(5H)-ylidene)-N-methylethanamine

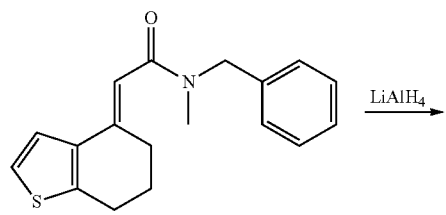

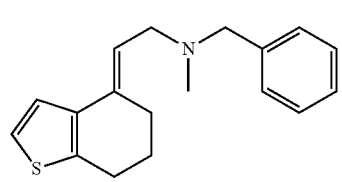

(E)-N-benzyl-2-(6,7-dihydrobenzo[b]thiophen-4(5H)-ylidene)-N-methylacetamide (0.32 g, 1.01 mmol) in THF anh. (5 mL) is added slowly to a suspension of AlLiH$_4$ (0.1 g, 2.63 mmol) in THF anh. (20 mL) cooled in an ice bath and is stirred at room temperature for 1 hour and refluxed for 2 hours. The solution is cooled in an ice bath and some drops of NaOH 10% is added. The mixture is filtered and washed with ethyl acetate. The filtrate is evaporated to dryness and the residue is dissolved in ethyl acetate and washed with water. The organic phase is removed and the resulting crude is purified by column chromatography, giving (E)-N-benzyl-2-(6,7-dihydrobenzo[b]thien-4(5H)-ylidene)-N-methylethanamine (0.25 g, 0.88 mmol, 87%, oil). $^1$H NMR (300 MHz, CDCl$_3$): δ 1.90 (m, 2H), 2.29 (s, 3H), 2.44 (m, 2H), 2.84 (t, J=6.1 Hz, 2H), 3.26 (d, J=7.0 Hz, 2H), 3.62 (s, 2H), 5.94 (t, J=7.0 Hz, 1H), 7.04 (d, J=5.3 Hz, 1H), 7.20 (d, J=5.3 Hz, 1H), 7.25-7.40 (m, 5H).

Example 4

(E)-N-benzyl-2-(6,7-dihydrobenzo[b]thien-4(5H)-ylidene)-N-methylethanamine oxalate

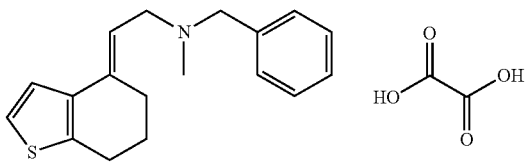 [SMILES: CN(C/C=C1\CCCc2sccc21)Cc1ccccc1 ; O=C(O)C(=O)O]

(m.p.=139-141° C., 82%, white solid).

Example 5

(E)-1-(2-(6,7-dihydrobenzo[b]thien-4(5H)-ylidene)ethyl)-4-phenylpiperidine

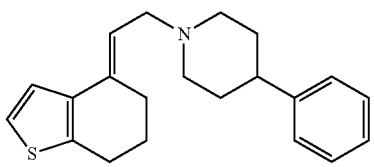 [SMILES: C(/CN1CCC(c2ccccc2)CC1)=C1/CCCc2sccc21]

$^1$H NMR (300 MHz, CDCl$_3$): δ 1.70-1.99 (m, 6H), 2.13 (m, 2H), 2.50 (m, 3H), 2.84 (t, J=6.1 Hz, 2H), 3.15 (m, 2H), 3.23 (d, J=7.2 Hz, 2H), 5.95 (t, J=7.2 Hz, 1H), 7.03 (d, J=5.3 Hz, 1H), 7.16-7.35 (m, 6H). (74%, oil)

Example 6

(E)-1-(2-(6,7-dihydrobenzo[b]thien-4(5H)-ylidene)ethyl)-4-phenylpiperidine oxalate

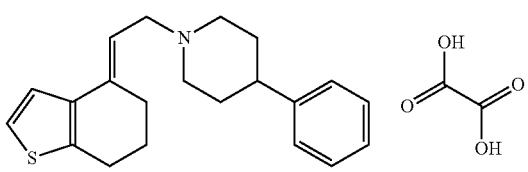

(m.p.=160-163° C., 76%, yellowish solid).

Example 7

(E)-N-(2-(6,7-dihydrobenzo[b]thien-4(5H)-ylidene)ethyl)-N-methyl-2-phenylethanamine

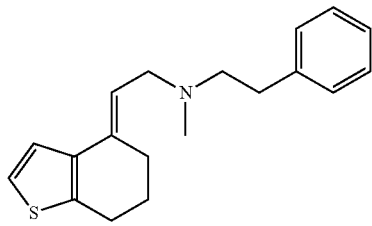 [SMILES: CN(C/C=C1\CCCc2sccc21)CCc1ccccc1]

$^1$H NMR (300 MHz, CDCl$_3$): δ 1.91 (m, 2H), 2.40 (s, 3H), 2.47 (m, 2H), 2.70-2.95 (m, 6H), 3.31 (d, J=7.0 Hz, 2H), 5.89 (t, J=7.0 Hz, 1H), 7.04 (d, J=5.3 Hz, 1H), 7.14-7.33 (m, 6H).

Example 8

(E)-N-(2-(6,7-dihydrobenzo[b]thien-4(5H)-ylidene)ethyl)-N-methyl-2-phenylethanamine oxalate

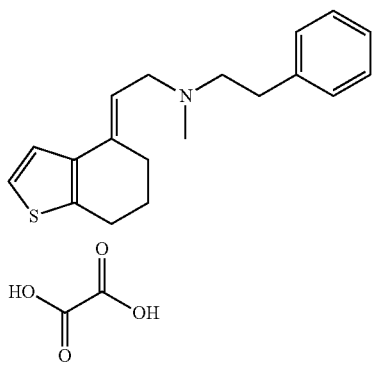

(m.p.=129-130° C., white solid).

Example 9

(E)-1-(2-(6,7-dihydrobenzo[b]thien-4(5H)-ylidene)ethyl)piperidine

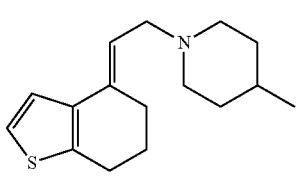 [SMILES: CC1CCN(C/C=C2\CCCc3sccc32)CC1]

$^1$H NMR (300 MHz, CDCl$_3$): δ 1.45 (m, 2H), 1.64 (m, 4H), 1.90 (m, 2H), 2.31-2.62 (m, 6H), 2.83 (t, J=6.1 Hz, 2H), 3.17 (d, J=7.2 Hz, 2H), 5.91 (t, J=7.2 Hz, 1H), 7.02 (d, J=5.3 Hz, 1H), 7.18 (d, J=5.3 Hz, 1H). (74%, oil).

Example 10

(E)-1-(2-(6,7-dihydrobenzo[b]thien-4(5H)-ylidene)ethyl)piperidine oxalate

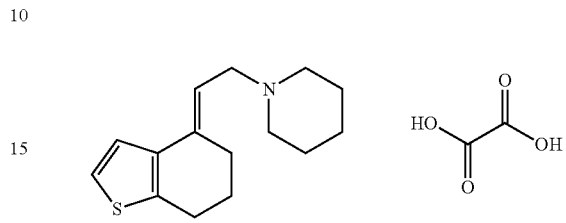

(m.p.=148-150° C., 79%, white solid).

Example 11

(E)-1-(2-(6,7-dihydrobenzo[b]thien-4(5H)-ylidene)ethyl)-4-methylpiperidine

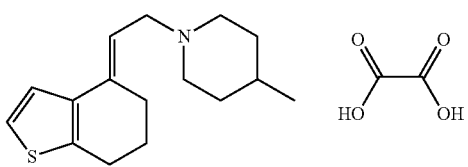 [SMILES: CC1CCN(C/C=C2\CCCc3sccc32)CC1 ; O=C(O)C(=O)O]

$^1$H NMR (300 MHz, CDCl$_3$): δ 0.93 (d, J=6.0 Hz, 3H), 1.20-1.42 (m, 3H), 1.64 (m, 2H), 1.84-2.03 (m, 4H), 2.46 (m, 2H), 2.82 (t, J=6.1 Hz, 2H), 2.97 (m, 2H), 3.16 (d, J=7.1 Hz, 2H), 5.91 (t, J=7.1 Hz, 1H), 7.02 (d, J=5.3 Hz, 1H), 7.18 (d, J=5.3 Hz, 1H). (85%, oil).

Example 12

(E)-1-(2-(6,7-dihydrobenzo[b]thien-4(5H)-ylidene)ethyl)-4-methylpiperidine oxalate (m.p.=139-141° C., 80%, white solid).

Example 13

(E)-4-(2-(6,7-dihydrobenzo[b]thien-4(5H)-ylidene)ethyl)morpholine

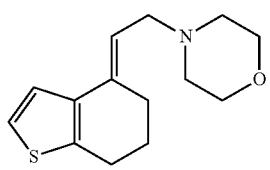 [SMILES: C(/CN1CCOCC1)=C1/CCCc2sccc21]

$^1$H NMR (300 MHz, CDCl$_3$): δ 1.89 (m, 2H), 2.41-2.60 (m, 6H), 2.84 (t, J=6.1 Hz, 2H), 3.18 (d, J=7.2 Hz, 2H), 3.75 (m, 4H), 5.87 (t, J=7.2 Hz, 1H), 7.03 (d, J=5.3 Hz, 1H), 7.17 (d, J=5.3 Hz, 1H). (71%, oil).

Example 14

(E)-4-(2-(6,7-dihydrobenzo[b]thien-4(5H)-ylidene)ethyl)morpholine oxalate

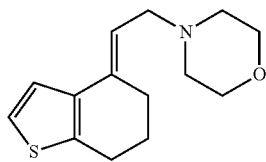

(m.p.=171-174° C., 64%, yellowish solid).

Example 15

4-(2-[spiro[isobenzofuran-1(3H), 4'-piperidin]-1'-yl]-ethyl)-4,5,6,7-tetrahydrobenzo[b]thiophene

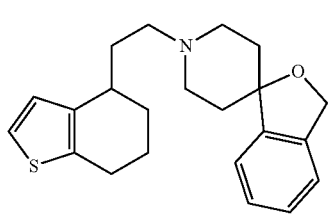 [SMILES: c1ccc2c(c1)COC21CCN(CCC2CCCc3sccc32)CC1]

$^1$H NMR (300 MHz, CDCl$_3$): δ 1.54 (m, 1H), 1.68-2.13 (m, 9H), 2.38-2.61 (m, 4H), 2.76 (m, 3H), 2.94 (m, 2H), 5.07 (s, 2H), 6.80 (d, J=5.2 Hz, 1H), 7.04 (d, J=5.2 Hz, 1H), 7.15 (m, 1H), 7.20 (m, 1H), 7.26 (m, 2H). (48%, oil).

Example 16

4-(2-[spiro[isobenzofuran-1(3H), 4'-piperidin]-1'-yl]ethyl)-4,5,6,7-tetrahydrobenzo[b]thiophene oxalate

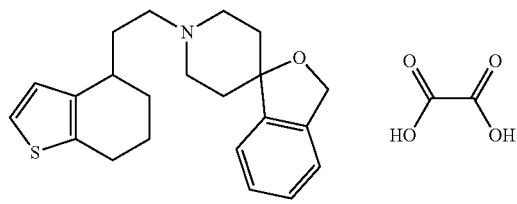 [SMILES: c1ccc2c(c1)COC21CCN(CCC2CCCc3sccc32)CC1 ; O=C(O)C(=O)O]

(m.p.=172-176° C., 45%, white solid).

Example 17

4-phenyl-1-(2-(4,5,6,7-tetrahydrobenzo[b]thien-4-yl)ethyl)piperidin-4-ol

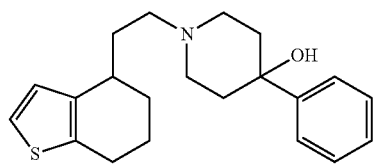 [SMILES: OC1(c2ccccc2)CCN(CCC2CCCc3sccc32)CC1]

$^1$H NMR (300 MHz, CDCl$_3$): δ 1.55 (m, 1H), 1.67-2.08 (m, 7H), 2.22 (m, 2H), 2.43-2.60 (m, 4H), 2.76 (m, 3H), 2.89 (m, 2H), 6.88 (d, J=5.2 Hz, 1H), 7.04 (d, J=5.2 Hz, 1H), 7.26 (m, 1H), 7.36 (m, 2H), 7.52 (m, 2H). (64%, oil).

Example 18

4-phenyl-1-(2-(4,5,6,7-tetrahydrobenzo[b]thien-4-yl)ethyl)piperidin-4-ol oxalate

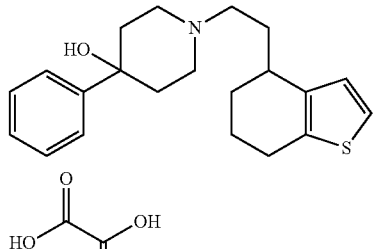

(m.p.=179-170° C., 76%, white solid).

Example 19

4-(4-chlorophenyl)-1-(2-(4,5,6,7-tetrahydrobenzo[b]thien-4-yl)ethyl)piperidin-4-ol

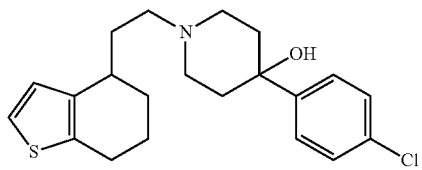

$^{1}$H NMR (300 MHz, CDCl$_{3}$): δ 1.54 (m, 1H), 1.63-1.82 (m, 4H), 1.88-2.06 (m, 3H), 2.17 (m, 2H), 2.40-2.59 (m, 4H), 2.76 (m, 3H), 2.88 (m, 2H), 6.87 (d, J=5.2 Hz, 1H), 7.04 (d, J=5.2 Hz, 1H), 7.31 (d, J=8.7 Hz, 2H), 7.44 (d, J=8.7 Hz, 2H). (56%, oil).

Example 20

4-(4-chlorophenyl)-1-(2-(4,5,6,7-tetrahydrobenzo[b]thien-4-yl)ethyl)piperidin-4-ol oxalate

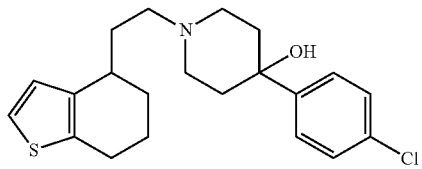 [SMILES: OC1(c2ccc(Cl)cc2)CCN(CCC2CCCc3sccc32)CC1]

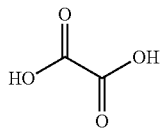

(m.p.=184-185° C., 70%, white solid).

Example 21

2-(2-(4,5,6,7-tetrahydrobenzo[b]thien-4-yl)ethyl)isoindoline

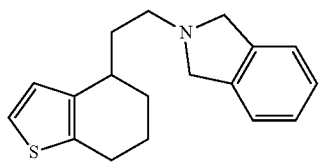 [SMILES: c1ccc2c(c1)CN(CCC1CCCc3sccc31)C2]

(24%, oil)

Example 22

2-(2-(4,5,6,7-tetrahydrobenzo[b]thien-4-yl)ethyl)isoindoline oxalate

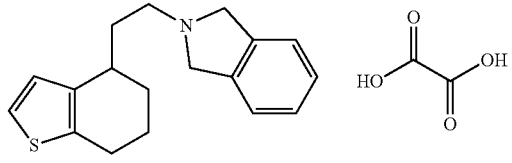

$^{1}$H NMR (300 MHz, CD$_{3}$OD): δ 1.61 (m, 1H), 1.78 (m, 1H), 1.99 (m, 3H), 2.25 (m, 1H), 2.77 (m, 2H), 2.92 (m, 1H), 3.50 (m, 2H), 4.72 (s, 4H), 6.92 (d, J=5.2 Hz, 1H), 7.15 (d, J=5.2 Hz, 1H), 7.40 (s, 4H). (m.p.=203-205° C., 48%, cream-colored solid)

Example 23

N-benzyl-N-methyl-2-(4,5,6,7-tetrahydrobenzo[b]thien-4-yl)ethanamine

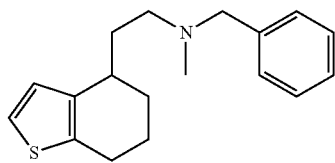

$^{1}$H NMR (300 MHz, CDCl$_{3}$): δ 1.48 (m, 1H), 1.61-1.79 (m, 2H), 1.83-1.95 (m, 2H), 2.00 (m, 1H), 2.23 (s, 3H), 2.44-2.58 (m, 2H), 2.74 (m, 2H), 2.81 (m, 1H), 3.49 (d, J=13.0 Hz, 1H), 3.59 (d, J=13.0 Hz, 1H), 6.83 (d, J=5.2 Hz, 1H), 7.03 (d, J=5.2 Hz, 1H), 7.23-7.35 (m, 5H). (54%, oil).

Example 24

N-benzyl-N-methyl-2-(4,5,6,7-tetrahydrobenzo[b]thien-4-yl)ethanamine oxalate

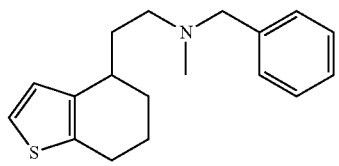 [SMILES: CN(CCC1CCCc2sccc21)Cc1ccccc1]

(m.p.=168-171° C., 65%, white solid).

Example 25

1-(2-(4,5,6,7-tetrahydrobenzo[b]thiophen-4-yl)ethyl)-4-(4-(trifluoromethyl)phenyl)piperidine

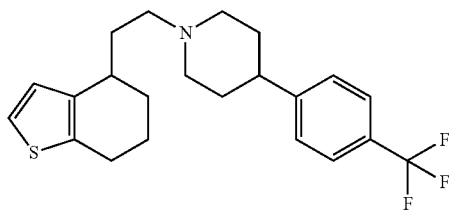 [SMILES: FC(F)(F)c1ccc(C2CCN(CCC3CCCc4sccc43)CC2)cc1]

$^1$H NMR (300 MHz, CDCl$_3$): δ 1.56 (m, 1H), 1.66-2.18 (m, 11H), 2.44-2.64 (m, 3H), 2.77 (m, 3H), 3.12 (m, 2H), 6.89 (d, J=5.1 Hz, 1H), 7.06 (d, J=5.1 Hz, 1H), 7.34 (d, J=8.2 Hz, 2H), 7.56 (d, J=8.2 Hz, 2H).

(206 mg, 0.52 mmol, 87%, oil).

Example 26

1-(2-(4,5,6,7-tetrahydrobenzo[b]thiophen-4-yl)ethyl)-4-(4-(trifluoromethyl)phenyl)piperidine oxalate

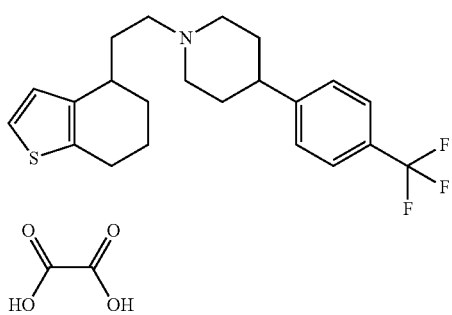

(96 mg, 0.19 mmol, 38%, m.p.=180-182° C., white solid).

Example 27

1-(2-(4,5,6,7-tetrahydrobenzo[b]thiophen-4-yl)ethyl)-4-o-tolylpiperidine

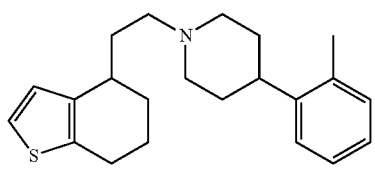 [SMILES: Cc1ccccc1C1CCN(CCC2CCCc3sccc32)CC1]

$^1$H NMR (300 MHz, CDCl$_3$): δ 1.55 (m, 1H), 1.66-2.16 (m, 11H), 2.34 (s, 3H), 2.50 (t, J=8.0 Hz, 2H), 2.76 (m, 4H), 3.12 (m, 2H), 6.89 (d, J=5.2 Hz, 1H), 7.05 (d, J=5.2 Hz, 1H), 7.07-7.20 (m, 3H), 7.25 (m, 1H)

(160 mg, 0.47 mmol, 78%, oil). .

Example 28

1-(2-(4,5,6,7-tetrahydrobenzo[b]thiophen-4-yl)ethyl)-4-o-tolylpiperidine oxalate

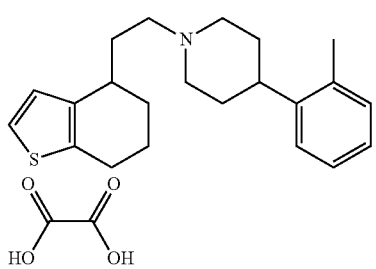

(97 mg, 0.23 mmol, 49%, m.p.=188-190° C., white solid).

Example 29

4-(3-fluorophenyl)-1-(2-(4,5,6,7-tetrahydrobenzo[b]thiophen-4-yl)ethyl)piperidine

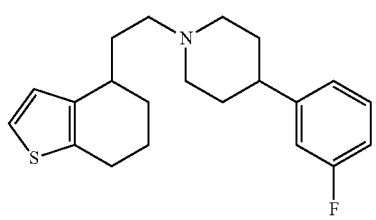

$^1$H NMR (300 MHz, CDCl$_3$): δ 1.54 (m, 1H), 1.64-2.12 (m, 11H), 2.47 (m, 3H), 2.76 (m, 3H), 3.09 (m, 2H), 6.85-6.95 (m, 3H), 7.00 (d, J=7.8 Hz, 1H), 7.04 (d, J=5.2 Hz, 1H), 7.24 (m, 1H).

(oil).

Example 30

4-(3-fluorophenyl)-1-(2-(4,5,6,7-tetrahydrobenzo[b]thiophen-4-yl)ethyl)piperidine oxalate

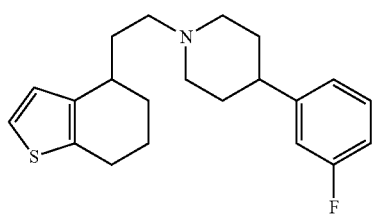 [SMILES: Fc1cccc(C2CCN(CCC3CCCc4sccc43)CC2)c1]

(126 mg, 0.29 mmol, m.p.=203-204° C., white solid).

Example 31

4-(naphthalen-1-yl)-1-(2-(4,5,6,7-tetrahydrobenzo[b]thiophen-4-yl)ethyl)piperidine

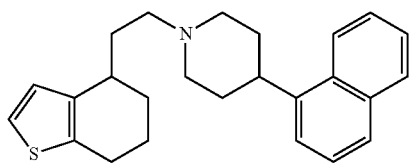 [SMILES: c1ccc2c(C3CCN(CCC4CCCc5sccc54)CC3)cccc2c1]

$^1$H NMR (300 MHz, CDCl$_3$): δ 1.57 (m, 1H), 177 (m, 2H), 1.87-2.13 (m, 7H), 2.25 (m, 2H), 2.55 (m, 2H), 2.78 (m, 3H), 3.19 (m, 2H), 3.35 (m, 1H), 6.90 (d, J=5.2 Hz, 1H), 7.06 (d, J=5.2 Hz, 1H), 7.42-7.54 (m, 4H), 7.71 (m, 1H), 7.86 (m, 1H), 8.10 (d, J=7.9 Hz, 1H).

(220 mg, 0.58 mmol, 98%, yellowish semisolid).

Example 32

4-(naphthalen-1-yl)-1-(2-(4,5,6,7-tetrahydrobenzo[b]thiophen-4-yl)ethyl)piperidine oxalate

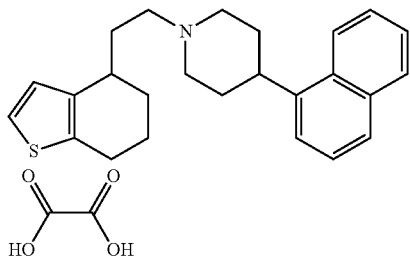

(136 mg, 0.29 mmol, 50%, m.p.=197-198° C., white solid).

Example 33

4-(4-chlorophenyl)-1-(2-(4,5,6,7-tetrahydrobenzo[b]thiophen-4-yl)ethyl)piperidine

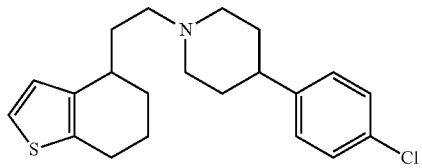 [SMILES: Clc1ccc(C2CCN(CCC3CCCc4sccc43)CC2)cc1]

$^1$H NMR (300 MHz, CDCl$_3$): δ 1.54 (m, 1H), 1.65-1.88 (m, 6H), 1.90-2.15 (m, 5H), 2.49 (m, 3H), 2.76 (m, 3H), 3.09 (m, 2H), 6.88 (d, J=5.2 Hz, 1H), 7.05 (d, J=5.2 Hz, 1H), 7.16 (d, J=8.4 Hz, 2H), 7.27 (d, J=8.4 Hz, 2H).

(220, 0.60 mmol, quant., beige semisolid).

Example 34

4-(4-chlorophenyl)-1-(2-(4,5,6,7-tetrahydrobenzo[b]thiophen-4-yl)ethyl)piperidine oxalate

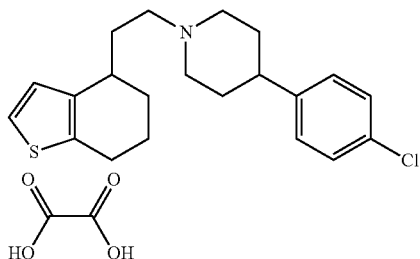

(155 mg, 0.34 mmol, 57%, m.p.=201-202° C., white solid).

Example 35

4-(2-methoxyphenyl)-1-(2-(4,5,6,7-tetrahydrobenzo[b]thiophen-4-yl)ethyl)piperidine

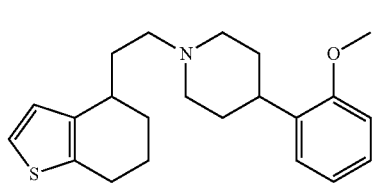 [SMILES: COc1ccccc1C1CCN(CCC2CCCc3sccc32)CC1]

$^1$H NMR (300 MHz, CDCl$_3$): δ 1.47-2.22 (m, 12H), 2.50 (t, J=8.1 Hz, 2H), 2.77 (m, 3H), 2.98 (m, 1H), 3.11 (m, 2H), 3.83 (s, 3H), 6.84-6.97 (m, 3H), 7.05 (d, J=5.3 Hz, 1H), 7.15-7.25 (m, 2H).

(196 mg, 0.55 mmol, 92%, beige semisolid).

Example 36

4-(2-methoxyphenyl)-1-(2-(4,5,6,7-tetrahydrobenzo[b]thiophen-4-yl)ethyl)piperidine oxalate

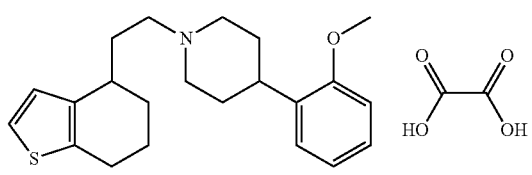

(106 mg, 0.24 mmol, 43%, m.p.=160-162° C., white solid).

Example 37

1-(2-(4,5,6,7-tetrahydrobenzo[b]thiophen-4-yl)ethyl)-4-p-tolylpiperidine

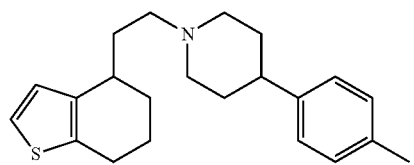 [SMILES: Cc1ccc(C2CCN(CCC3CCCc4sccc43)CC2)cc1]

$^1$H NMR (300 MHz, CDCl$_3$): δ 1.56 (m, 1H), 1.67-2.16 (m, 11H), 2.32 (s, 3H), 2.49 (m, 3H), 2.77 (m, 3H), 3.10 (m, 2H), 6.88 (d, J=5.2 Hz, 1H), 7.05 (d, J=5.2 Hz, 1H), 7.13 (m, 4H).

(199 mg, 0.59 mmol, 97%, beige semisolid).

Example 38

1-(2-(4,5,6,7-tetrahydrobenzo[b]thiophen-4-yl)ethyl)-4-p-tolylpiperidine oxalate

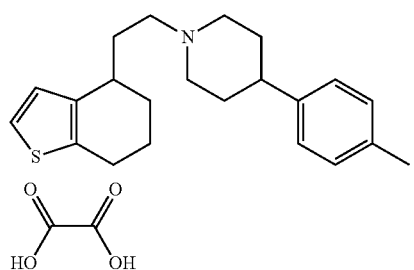

(120 mg, 0.28 mmol, 47%, m.p.=° C., white solid).

Example 39

4-(2-(2,3-dihydrospiro[1H-indene-1,4'-piperidin]-1'-yl)ethyl)-4,5,6,7-tetrahydrobenzo[b]thiophene

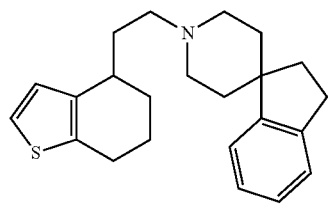 [SMILES: c1ccc2c(c1)CCC21CCN(CCC2CCCc3sccc32)CC1]

$^1$H NMR (300 MHz, CDCl$_3$): δ 1.57 (m, 3H), 1.76 (m, 3H), 1.89-2.28 (m, 8H, (δ=2.01, t, J=7.4 Hz)), 2.51 (m, 2H), 2.77 (m, 3H), 2.87-3.02 (m, 4H, (δ 2.90, J=7.3 Hz)), 6.89 (d, J=5.1 Hz, 1H), 7.05 (d, J=5.1 Hz, 1H), 7.14-724 (m, 4H).

(208 mg, 0.59 mmol, 98%, brown oil).

Example 40

4-(2-(2,3-dihydrospiro[1H-indene-1,4'-piperidin]-1'-yl)ethyl)-4,5,6,7-tetrahydrobenzo[b]thiophene oxalate

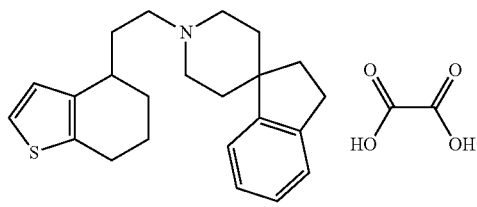

(135 mg, 0.31 mmol, 52%, m.p.=205-206° C., white solid).

Example 41

4-(3-chlorophenyl)-1-(2-(4,5,6,7-tetrahydrobenzo[b]thiophen-4-yl)ethyl)piperidine

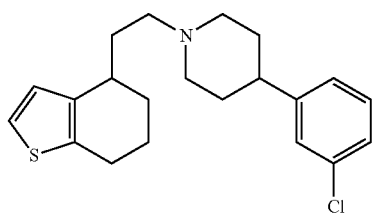 [SMILES: Clc1cccc(C2CCN(CCC3CCCc4sccc43)CC2)c1]

$^1$H NMR (300 MHz, CDCl$_3$): δ 1.47-2.15 (m, 12H), 2.49 (m, 3H), 2.77 (m, 3H), 3.10 (m, 2H), 6.88 (d, J=5.1 Hz, 1H), 7.05 (d, J=5.1 Hz, 1H), 7.11 (m, 1H), 7.15-7.24 (m, 3H).

(181 mg, 0.50 mmol, 84%, amber oil).

Example 42

4-(3-chlorophenyl)-1-(2-(4,5,6,7-tetrahydrobenzo[b]thiophen-4-yl)ethyl)piperidine oxalate

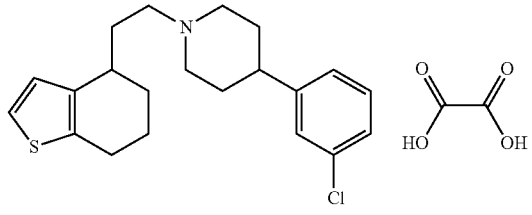

(122 mg, 0.27 mmol, 54%, m.p.=185-186° C., white solid).

Example 43

4-(3-methoxyphenyl)-1-(2-(4,5,6,7-tetrahydrobenzo[b]thiophen-4-yl)ethyl)piperidine

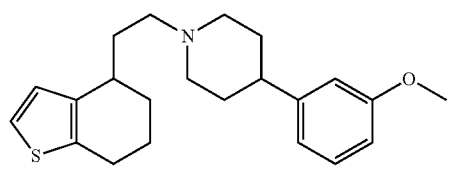 [SMILES: COc1cccc(C2CCN(CCC3CCCc4sccc43)CC2)c1]

$^1$H NMR (300 MHz, CDCl$_3$): δ 1.53 (m, 1H), 1.65-2.14 (m, 11H), 2.49 (m, 3H), 2.77 (m, 3H), 3.10 (m, 2H), 3.80 (s, 3H), 6.75 (m, 1H), 6.80 (s, 1H), 6.84 (d, J=8.0 Hz, 1H), 6.89 (d, J=5.1 Hz, 1H), 7.05 (d, J=5.1 Hz, 1H), 7.22 (t, J=8.0 Hz, 1H).

(187 mg, 0.53 mmol, 88%, yellowish oil).

Example 44

4-(3-methoxyphenyl)-1-(2-(4,5,6,7-tetrahydrobenzo[b]thiophen-4-yl)ethyl)piperidine oxalate

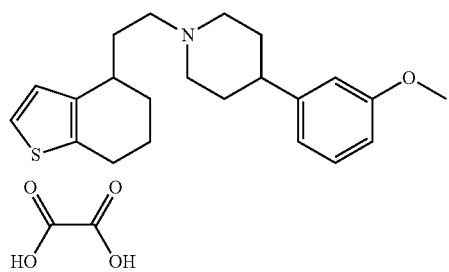

(122 mg, 0.27 mmol, 52%, m.p.=157-159° C., white solid).

Example 45

4-(4-fluorophenyl)-1-(2-(4,5,6,7-tetrahydrobenzo[b]thiophen-4-yl)ethyl)piperidine

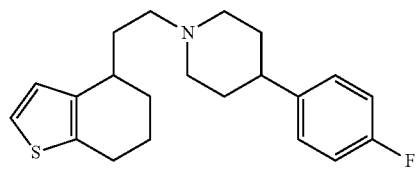 [SMILES: Fc1ccc(C2CCN(CCC3CCCc4sccc43)CC2)cc1]

$^1$H NMR (300 MHz, CDCl$_3$): δ1.52 (m, 1H), 1.64-2.16 (m, 11H), 2.49 (m, 3H), 2.77 (m, 3H), 3.10 (m, 2H), 6.88 (d, J=5.1 Hz, 1H), 6.98 (t, J=8.5 Hz, 2H), 7.05 (d, J=5.1 Hz, 1H), 7.19 (m, 2H).

(oil).

Example 46

4-(4-fluorophenyl)-1-(2-(4,5,6,7-tetrahydrobenzo[b]thiophen-4-yl)ethyl)piperidine oxalate

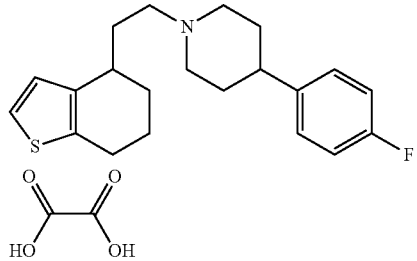

(108 mg, 0.25 mmol, m.p.=179-181° C., off-white solid).

Example 47

4-(3,5-bis(trifluoromethyl)phenyl)-1-(2-(4,5,6,7-tetrahydrobenzo[b]thiophen-4-yl)ethyl)piperidine

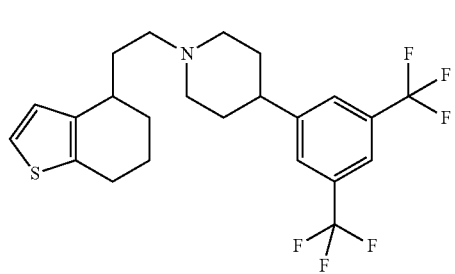

$^1$H NMR (300 MHz, CDCl$_3$): δ 1.46-2.19 (m, 12H), 2.49 (m, 2H), 2.66 (m, 1H), 2.77 (m, 3H), 3.12 (m, 2H), 6.87 (d, J=5.1 Hz, 1H), 7.05 (d, J=5.1 Hz, 1H), 7.68 (s, 2H), 7.71 (s, 1H).

(189 mg, 0.41 mmol, 68%, amber oil).

Example 48

4-(3,5-bis(trifluoromethyl)phenyl)-1-(2-(4,5,6,7-tetrahydrobenzo[b]thiophen-4-yl)ethyl)piperidine oxalate

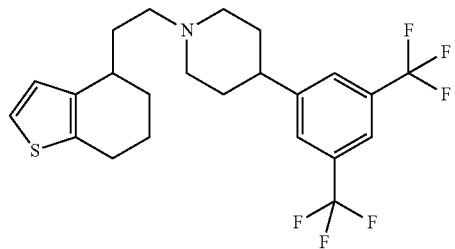 [SMILES: FC(F)(F)c1cc(C2CCN(CCC3CCCc4sccc43)CC2)cc(C(F)(F)F)c1]

-continued

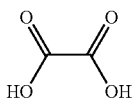

(94 mg, 0.17 mmol, 42%, m.p.=205-206° C., white solid).

Example 49

4-(naphthalen-2-yl)-1-(2-(4,5,6,7-tetrahydrobenzo[b]thiophen-4-yl)ethyl)piperidine

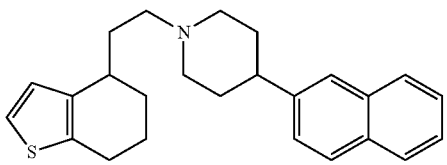 [SMILES: c1ccc2cc(C3CCN(CCC4CCCc5sccc54)CC3)ccc2c1]

$^1$H NMR (300 MHz, CDCl$_3$): δ 1.56 (m, 1H), 1.66-2.22 (m, 11H), 2.52 (t, J=8.0 Hz, 2H), 2.68 (m, 1H), 2.77 (m, 3H), 3.15 (m, 2H), 6.90 (d, J=5.2 Hz, 1H), 7.06 (d, J=5.2 Hz, 1H), 7.42 (m, 3H), 7.66 (s, 1H), 7.79 (m, 3H).
(180 mg, 0.48 mmol, 80%, amber oil).

Example 50

4-(naphthalen-2-yl)-1-(2-(4,5,6,7-tetrahydrobenzo[b]thiophen-4-yl)ethyl)piperidine oxalate

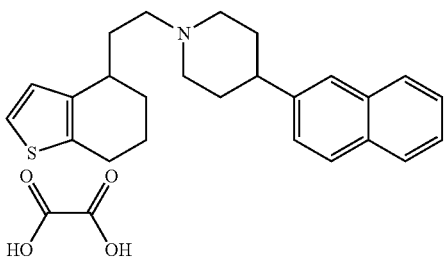

(140 mg, 0.30 mmol, 63%, m.p.=203-205° C., white solid).

Example 51

4-(benzofuran-2-yl)-1-(2-(4,5,6,7-tetrahydrobenzo[b]thiophen-4-yl)ethyl)piperidine

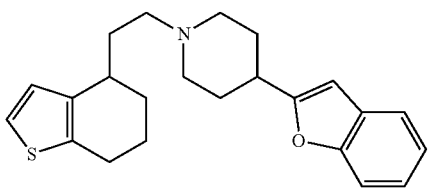 [SMILES: c1ccc2oc(C3CCN(CCC4CCCc5sccc54)CC3)cc2c1]

$^1$H NMR (300 MHz, CDCl$_3$): δ 1.54 (m, 1H), 1.64-2.18 (m, 11H), 2.48 (t, J=7.8 Hz, 2H), 2.76 (m, 4H), 3.05 (m, 2H), 6.38 (s, 1H), 6.88 (d, J=5.2 Hz, 1H), 7.05 (d, J=5.2 Hz, 1H), 7.19 (m, 2H), 7.40 (d, J=7.2 Hz, 1H), 7.49 (m, 1H)
(194 mg, 0.53 mmol, 88%, amber oil).

Example 52

4-(benzofuran-2-yl)-1-(2-(4,5,6,7-tetrahydrobenzo[b]thiophen-4-yl)ethyl)piperidine oxalate

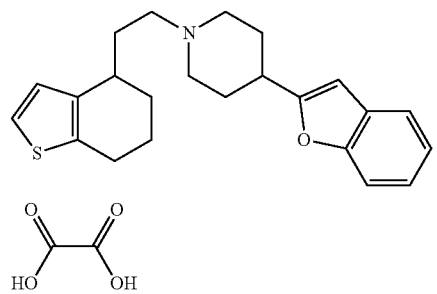

(170 mg, 0.37 mmol, 70%, m.p.=207-208° C., white solid).

Example 53

4-(2-fluorophenyl)-1-(2-(4,5,6,7-tetrahydrobenzo[b]thiophen-4-yl)ethyl)piperidine

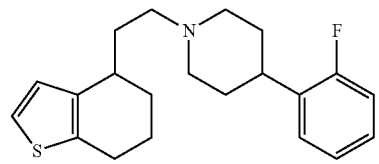 [SMILES: Fc1ccccc1C1CCN(CCC2CCCc3sccc32)CC1]

$^1$H NMR (300 MHz, CDCl$_3$): δ 1.54 (m, 1H), 1.64-2.17 (m, 11H), 2.49 (m, 2H), 2.76 (m, 3H), 2.89 (m, 1H), 3.10 (m, 2H), 6.88 (d, J=5.1 Hz, 1H), 6.97-7.20 (m, 4H), 7.26 (m, 1H).
(oil).

Example 54

4-(2-fluorophenyl)-1-(2-(4,5,6,7-tetrahydrobenzo[b]thiophen-4-yl)ethyl)piperidine oxalate

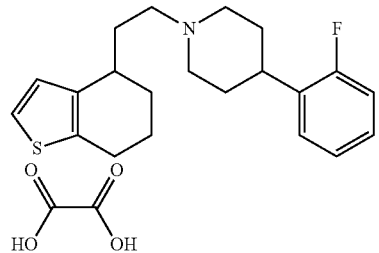

(120 mg, 0.28 mmol, m.p.=208-209° C., white solid).

Example 55

2-phenyl-1-(2-(4,5,6,7-tetrahydrobenzo[b]thiophen-4-yl)ethyl)piperidine

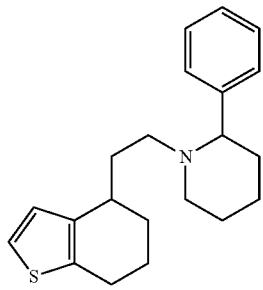 [SMILES: c1ccc(C2CCCCN2CCC2CCCc3sccc32)cc1]

$^1$H NMR (300 MHz, CDCl$_3$): δ 1.06-2.21 (m, 14H), 2.37-2.72 (m, 4H), 3.04 and 3.19 (2×m, 2H), 6.61 and 6.73 (2×d, J=5.1 Hz, 1H), 6.95 and 6.98 (2×d, J=5.1 Hz, 1H), 7.19-7.38 (m, 5H).

(180 mg, 0.55 mmol, 92%, brown oil).

Example 56

4-(benzo[b]thiophen-3-yl)-1-(2-(4,5,6,7-tetrahydrobenzo[b]thiophen-4-yl)ethyl)piperidine

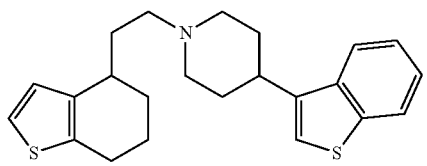 [SMILES: c1ccc2c(C3CCN(CCC4CCCc5sccc54)CC3)csc2c1]

$^1$H NMR (300 MHz, CDCl$_3$): δ 1.46-2.22 (m, 12H), 2.49 (m, 2H), 2.72-2.95 (m, 4H), 3.08 (m, 2H), 6.88 (d, J=5.3 Hz, 1H), 7.05 (m, 2H), 7.22-7.33 (m, 2H), 7.67 (d, J=7.9 Hz, 1H), 7.77 (d, J=8.5 Hz, 1H).

(170 mg, 0.44 mmol, 74%, brown oil).

Example 57

4-(benzo[b]thiophen-3-yl)-1-(2-(4,5,6,7-tetrahydrobenzo[b]thiophen-4-yl)ethyl)piperidine oxalate

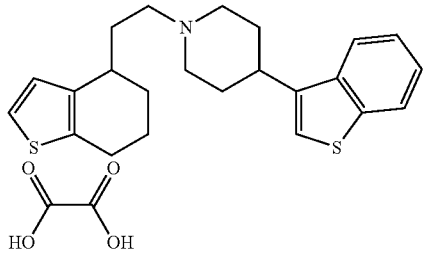

(42 mg, 0.09 mmol, 20%, m.p.=190-192° C., white solid).

Example 58

2-(1-(2-(4,5,6,7-tetrahydrobenzo[b]thiophen-4-yl)ethyl)piperidin-4-yl)-1H-benzo[d]imidazole

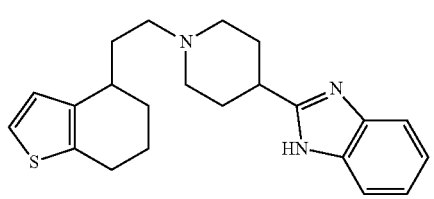 [SMILES: c1ccc2[nH]c(C3CCN(CCC4CCCc5sccc54)CC3)nc2c1]

$^1$H NMR (300 MHz, CDCl$_3$): δ 1.54 (m, 1H), 1.73 (m, 2H), 1.96 (m, 5H), 2.17 (m, 4H), 2.50 (t, J=7.8 Hz, 2H), 2.76 (m, 3H), 2.98 (m, 1H), 3.10 (m, 2H), 6.86 (d, J=5.1 Hz, 1H), 7.04 (d, J=5.1 Hz, 1H), 7.22 (m, 2H), 7.55 (m, 2H), 9.17 (m, 1H).

(150 mg, 0.41 mmol, 68%, beige semisolid).

Example 59

2-(1-(2-(4,5,6,7-tetrahydrobenzo[b]thiophen-4-yl)ethyl)piperidin-4-yl)-1H-benzo[d]imidazole oxalate

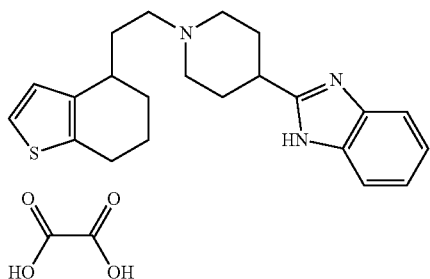

(52 mg, 0.11 mmol, 28%, m.p.=223-225° C., white solid).

Example 60

2-methyl-1-(1-(2-(4,5,6,7-tetrahydrobenzo[b]thiophen-4-yl)ethyl)piperidin-4-yl)-1H-benzo[d]imidazole

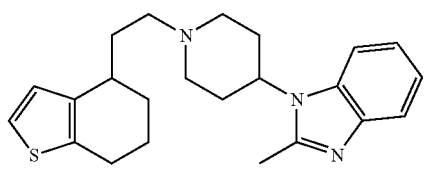 [SMILES: Cc1nc2ccccc2n1C1CCN(CCC2CCCc3sccc32)CC1]

$^1$H NMR (300 MHz, CDCl$_3$): δ 1.56 (m, 1H), 1.64-2.22 (m, 11H), 2.53 (m, 2H), 2.63 (s, 3H), 2.76-2.89 (m, 3H), 3.18 (m, 2H), 4.17 (m, 1H), 6.88 (d, J=5.3 Hz, 1H), 7.06 (d, J=5.3 Hz, 1H), 7.19 (m, 2H), 7.59 (m, 1H), 7.68 (m, 1H).

(156 mg, 0.41 mmol, 68%, beige oil).

Example 61

2-methyl-1-(1-(2-(4,5,6,7-tetrahydrobenzo[b]thiophen-4-yl)ethyl)piperidin-4-yl)-1H-benzo[d]imidazole oxalate

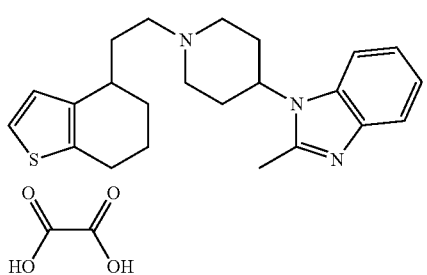

(127 mg, 0.27 mmol, 66%, m.p.=155-157° C., white solid).

Example 62

4-(4-methoxyphenyl)-1-(2-(4,5,6,7-tetrahydrobenzo[b]thiophen-4-yl)ethyl)piperidine

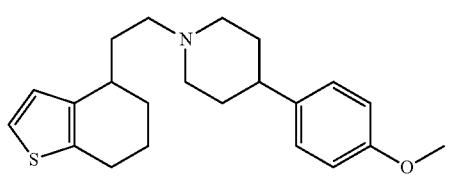 [SMILES: COc1ccc(C2CCN(CCC3CCCc4sccc43)CC2)cc1]

$^1$H NMR (300 MHz, CDCl$_3$): δ 1.47-1.87 (m, 7H), 1.98 (m, 5H), 2.47 (m, 3H), 2.76 (m, 3H), 3.07 (m, 2H), 3.79 (s, 3H), 6.85 (d. J=8.8 Hz, 2H), 6.88 (d, J=5.1 Hz, 1H), 7.04 (d, J=5.1 Hz, 1H), 7.16 (d, J=8.8 Hz, 2H).

(167 mg, 0.47 mmol, 78%, semisolid).

Example 63

4-(4-methoxyphenyl)-1-(2-(4,5,6,7-tetrahydrobenzo[b]thiophen-4-yl)ethyl)piperidine oxalate

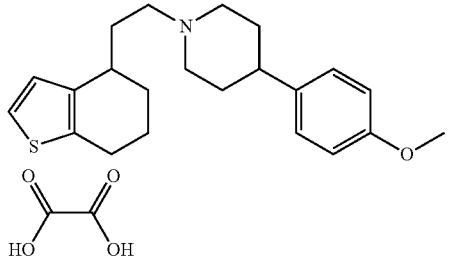

(135 mg, 0.30 mmol, 64%, m.p.=175-176° C., white solid).

Example 64

2-Methyl-8-[2-(4,5,6,7-tetrahydrobenzo[b]thiophen-4-yl)-ethyl]-2,8-diazaspiro[4.5]decan-1-one

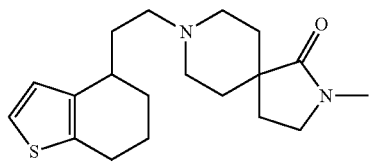 [SMILES: CN1CCC2(CCN(CCC3CCCc4sccc43)CC2)C1=O]

$^1$H NMR (300 MHz, CDCl$_3$): δ 1.37-2.15 (m, 14H), 2.43 (m, 2H), 2.74 (m, 3H), 2.84 (s, 3H), 2.90 (m, 2H), 3.28 (t, J=7.2 Hz, 2H), 6.85 (d, J=5.2 Hz, 1H), 7.02 (d, J=5.2 Hz, 1H).

(160 mg, 0.48 mmol, 80%, amber oil).

Example 65

2-Methyl-8-[2-(4,5,6,7-tetrahydrobenzo[b]thiophen-4-yl)-ethyl]-2,8-diazaspiro[4.5]decan-1-one oxalate

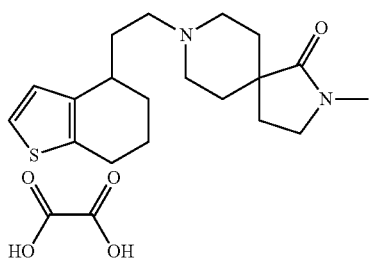

(126 mg, 0.30 mmol, 62%, m.p.=140-142° C., white solid).

Example 66

1'-(2-(4,5,6,7-tetrahydrobenzo[b]thiophen-4-yl)ethyl)-spiro(isobenzofuran-1(3H), 4'-piperidin)-3-one

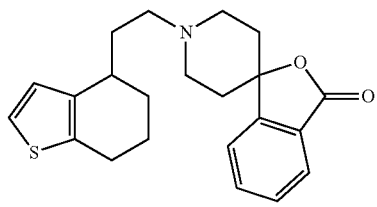 [SMILES: O=C1OC2(CCN(CCC3CCCc4sccc43)CC2)c2ccccc21]

$^1$H NMR (300 MHz, CDCl$_3$): δ 1.55 (m, 1H), 1.67-1.84 (m, 4H), 1.98 (m, 3H), 2.24 (m, 2H), 2.44-2.63 (m, 4H), 2.77 (m, 3H), 2.97 (m, 2H), 6.88 (d, J=5.2 Hz, 1H), 7.05 (d, J=5.2 Hz, 1H), 7.41 (d, J=7.6 Hz, 1H), 7.51 (t, J=7.6 Hz, 1H), 7.66 (t, J=7.6 Hz, 1H), 7.88 (d, J=7.6 Hz, 1H).

(148 mg, 0.40 mmol, 67%, amber solid)

Example 67

1'-(2-(4,5,6,7-tetrahydrobenzo[b]thiophen-4-yl)ethyl)-spiro(isobenzofuran-1(3H), 4'-piperidin)-3-one oxalate

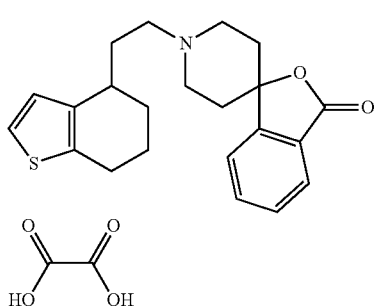

(112 mg, 0.24 mmol, 61%, m.p.=186-189° C., white solid).

Example 68

2-(4-Chlorophenyl)-8-[2-(4,5,6,7-tetrahydrobenzo[b]thiophen-4-yl)-ethyl]-2,8-diazaspiro[4.5]decan-1-one

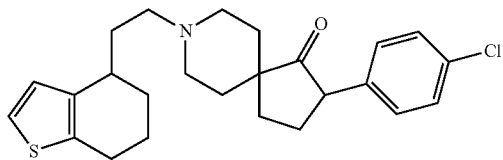 [SMILES: O=C1C(c2ccc(Cl)cc2)CCC12CCN(CCC1CCCc3sccc31)CC2]

$^1$H NMR (300 MHz, CDCl$_3$): δ 1.38-1.74 (m, 5H), 1.80-2.16 (m, 9H), 2.39 (m, 2H), 2.69 (m, 3H), 2.85 (m, 2H), 3.67 (t, J=7.0 Hz, 2H), 6.80 (d, J=5.1 Hz, 1H), 6.96 (d, J=5.1 Hz, 1H), 7.25 (d, J=8.8 Hz, 2H), 7.55 (d, J=8.8 Hz, 2H).

(beige solid).

Example 69

2-(4-Chlorophenyl)-8-[2-(4,5,6,7-tetrahydrobenzo[b]thiophen-4-yl)-ethyl]-2,8-diazaspiro[4.5]decan-1-one oxalate

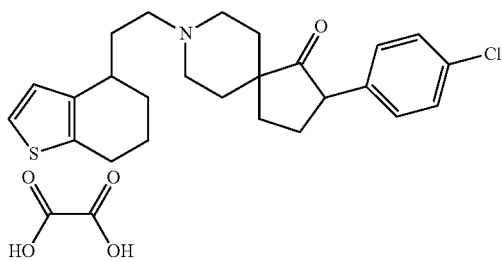

(185 mg, 0.35 mmol, m.p.=218-220° C., white solid).

Example 70

8-[2-(4,5,6,7-Tetrahydrobenzo[b]thiophen-4-yl)-ethyl]-2,8-diazaspiro[4.5]decan-1-one

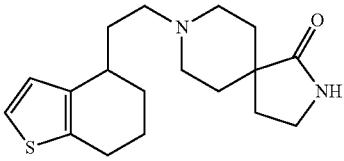 [SMILES: O=C1NCCC12CCN(CCC1CCCc3sccc31)CC2]

$^1$H NMR (300 MHz, CDCl$_3$): δ 1.39-1.81 (m, 5H), 1.86-2.16 (m, 9H), 2.43 (m, 2H), 2.71-2.94 (m, 5H), 3.31 (t, J=6.9 Hz, 2H), 5.78 (br s, 1H), 6.85 (d, J=5.2 Hz, 1H), 7.03 (d, J=5.2 Hz, 1H).

(168 mg, 0.53 mmol, 88%, colorless oil).

Example 71

8-[2-(4,5,6,7-Tetrahydrobenzo[b]thiophen-4-yl)-ethyl]-2,8-diazaspiro[4.5]decan-1-one oxalate

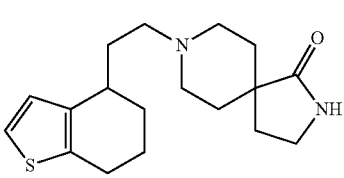

(111 mg, 0.27 mmol, 51%, m.p.=147-149° C., white solid).

Example 72

4-(2-(spiro[1H-indene-1,4'-piperidin]-1'-yl)ethyl)-4,5,6,7-tetrahydrobenzo[b]thiophene

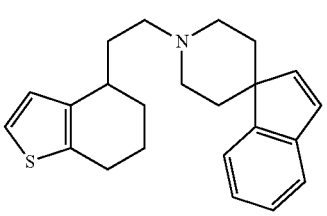 [SMILES: C1=CC2(CCN(CCC3CCCc4sccc43)CC2)c2ccccc21]

$^1$H NMR (300 MHz, CDCl$_3$): δ 1.40 (m, 2H), 1.57 (m, 1H), 1.77 (m, 2H), 1.90-2.11 (m, 3H), 2.15-2.43 (m, 4H), 2.57 (t, J=8.0 Hz, 2H), 2.77 (m, 3H), 3.05 (m, 2H), 6.75 (d, J=5.6 Hz, 1H), 6.85 (d, J=5.6 Hz, 1H), 6.90 (d, J=5.2 Hz, 1H), 7.06 (d, J=5.2 Hz, 1H), 7.22 (m, 2H), 7.31 (m, 1H), 7.38 (d, J=7.0 Hz, 1H).

(beige semisolid)

Example 73

4-(2-(spiro[1H-indene-1,4'-piperidin]-1'-yl)ethyl)-4,5,6,7-tetrahydrobenzo[b]thiophene oxalate

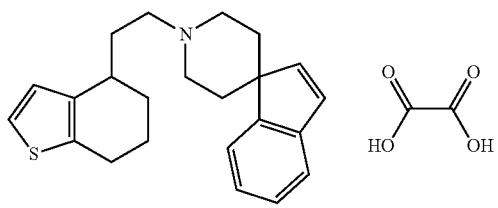 [SMILES: C1=CC2(CCN(CCC3CCCc4sccc43)CC2)c2ccccc21 ; O=C(O)C(=O)O]

(162 mg, 36.8 mmol, 61%, m.p.=198-199° C., white solid).

Example 74

7-methoxy-2-(2-(4,5,6,7-tetrahydrobenzo[b]thiophen-4-yl)ethyl)-1,2,3,4-tetrahydroisoquinoline

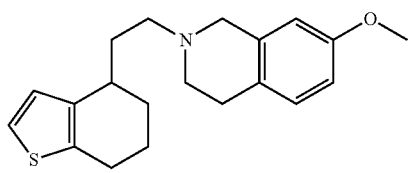 [SMILES: COc1ccc2c(c1)CN(CCC1CCCc3sccc31)CC2]

$^1$H NMR (300 MHz, CDCl$_3$): δ 1.55 (m, 1H), 1.78 (m, 2H), 1.94 (m, 2H), 2.09 (m, 1H), 2.65 (m, 2H), 2.71-2.92 (m, 7H), 3.68 (m, 2H), 3.77 (s, 3H), 6.56 (d, J=2.7 Hz, 1H), 6.72 (dd, J=8.4 Hz, J'=2.7 Hz, 1H), 6.89 (d, J=5.3 Hz, 1H), 7.02 (d, J=8.4 Hz, 1H), 7.05 (d, J=7.5 Hz, 1H).

(colorless oil).

Example 75

7-methoxy-2-(2-(4,5,6,7-tetrahydrobenzo[b]thiophen-4-yl)ethyl)-1,2,3,4-tetrahydroisoquinoline oxalate

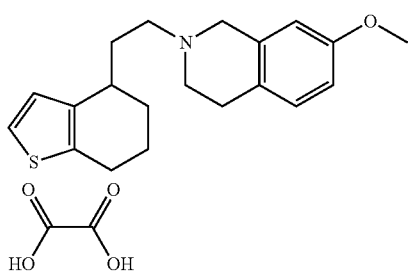

(104 mg, 0.25 mmol, 42%, m.p.=200-201° C., white solid).

Example 76

5,7-dichloro-2-(2-(4,5,6,7-tetrahydrobenzo[b]thiophen-4-yl)ethyl)-1,2,3,4-tetrahydroisoquinoline

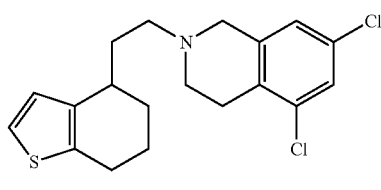 [SMILES: Clc1cc(Cl)c2c(c1)CN(CCC1CCCc3sccc31)CC2]

$^1$H NMR (300 MHz, CDCl$_3$): δ 1.56 (m, 1H), 1.75 (m, 2H), 1.89-2.10 (m, 3H), 2.60 (m, 2H), 2.72-2.87 (m, 7H), 3.58 (m, 2H), 6.86 (d, J=5.2 Hz, 1H), 6.95 (d, J=2.0 Hz, 1H), 7.05 (d, J=5.2 Hz, 1H), 7.22 (d, J=2.0 Hz, 1H).

(212 mg, 0.58 mmol, 96%, brown oil).

Example 77

5,7-dichloro-2-(2-(4,5,6,7-tetrahydrobenzo[b]thiophen-4-yl)ethyl)-1,2,3,4-tetrahydroisoquinoline oxalate

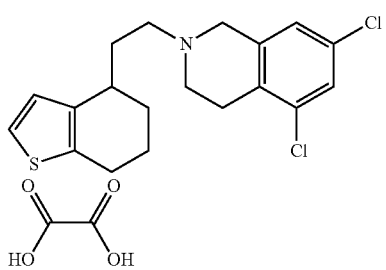

(50 mg, 0.11 mmol, 19%, m,p,=182-184° C., white solid).

Example 78

1-(1-(2-(4,5,6,7-tetrahydrobenzo[b]thiophen-4-yl)ethyl)piperidin-4-yl)-1H-indole

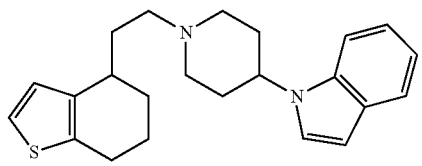 [SMILES: c1ccc2c(c1)ccn2C1CCN(CCC2CCCc3sccc32)CC1]

$^1$H NMR (300 MHz, CDCl$_3$): δ 1.55 (m, 1H), 1.69-2.37 (m, 11H), 2.58 (m, 2H), 2.72-2.87 (m, 3H), 3.21 (m, 2H), 4.28 (m, 1H), 6.52 (d, J=3.2 Hz, 1H), 6.88 (d, J=5.1 Hz, 1H), 7.06 (d, J=5.1 Hz, 1H), 7.10 (m, 1H), 7.20 (m, 1H), 7.25 (d, J=3.2 Hz, 1H), 7.37 (d, J=8.9 Hz, 1H), 7.63 (d, J=7.8 Hz, 1H).

(205 mg, 0.56 mmol, 93%, amber oil).

Example 79

1-(1-(2-(4,5,6,7-tetrahydrobenzo[b]thiophen-4-yl)ethyl)piperidin-4-yl)-1H-indole oxalate

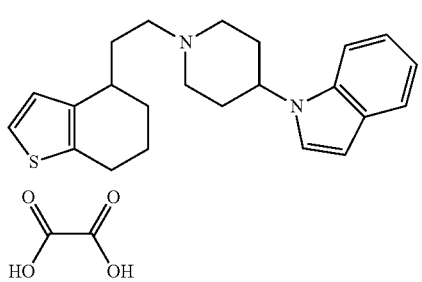

(180 mg, 0.39 mmol, 70%, m.p.=162-164° C., white solid).

Example 80

2-tert-butyl-8-[2-(4,5,6,7-tetrahydrobenzo[b]thiophen-4-yl)-ethyl]-2,8-diazaspiro[4.5]decan-1-one

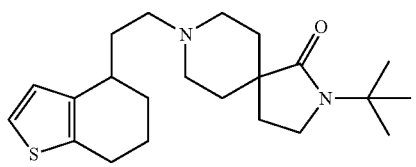 [SMILES: CC(C)(C)N1CCC2(CCN(CCC3CCCc4sccc43)CC2)C1=O]

$^1$H NMR (300 MHz, CDCl$_3$): δ 1.37 (s, 9H), 1.41-2.28 (m, 14H), 2.48 (m, 2H), 2.74 (m, 3H), 2.94 (m, 2H), 3.31 (t, J=6.8 Hz, 2H), 6.86 (d, J=5.2 Hz, 1H), 7.03 (d, J=5.2 Hz, 1H).

(185 mg, 0.49 mmol, 82%, amber oil).

Example 81

2-tert-butyl-8-[2-(4,5,6,7-tetrahydrobenzo[b]thiophen-4-yl)-ethyl]-2,8-diazaspiro[4.5]decan-1-one oxalate

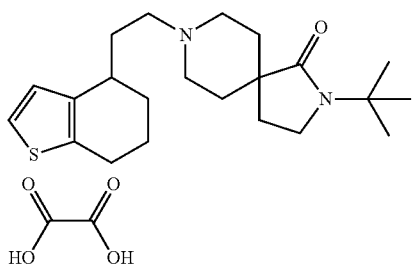

(138 mg, 29.7 mmol, 60%, m.p.=172-173° C., white solid).

Example 82

2-benzyl-8-[2-(4,5,6,7-tetrahydrobenzo[b]thiophen-4-yl)-ethyl]-2,8-diazaspiro[4.5]decan-1-one

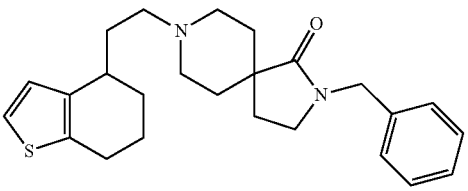 [SMILES: O=C1N(Cc2ccccc2)CCC12CCN(CCC1CCCc3sccc31)CC2]

$^1$H NMR (300 MHz, CDCl$_3$): δ 1.44-2.27 (m, 14H), 2.48 (m, 2H), 2.75 (m, 3H), 2.96 (m, 2H), 3.15 (t, J=7.0 Hz, 2H), 4.44 (s, 2H), 6.86 (d, J=5.1 Hz, 1H), 7.03 (d. J=5.1 Hz, 1H), 7.20 (m, 2H), 7.26-7.35 (m, 3H).

(211 mg, 0.52 mmol, 86% amber oil).

Example 83

2-benzyl-8-[2-(4,5,6,7-tetrahydrobenzo[b]thiophen-4-yl)-ethyl]-2,8-diazaspiro[4.5]decan-1-one oxalate

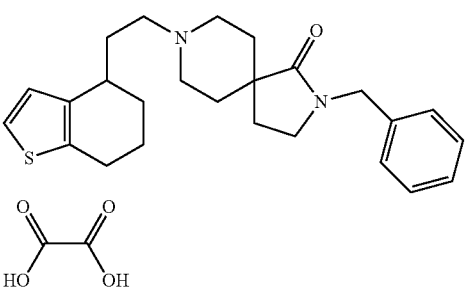

(160 mg, 0.32 mmol, 62%, m.p=170-171° C., white solid).

Example 84

2-(4-Methoxyphenyl)-8-[2-(4,5,6,7-tetrahydrobenzo[b]thiophen-4-yl)-ethyl]-2,8-diazaspiro[4.5]decan-1-one

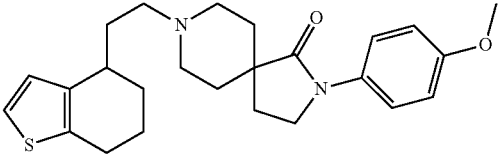 [SMILES: COc1ccc(N2CCC3(CCN(CCC4CCCc5sccc54)CC3)C2=O)cc1]

$^1$H NMR (300 MHz, CDCl$_3$): δ 1.46-2.40 (m, 14H), 2.53 (m, 2H), 2.75 (m, 3H), 3.00 (m, 2H), 3.74 (t, J=6.9 Hz, 2H), 3.79 (s, 3H), 6.87 (m, 3H), 7.04 (d, J=5.3 Hz, 1H), 7.53 (, d, J=9.1 Hz, 2H).

(179 mg, 0.42 mmol, 70%, colorless oil).

Example 85

2-(4-Methoxyphenyl)-8-[2-(4,5,6,7-tetrahydrobenzo[b]thiophen-4-yl)-ethyl]-2,8-diazaspiro[4.5]decan-1-one oxalate

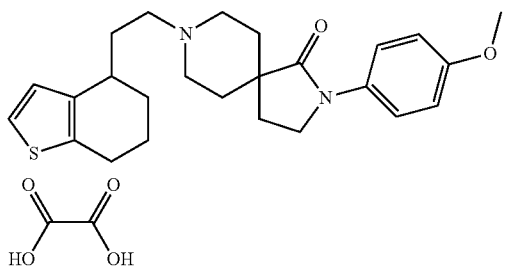

(165 mg, 0.32 mmol, 76%, m.p.=205-206° C., white solid).

Example 86

2-phenyl-8-[2-(4,5,6,7-tetrahydrobenzo[b]thiophen-4-yl)-ethyl]-2,8-diazaspiro[4.5]decan-1-one

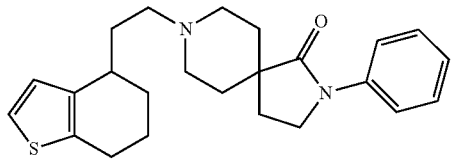 [SMILES: O=C1N(c2ccccc2)CCC12CCN(CCC1CCCc3sccc31)CC2]

$^1$H NMR (300 MHz, CDCl$_3$): δ 1.45-2.35 (m, 14H), 2.51 (m, 2H), 2.75 (m, 3H), 2.99 (m, 2H), 3.78 (m, 2H), 6.87 (m, 1H), 7.04 (m, 1H), 7.13 (m, 1H), 7.36 (m, 2H), 7.64 (m, 2H).

(229 mg, 0.58 mmol, 97%, amber oil).

Example 87

2-phenyl-8-[2-(4,5,6,7-tetrahydrobenzo[b]thiophen-4-yl)-ethyl]-2,8-diazaspiro[4.5]decan-1-one oxalate

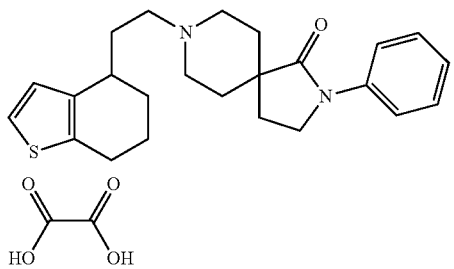

(144 mg, 0.30 mmol, 52%, m.p.=200-201° C., beige solid).

Example 88

2-(4-trifluoromethylphenyl)-8-[2-(4,5,6,7-tetrahydrobenzo[b]thiophen-4-yl)-ethyl]-2,8-diazaspiro[4.5]decan-1-one

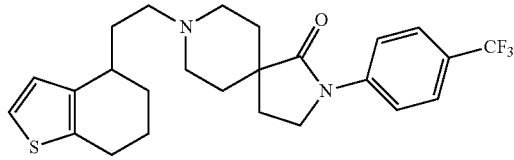 [SMILES: O=C1N(c2ccc(C(F)(F)F)cc2)CCC12CCN(CCC1CCCc3sccc31)CC2]

$^1$H NMR (300 MHz, CDCl$_3$): δ 1.45-2.33 (m, 14H), 2.51 (m, 2H), 2.75 (m, 3H), 2.98 (m, 2H), 3.80 (m, 2H), 6.87 (d, J=4.7 Hz, 1H), 7.05 (d, J=4.7 Hz, 1H), 7.60 (d, J=8.0 Hz, 2H), 7.80 (d, J=8.0 Hz, 2H).

(261 mg, 0.56 mmol, 94%, beige oil).

Example 89

2-(4-trifluoromethylphenyl)-8-[2-(4,5,6,7-tetrahydrobenzo[b]thiophen-4-yl)-ethyl]-2,8-diazaspiro[4.5]decan-1-one oxalate

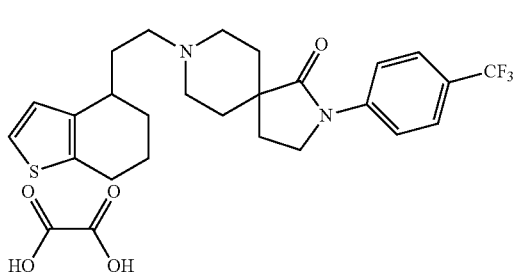

(152 mg, 0.27 mmol, 48%, m.p.=166-168° C., white solid).

Example 90

5-bromo-2-(2-(4,5,6,7-tetrahydrobenzo[b]thiophen-4-yl)ethyl)-1,2,3,4-tetrahydroisoquinoline

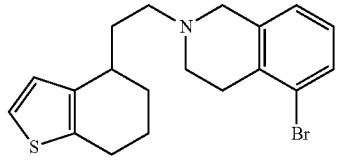 [SMILES: Brc1cccc2c1CCN(CCC1CCCc3sccc31)C2]

$^1$H NMR (300 MHz, CDCl$_3$): δ 1.55 (m, 1H), 1.69-1.97 (m, 4H), 2.10 (m, 1H), 2.57-2.95 (m, 9H), 3.72 (m, 2H), 6.88 (d, J=5.1 Hz, 1H), 6.98-7.07 (m, 3H), 7.41 (dd, J=7.0 Hz, J'=1.1 Hz, 1H).

(200 mg, 0.53 mmol, 89%, cream oil).

Example 91

5-bromo-2-(2-(4,5,6,7-tetrahydrobenzo[b]thiophen-4-yl)ethyl)-1,2,3,4-tetrahydroisoquinoline oxalate

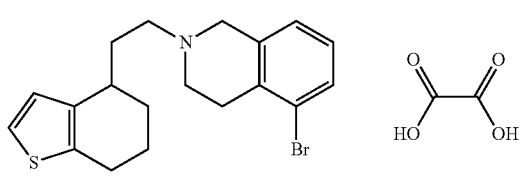 [SMILES: Brc1cccc2c1CCN(CCC1CCCc3sccc31)C2 ; O=C(O)C(=O)O]

(77 mg, 0.16 mmol, 30%, m.p.=167-168° C., white solid).

Example 92

2-(2-(4,5,6,7-tetrahydrobenzo[b]thiophen-4-yl)ethyl)-1,2,3,4-tetrahydroisoquinoline-7-carbonitrile

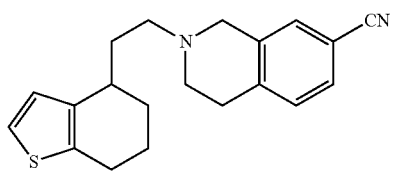 [SMILES: N#Cc1ccc2c(c1)CN(CCC1CCCc3sccc31)CC2]

$^1$H NMR (300 MHz, CDCl$_3$): δ 1.55 (m, 1H), 1.76 (m, 2H), 1.94 (m, 2H), 2.08 (m, 1H), 2.65 (m, 2H), 2.70-2.88 (m, 5H), 3.00 (m, 2H), 3.70 (m, 2H), 6.87 (d, J=5.1 Hz, 1H), 7.06 (d, J=5.1 Hz, 1H), 7.20 (d, J=7.8 Hz, 1H), 7.22 (s, 1H), 7.41 (d, J=7.8 Hz, 1H).

(183 mg, 0.57 mmol, 95%, cream semisolid).

Example 93

2-(2-(4,5,6,7-tetrahydrobenzo[b]thiophen-4-yl)ethyl)-1,2,3,4-tetrahydroisoquinoline-7-carbonitrile oxalate

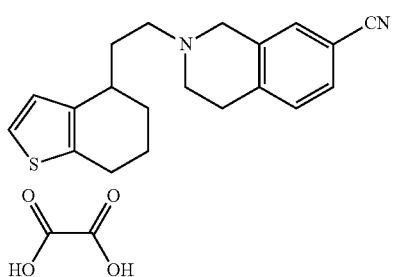

(72 mg, 0.17 mmol, 31%, m.p.=180-181° C., white solid)

Example 94

2-(4-Fluorophenyl)-8-[2-(4,5,6,7-tetrahydrobenzo[b]thiophen-4-yl)-ethyl]-2,8-diazaspiro[4.5]decan-1-one

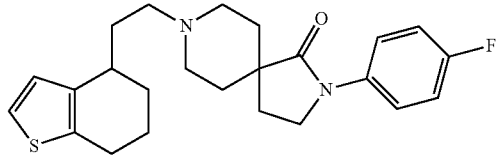 [SMILES: O=C1N(c2ccc(F)cc2)CCC12CCN(CCC1CCCc3sccc31)CC2]

$^1$H NMR (300 MHz, CDCl$_3$): δ 1.47-2.37 (m, 14H), 2.53 (m, 2H), 2.77 (m, 3H), 3.00 (m, 2H), 3.75 (t, J=7.0 Hz, 2H), 6.86 (d, J=5.1 Hz, 1H), 7.05 (m, 3H), 7.59 (dd, J=9.2 Hz, J'=4.9 Hz, 2H).

(233 mg, 0.57 mmol, 94%, beige semisolid).

Example 95

2-(4-Fluorophenyl)-8-[2-(4,5,6,7-tetrahydrobenzo[b]thiophen-4-yl)-ethyl]-2,8-diazaspiro[4.5]decan-1-one oxalate

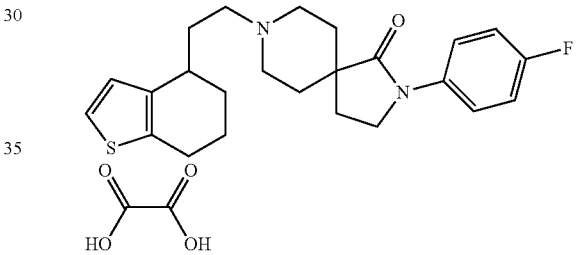

(96 mg, 0.19 mmol, 34%, m.p.=195-199° C., white solid).

BIOLOGICAL ACTIVITY

Some representative compounds of the invention were tested for their activity as sigma (sigma-1 and sigma-2) inhibitors. The following protocols were followed:

Sigma-1

Brain membrane preparation and binding assays for the σ1-receptor were performed as described (DeHaven-Hudkins et al., 1992) with some modifications. In brief, guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

Each assay tube contained 10 μL of [$^3$H](+)-pentazocine (final concentration of 0.5 nM), 900 μL of the tissue suspension to a final assay volume of 1 mL and a final tissue concentration of approximately 30 mg tissue net weight/mL. Non-specific binding was defined by addition of a final concentration of 1 µM haloperidol. All tubes were incubated at 37° C. for 150 min before termination of the reaction by rapid filtration over Schleicher & Schuell GF 3362 glass fibre filters [previously soaked in a solution of 0.5% polyethylenimine for at least 1 h]. Filters were then washed with four times with 4 mL of cold Tris-HCl buffer (50 mM, pH 7.4). Following addition of scintillation cocktail, the samples were allowed to equilibrate overnight. The amount of bound radioactivity was determined by liquid scintillation spectrometry using a Wallac Winspectral 1414 liquid scintillation counter. Protein concentrations were determined by the method of Lowry et al. (1951).

Sigma-2

Binding studies for σ2-receptor are performed as described (Radesca et al., 1991) with some modifications. In brief, brains from sigma receptor type I (σ1) knockout mice are homogenized in a volume of 10 mL/g tissue net weight of ice-cold 10 mM Tris-HCl, pH 7.4, containing 320 mM sucrose (Tris-sucrose buffer) with a Potter-Elvehjem homogenizer (10 strokes at 500 r.p.m.) The homogenates are then centrifuged at 1000 g for 10 min at 4° C., and the supernatants are saved. The pellets are resuspended by vortexing in 2 mL/g ice-cold Tris-sucrose buffer and centrifuged again at 1000 g for 10 min. The combined 1000 g supernatants are centrifuged at 31000 g for 15 min at 4° C. The pellets are resuspended by vortexing in 3 mL/g 10 mM Tris-HCl, pH 7.4, and the suspension is kept at 25° C. for 15 min. Following centrifugation at 31000 g for 15 min, the pellets are resuspended by gentle Potter Elvehjem homogenization to a volume of 1.53 mL/g in 10 mM Tris-HCl pH 7.4.

The assay tubes contain 10 µL of [$^3$H]-DTG (final concentration of 3 nM), 400 µL of the tissue suspension (5.3 mL/g in 50 mM Tris-HCl, pH 8.0) to a final assay volume of 0.5 mL. Non-specific binding is defined by addition of a final concentration of 1 µM haloperidol. All tubes are incubated at 25° C. for 120 min before termination of the reaction by rapid filtration over Schleicher & Schuell GF 3362 glass fibre filters [previously soaked in a solution of 0.5% polyethylenimine for at least 1 h]. Filters are washed with three times with 5 mL volumes of cold Tris-HCl buffer (10 mM, pH 8.0). Following addition of scintillation cocktail samples are allowed to equilibrate overnight. The amount of bound radioactivity is determined by liquid scintillation spectrometry using a Wallac Winspectral 1414 liquid scintillation counter. Protein concentrations are determined by the method of Lowry et al. (1951).

REFERENCES

DeHaven-Hudkins, D. L., L. C. Fleissner, and F. Y. Ford-Rice, 1992, "Characterization of the binding of [$^3$H](+)pentazocine to a recognition sites in guinea pig brain", Eur. J. Pharmacol. 227, 371-378.

Radesca, L., W. D. Bowen, and L. Di Paolo, B. R. de Costa, 1991, Synthesis and Receptor Binding of Enantiomeric N-Substituted cis-N-[2-(3,4-Dichlorophenyl)ethyl]-2-(1-pyrrolidinyl)cyclohexylamines as High-Affinity a Receptor Ligands, J. Med. Chem. 34, 3065-3074.

Langa, F., Codony X., Tovar V., Lavado A., Giménez E., Cozar P., Cantero M., Dordal A., Hernandez E., Pérez R., Monroy X., Zamanillo D., Guitart X., Montoliu L. I., 2003, Generation and phenotypic analysis of sigma receptor type I (Sigma1) knockout mice, European Journal of Neuroscience, Vol. 18, 2188-2196.

Lowry, O. H., N. J. Rosebrough, A. L. Farr, and R. J. Randall, 1951, Protein measurement with the Folin phenol reagent, J. Biol. Chem., 193, 265.

Some of the results obtained for the Sigma-1 receptor are shown in table (I).

TABLE I

| Example | % Binding σ1 $10^{-7}$ M | % Binding σ1 $10^{-8}$ M |
|---------|--------------------------|--------------------------|
| 11 | 70.9 | 18.2 |
| 3 | 70.6 | 27.3 |
| 5 | 84.5 | 32.8 |
| 7 | 89.3 | 48.6 |
| 9 | 23 | 5 |

The invention claimed is:

1. A method of treating a sigma receptor mediated disease or condition, wherein said disease or condition is pain, said method comprising administering to a patient in need of such a treatment a therapeutically effective amount of a compound of formula (I),

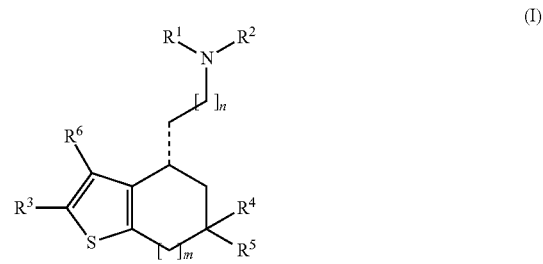

wherein
n is 1;
m is 1;
the dotted line ------ represents either a single or a double bond;
$R^1$ represents a hydrogen atom; $S(O)_2$—$R_{11}$; $C(O)$—$R_{11}$; a linear or branched, saturated or unsaturated, optionally at least mono-substituted aliphatic radical; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

$R^2$ represents $S(O)_2—R_{11}$; $C(O)—R_{11}$; a linear or branched, saturated or unsaturated, optionally at least mono-substituted aliphatic radical, with the substituents selected from OH, SH, $NH_2$, F, Cl, Br, I; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or $R^1$ and $R^2$ form together with the bridging nitrogen atom an optionally at least mono-substituted heterocyclyl group selected from:

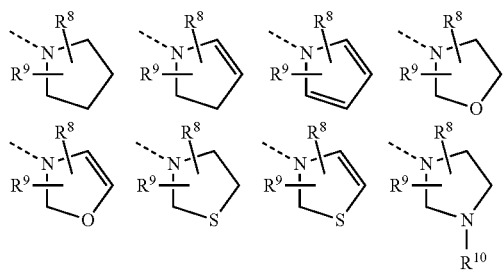

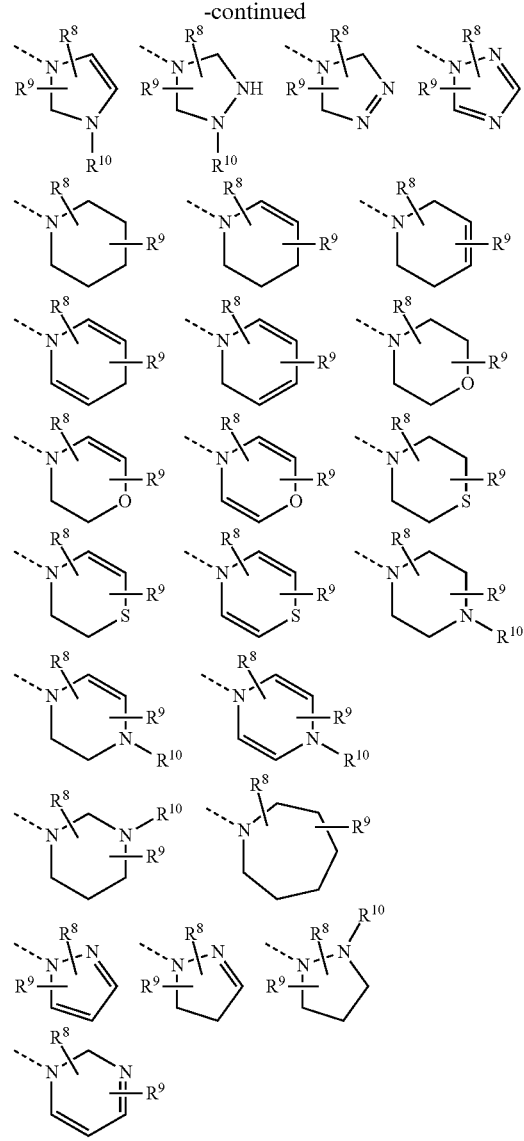

which is optionally condensed with an optionally at least mono-substituted mono- or polycyclic ring system; or which is optionally bound through a spirocyclic binding to an optionally at least mono-substituted mono- or polycyclic ring system;

$R^3$ represents a hydrogen atom;

$R^4$ and $R^5$, represent a hydrogen atom;

$R^6$ represents a hydrogen atom;

$R^7$ represents a hydrogen atom; a linear or branched, optionally at least mono-substituted aliphatic radical;

$R^8$ and $R^9$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^8$ and $R^9$, binding to the same C-atom in the ring, form together with this C-atom in the ring an optionally at least mono-substituted mono- or polycyclic ring system; or $R^8$ and $R^9$, binding to different adjacent ring members; form together with these ring members an optionally at least mono-substituted mono- or polycyclic ring system; or $R^{10}$ represents hydrogen; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group; wherein $R^{10}$ cannot be methoxyphenyl;

$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group with the provisos that
if n is 1
$R^1$ and $R^2$ may not form, together with their bridging nitrogen atom, an imidazole group;
if m is 1, n is 1 and the dotted line ------ represents a double bond,
$R^1$ and $R^2$ may not form, together with their bridging nitrogen atom, 5-Etoxy-2-Pyrrolidinone or 2,5-pyrrolidinedione;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

2. The method according to claim 1, wherein the compound of formula I comprises:

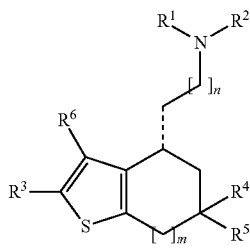

wherein
n is 1;
m is 1;
the dotted line ------ represents either a single or a double bond;

$R^1$ represents a hydrogen atom; a linear or branched, saturated or unsaturated, optionally at least mono-substituted aliphatic radical;

$R^2$ represents a linear or branched, saturated or unsaturated, optionally at least mono-substituted aliphatic radical, with the substituents selected from OH, SH, $NH_2$, F, Cl, Br, I; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or $R^1$ and $R^2$ form together with the bridging nitrogen atom an optionally at least mono-substituted heterocyclyl group selected from:

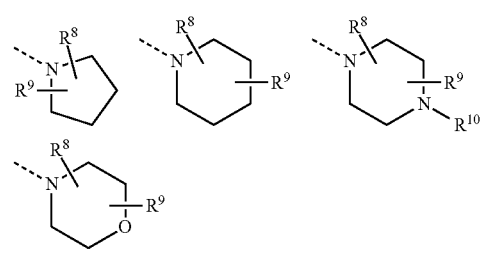

$R^3$ represents a hydrogen atom;
$R^4$ and $R^5$ represent a hydrogen atom;
$R^6$ represents a hydrogen atom;
$R^7$ represents a hydrogen atom; a linear or branched, optionally at least mono-substituted aliphatic radical;
$R^8$ and $R^9$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members; form together with these ring members an optionally at least mono-substituted mono- or polycyclic ring system;

$R^{10}$ represents hydrogen; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group; wherein $R^{10}$ cannot be methoxyphenyl;

if m is 1, n is 1 and the dotted line ------ represents a double bond, $R^1$ and $R^2$ may not form, together with their bridging nitrogen atom, 5-Etoxy-2-Pyrrolidinone or 2,5-pyrrolidinedione;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

3. The method according to claim 1, wherein the compound of formula (I) is characterized in that n is 1;

m is 1;

the dotted line ------ represents either a single or a double bond;

$R^1$ represents a hydrogen atom; a linear or branched, saturated or unsaturated, optionally at least mono-substituted aliphatic radical;

$R^2$ represents a linear or branched, saturated or unsaturated, optionally at least mono-substituted aliphatic radical, with the substituents selected from OH, SH, $NH_2$, F, Cl, Br, I; an optionally at least mono-substituted cycloalkyl group which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted aryl radical which is optionally condensed to other, at least mono-substituted, mono- or polycyclic ring systems, or may be optionally bound through a spirocyclic binding to an optionally at least mono-substituted mono- or polycyclic ring system; an optionally at least mono-substituted heterocyclyl group which is optionally condensed to other, at least mono-substituted, mono- or polycyclic ring systems, or may be optionally bound through a spirocyclic binding to an optionally at least mono-substituted mono- or polycyclic ring system; a linear or branched, optionally at least mono-substituted alkyl-cycloalkyl group in which the cycloalkyl group may be optionally at least mono-substituted and/or condensed with a mono- or polycyclic ring system, or may be optionally bound through a spirocyclic binding to an optionally at least mono-substituted mono- or polycyclic ring system; a linear or branched optionally at least mono-substituted alkyl-aryl group in which the aryl group may be optionally at least mono-substituted and/or condensed with a mono- or polycyclic ring system, or may be optionally bound through a spirocyclic binding to an optionally at least mono-substituted mono- or polycyclic ring system; a linear or branched, optionally at least mono-substituted alkyl-heterocyclyl group in which the heterocyclyl group may be optionally at least mono-substituted and/or condensed with a mono- or polycyclic ring system, or may be optionally bound through a spirocyclic binding to an optionally at least mono-substituted mono- or polycyclic ring system;

or $R^1$ and $R^2$ form together with the bridging nitrogen atom an optionally at least mono-substituted heterocyclyl group selected from:

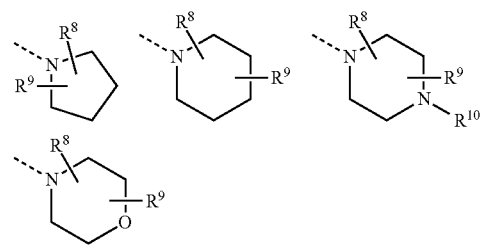

$R^3$ represents a hydrogen atom;

$R^6$ represents a hydrogen atom;

$R^4$ and $R^5$ represent a hydrogen atom;

$R^7$ represents H, $CF_3$, $CH_3$ or $C_2H_5$;

$R^{10}$ represents H, $CF_3$, $CH_3$ or $C_2H_5$; an optionally at least mono-substituted phenyl or naphthyl radical; an optionally at least mono-substituted heterocyclyl group; an optionally at least mono-substituted —$CH_2$-phenyl, —$CH_2$-naphthyl —$CH_2$—$CH_2$-phenyl or —$CH_2$—$CH_2$-naphthyl; an optionally at least mono-substituted —$CH_2$-heterocyclyl group or —$CH_2$—$CH_2$-heterocyclyl group;

$R^8$ and $R^9$, identical or different, represent H; OH; an optionally at least mono-substituted phenyl or naphthyl radical; an optionally at least mono-substituted heterocyclyl group; an optionally at least mono-substituted —$CH_2$-phenyl, —$CH_2$-naphthyl, —$CH_2$—$CH_2$-phenyl or —$CH_2$—$CH_2$-naphthyl; an optionally at least mono-substituted —$CH_2$-heterocyclyl group or —$CH_2$—$CH_2$-heterocyclyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members, form together with these ring members an optionally at least mono-substituted mono- or polycyclic ring system.

4. The method according to claim 1, wherein the compound of formula (I) comprises a compound of formula (IA):

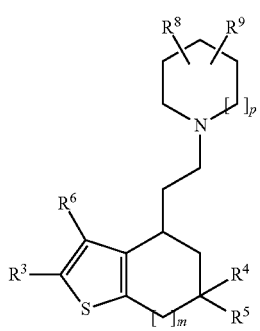

(IA)

wherein
m is 1;
p is selected from 0 or 1;
$R^3$ represents a hydrogen atom;
$R^4$ and $R^5$ represent a hydrogen atom;
$R^6$ represents a hydrogen atom;
$R^7$ represents a hydrogen atom; a linear or branched, optionally at least mono-substituted aliphatic radical;
$R^8$ and $R^9$, identical or different, represent a hydrogen atom; a halogen; $OR^7$; a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members; form together with these ring members an optionally at least mono-substituted mono- or polycyclic ring system;

$R^{11}$ represents a linear or branched, saturated or unsaturated, optionally at least mono-substituted aliphatic radical; an optionally at least mono-substituted cycloalkyl group; an optionally at least mono-substituted aryl radical; an optionally at least mono-substituted heterocyclyl group; a linear or branched, optionally at least mono-substituted alkyl-aryl group; a linear or branched, optionally at least mono-substituted alkyl-heterocyclyl group; a linear or branched, optionally at least mono-substituted alkyl-cycloalkyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

5. The method according to claim 4, wherein the compound of formula (IA) is characterized in that
m is 1;
p is selected from 0 or 1;
$R^3$ represents a hydrogen atom;
$R^6$ represents a hydrogen atom;
$R^4$ and $R^5$ represent a hydrogen atom;
$R^7$ represents H, $CF_3$, $CH_3$ or $C_2H_5$;

$R^8$ and $R^9$, identical or different, represent H; OH; an optionally at least mono-substituted phenyl or naphthyl radical; an optionally at least mono-substituted heterocyclyl group; an optionally at least mono-substituted $-CH_2$-phenyl, $-CH_2$-naphthyl, $-CH_2-CH_2$-phenyl or $-CH_2-CH_2$-naphthyl; an optionally at least mono-substituted $-CH_2$-heterocyclyl group or $-CH_2-CH_2$-heterocyclyl group;

or $R^8$ and $R^9$, binding to the same C-atom in the ring, form together with this C-atom in the ring an optionally at least mono-substituted mono- or polycyclic ring system;

or $R^8$ and $R^9$, binding to different adjacent ring members, form together with these ring members an optionally at least mono-substituted mono- or polycyclic ring system.

6. The method according to claim 4, wherein the compound of formula (IA) is characterized in that $R^8$ represents H or OH;

$R^9$ represents H; $CH_3$; an optionally at least mono-substituted phenyl; an optionally at least mono-substituted naphthyl radical; an optionally at least mono-substituted heterocyclyl group;

preferably $R^8$ represents H or OH;

$R^9$ represents H, $CH_3$, an unsubstituted phenyl; a phenyl substituted by $C(O)CH_3$, COOH, $CH_3$, $OCH_3$, $CF_3$, Cl, F, $NH_2$, $C(O)-O-CH_3$, halogen (especially Cl or F); an unsubstituted naphthyl; an optionally at least mono-substituted heterocyclyl group, selected from:

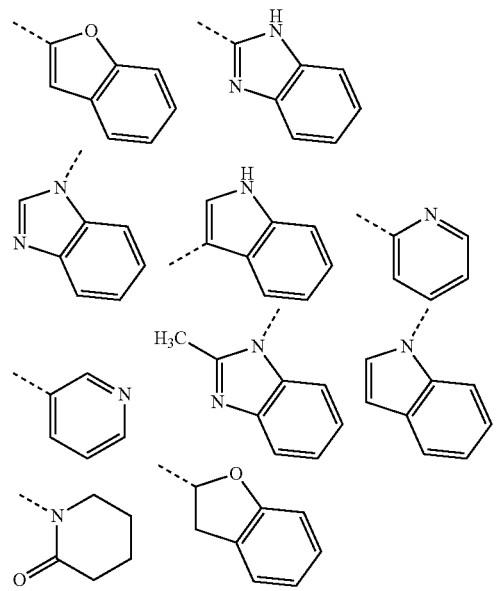

most preferably $R^8$ represents H or OH;

$R^9$ represents H or $CH_3$, an unsubstituted phenyl; a phenyl substituted by $C(O)CH_3$, COOH, $CH_3$, $OCH_3$, $CF_3$, Cl, F, $NH_2$, $C(O)-O-CH_3$, halogen (especially Cl or F); an unsubstituted naphthyl; an optionally at least mono-substituted heterocyclyl group, selected from:

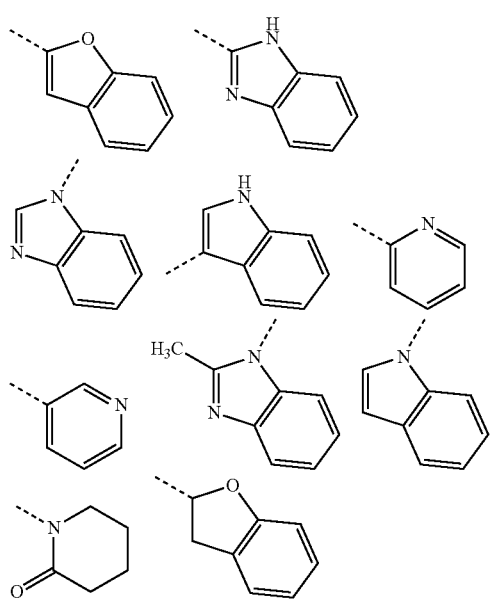

with R⁸ being a substitute in the ortho, meta or para position if p is 1 or in 2- or 3-position if p is 0.

7. The method according to claim 4, wherein the compound of formula (IA) is characterized in that R⁸ and R⁹, binding to the same C-atom in the ring, form together with this C-atom in the ring an optionally at least mono-substituted mono- or polycyclic ring system, preferably leading together with the substituted heterocycle according to formula 1B to spirocyclic structures selected from:

A (if p is 1)

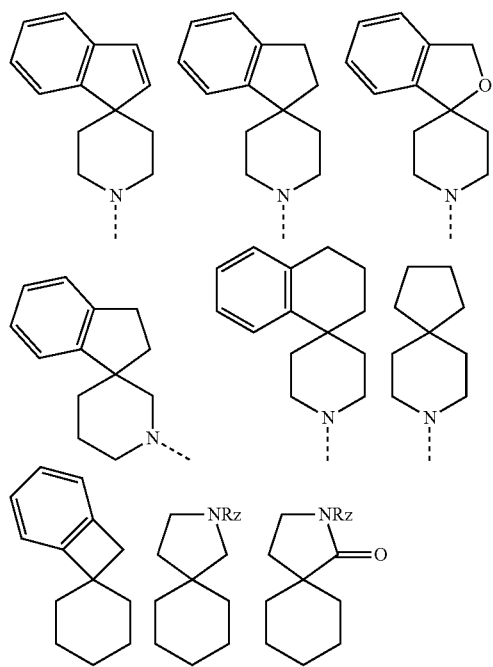

or B if p is 0

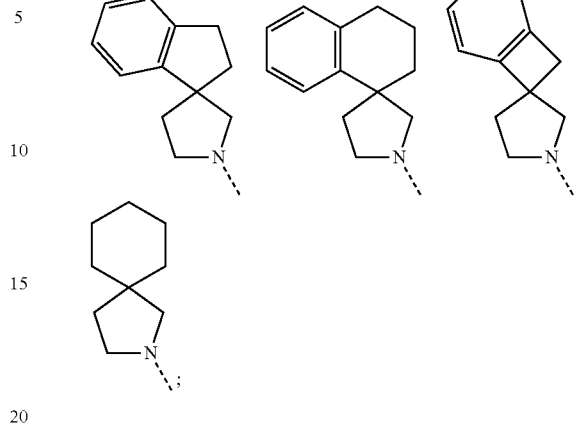

optionally at least mono-substituted, with Rz being preferably a substituted phenyl, an unsubstituted phenyl, a benzyl or an alkyl.

8. The method according to claim 4, wherein the compound of formula (IA) is characterized in that R⁸ and R⁹, binding to different adjacent ring C-Atoms, form together with these C-atom in the ring an optionally at least mono-substituted mono- or polycyclic ring system, preferably leading together with the substituted heterocycle to the following structures (if p is 1 or 0):

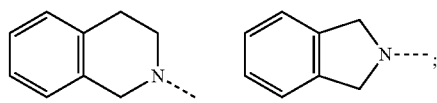

optionally at least mono-substituted, most preferably on the aromatic ring.

9. The method according to claim 2, wherein the compound of formula (I) is selected from the group consisting of:
4-phenyl-1-(2-(4,5,6,7-tetrahydrobenzo[b]thiophen-4-yl) ethyl)piperidine,
4-phenyl-1-(2-(4,5,6,7-tetrahydrobenzo[b]thien-4-yl) ethyl)piperidine oxalate,
(E)-N-benzyl-2-(6,7-dihydrobenzo[b]thien-4(5H)-ylidene)-N-methylethanamine,
(E)-N-benzyl-2-(6,7-dihydrobenzo[b]thien-4(5H)-ylidene)-N-methylethanamine oxalate,
(E)-1-(2-(6,7-dihydrobenzo[b]thien-4(5H)-ylidene) ethyl)-4-phenylpiperidine,
(E)-1-(2-(6,7-dihydrobenzo[b]thien-4(5H)-ylidene) ethyl)-4-phenylpiperidine oxalate,
(E)-N-(2-(6,7-dihydrobenzo[b]thien-4(5H)-ylidene) ethyl)-N-methyl-2-phenylethanamine,
(E)-N-(2-(6,7-dihydrobenzo[b]thien-4(5H)-ylidene) ethyl)-N-methyl-2-phenylethanamine oxalate,
(E)-1-(2-(6,7-dihydrobenzo[b]thien-4(5H)-ylidene)ethyl) piperidine,
(E)-1-(2-(6,7-dihydrobenzo[b]thien-4(5H)-ylidene)ethyl) piperidine oxalate,
(E)-1-(2-(6,7-dihydrobenzo[b]thien-4(5H)-ylidene) ethyl)-4-methylpiperidine,
(E)-1-(2-(6,7-dihydrobenzo[b]thien-4(5H)-ylidene) ethyl)-4-methylpiperidine oxalate, (E)-4-(2-(6,7-dihydrobenzo[b]thien-4(5H)-ylidene)ethyl) morpholine,
(E)-4-(2-(6,7-dihydrobenzo[b]thien-4(5H)-ylidene)ethyl) morpholine oxalate,
4-(2-[spiro[isobenzofuran-1(3H),4'-piperidin]-1'-yl]-ethyl)-4,5,6,7-tetrahydrobenzo[b]thiophene,
4-(2-[spiro[isobenzofuran-1 (3H),4'-piperidin]-1'-yl]-ethyl)-4,5,6,7-tetrahydrobenzo[b]thiophene oxalate,
4-phenyl-1-(2-(4,5,6,7-tetrahydrobenzo[b]thien-4-yl) ethyl)piperidin-4-ol,
4-phenyl-1-(2-(4,5,6,7-tetrahydrobenzo[b]thien-4-yl) ethyl)piperidin-4-ol oxalate,
4-(4-chlorophenyl)-1-(2-(4,5,6,7-tetrahydrobenzo[b] thien-4-yl)ethyl)piperidin-4-ol,
4-(4-chlorophenyl)-1-(2-(4,5,6,7-tetrahydrobenzo[b] thien-4-yl)ethyl)piperidin-4-ol oxalate,
2-(2-(4,5,6,7-tetrahydrobenzo[b]thien-4-yl)ethyl)isoindoline,
2-(2-(4,5,6,7-tetrahydrobenzo[b]thien-4-yl)ethyl)isoindoline oxalate,
N-benzyl-N-methyl-2-(4,5,6,7-tetrahydrobenzo[b]thien-4-yl)ethanamine,
N-benzyl-N-methyl-2-(4,5,6,7-tetrahydrobenzo[b]thien-4-yl)ethanamine oxalate,
1-(2-(4,5,6,7-tetrahydrobenzo[b]thiophen-4-yl)ethyl)-4-(4-(trifluoromethyl)phenyl)piperidine,
1-(2-(4,5,6,7-tetrahydrobenzo[b]thiophen-4-yl)ethyl)-4-(4-(trifluoromethyl)phenyl)piperidine oxalate,
1-(2-(4,5,6,7-tetrahydrobenzo[b]thiophen-4-yl)ethyl)-4-o-tolylpiperidine,
1-(2-(4,5,6,7-tetrahydrobenzo[b]thiophen-4-yl)ethyl)-4-o-tolylpiperidine oxalate,
4-(3-fluorophenyl)-1-(2-(4,5,6,7-tetrahydrobenzo[b] thiophen-4-yl)ethyl)piperidine,
4-(3-fluorophenyl)-1-(2-(4,5,6,7-tetrahydrobenzo[b] thiophen-4-yl)ethyl)piperidine oxalate,
4-(naphthalen-1-yl)-1-(2-(4,5,6,7-tetrahydrobenzo[b] thiophen-4-yl)ethyl)piperidine,
4-(naphthalen-1-yl)-1-(2-(4,5,6,7-tetrahydrobenzo[b] thiophen-4-yl)ethyl)piperidine oxalate,
4-(4-chlorophenyl)-1-(2-(4,5,6,7-tetrahydrobenzo[b] thiophen-4-yl)ethyl)piperidine,
4-(4-chlorophenyl)-1-(2-(4,5,6,7-tetrahydrobenzo[b] thiophen-4-yl)ethyl)piperidine oxalate,
4-(2-methoxyphenyl)-1-(2-(4,5,6,7-tetrahydrobenzo[b] thiophen-4-yl)ethyl)piperidine,
4-(2-methoxyphenyl)-1-(2-(4,5,6,7-tetrahydrobenzo[b] thiophen-4-yl)ethyl)piperidine oxalate,
1-(2-(4,5,6,7-tetrahydrobenzo[b]thiophen-4-yl)ethyl)-4-p-tolylpiperidine,
1-(2-(4,5,6,7-tetrahydrobenzo[b]thiophen-4-yl)ethyl)-4-p-tolylpiperidine oxalate,
4-(2-(2,3-dihydrospiro[1H-indene-1,4'-piperidin]-1'-yl) ethyl)-4,5,6,7-tetrahydrobenzo[b]thiophene,
4-(2-(2,3-dihydrospiro[1H-indene-1,4'-piperidin]-1'-yl) ethyl)-4,5,6,7-tetrahydrobenzo[b]thiophene oxalate,
4-(3-chlorophenyl)-1-(2-(4,5,6,7-tetrahydrobenzo[b] thiophen-4-yl)ethyl)piperidine,
4-(3-chlorophenyl)-1-(2-(4,5,6,7-tetrahydrobenzo[b] thiophen-4-yl)ethyl)piperidine oxalate,
4-(3-methoxyphenyl)-1-(2-(4,5,6,7-tetrahydrobenzo[b] thiophen-4-yl)ethyl)piperidine,
4-(3-methoxyphenyl)-1-(2-(4,5,6,7-tetrahydrobenzo[b] thiophen-4-yl)ethyl)piperidine oxalate,
4-(4-fluorophenyl)-1-(2-(4,5,6,7-tetrahydrobenzo[b] thiophen-4-yl)ethyl)piperidine,
4-(4-fluorophenyl)-1-(2-(4,5,6,7-tetrahydrobenzo[b] thiophen-4-yl)ethyl)piperidine oxalate,
4-(3,5-bis(trifluoromethyl)phenyl)-1-(2-(4,5,6,7-tetrahydrobenzo[b]thiophen-4-yl)ethyl)piperidine,
4-(3,5-bis(trifluoromethyl)phenyl)-1-(2-(4,5,6,7-tetrahydrobenzo[b]thiophen-4-yl)ethyl)piperidine oxalate,
4-(naphthalen-2-yl)-1-(2-(4,5,6,7-tetrahydrobenzo[b] thiophen-4-yl)ethyl)piperidine,
4-(naphthalen-2-yl)-1-(2-(4,5,6,7-tetrahydrobenzo[b] thiophen-4-yl)ethyl)piperidine oxalate,
4-(benzofuran-2-yl)-1-(2-(4,5,6,7-tetrahydrobenzo[b] thiophen-4-yl)ethyl)piperidine,
4-(benzofuran-2-yl)-1-(2-(4,5,6,7-tetrahydrobenzo[b] thiophen-4-yl)ethyl)piperidine oxalate,
4-(2-fluorophenyl)-1-(2-(4,5,6,7-tetrahydrobenzo[b] thiophen-4-yl)ethyl)piperidine,
4-(2-fluorophenyl)-1-(2-(4,5,6,7-tetrahydrobenzo[b] thiophen-4-yl)ethyl)piperidine oxalate,
2-phenyl-1-(2-(4,5,6,7-tetrahydrobenzo[b]thiophen-4-yl) ethyl)piperidine,
4-(benzo[b]thiophen-3-yl)-1-(2-(4,5,6,7-tetrahydrobenzo [b]thiophen-4-yl)ethyl)piperidine,
4-(benzo[b]thiophen-3-yl)-1-(2-(4,5,6,7-tetrahydrobenzo [b]thiophen-4-yl)ethyl)piperidine oxalate,
2-(1-(2-(4,5,6,7-tetrahydrobenzo[b]thiophen-4-yl)ethyl) piperidin-4-yl)-1H-benzo[d]imidazole,
2-(1-(2-(4,5,6,7-tetrahydrobenzo[b]thiophen-4-yl)ethyl) piperidin-4-yl)-1H-benzo[d]imidazole oxalate,
2-methyl-1-(1-(2-(4,5,6,7-tetrahydrobenzo[b]thiophen-4-yl)ethyl)piperidin-4-yl)-1H-benzo[d]imidazole,
2-methyl-1-(1-(2-(4,5,6,7-tetrahydrobenzo[b]thiophen-4-yl)ethyl)piperidin-4-yl)-1H-benzo[d]imidazole oxalate,
4-(4-methoxyphenyl)-1-(2-(4,5,6,7-tetrahydrobenzo[b] thiophen-4-yl)ethyl)piperidine,
4-(4-methoxyphenyl)-1-(2-(4,5,6,7-tetrahydrobenzo[b] thiophen-4-yl)ethyl)piperidine oxalate,
2-Methyl-8-[2-(4,5,6,7-tetrahydrobenzo[b]thiophen-4-yl)-ethyl]-2,8-diazaspiro[4.5]decan-1-one,
2-Methyl-8-[2-(4,5,6,7-tetrahydrobenzo[b]thiophen-4-yl)-ethyl]-2,8-diazaspiro[4.5]decan-1-one oxalate,
1'-(2-(4,5,6,7-tetrahydrobenzo[b]thiophen-4-yl)ethyl)-spiro(isobenzofuran-1(3H), 4'-piperidin)-3-one,
1'-(2-(4,5,6,7-tetrahydrobenzo[b]thiophen-4-yl)ethyl)-spiro(isobenzofuran-1(3H), 4'-piperidin)-3-one oxalate,
2-(4-Chlorophenyl)-8-[2-(4,5,6,7-tetrahydrobenzo[b] thiophen-4-yl)-ethyl]-2,8-diazaspiro[4.5]decan-1-one,
2-(4-Chlorophenyl)-8-[2-(4,5,6,7-tetrahydrobenzo[b] thiophen-4-yl)-ethyl]-2,8-diazaspiro[4.5]decan-1-one oxalate,
8-[2-(4,5,6,7-Tetrahydrobenzo[b]thiophen-4-yl)-ethyl]-2,8-diazaspiro[4.5]decan-1-one,
8-[2-(4,5,6,7-Tetrahydrobenzo[b]thiophen-4-yl)-ethyl]-2,8-diazaspiro[4.5]decan-1-one oxalate,
4-(2-(spiro[1H-indene-1,4'-piperidin]-1'-yl)ethyl)-4,5,6,7-tetrahydrobenzo[b]thiophene,
4-(2-(spiro[1H-indene-1,4'-piperidin]-1'-yl)ethyl)-4,5,6,7-tetrahydrobenzo[b]thiophene oxalate,
7-methoxy-2-(2-(4,5,6,7-tetrahydrobenzo[b]thiophen-4-yl)ethyl)-1,2,3,4-tetrahydroisoquinoline,
7-methoxy-2-(2-(4,5,6,7-tetrahydrobenzo[b]thiophen-4-yl)ethyl)-1,2,3,4-tetrahydroisoquinoline oxalate,
5,7-dichloro-2-(2-(4,5,6,7-tetrahydrobenzo[b]thiophen-4-yl)ethyl)-1,2,3,4-tetrahydroisoquinoline,
5,7-dichloro-2-(2-(4,5,6,7-tetrahydrobenzo[b]thiophen-4-yl)ethyl)-1,2,3,4-tetrahydroisoquinoline oxalate,
1-(1-(2-(4,5,6,7-tetrahydrobenzo[b]thiophen-4-yl)ethyl) piperidin-4-yl)-1H-indole, 1-(1-(2-(4,5,6,7-tetrahydrobenzo[b]thiophen-4-yl)ethyl) piperidin-4-yl)-1H-indole oxalate, 2-tert-butyl-8-[2-(4,5,6,7-tetrahydrobenzo[b]thiophen-4-yl)-ethyl]-2,8-diazaspiro[4.5]decan-1-one, 2-tert-butyl-8-[2-(4,5,6,7-tetrahydrobenzo[b]thiophen-4-yl)-ethyl]-2,8-diazaspiro[4.5]decan-1-one oxalate, 2-benzyl-8-[2-(4,5,6,7-tetrahydrobenzo[b]thiophen-4-yl)-ethyl]-2,8-diazaspiro[4.5]decan-1-one, 2-benzyl-8-[2-(4,5,6,7-tetrahydrobenzo[b]thiophen-4-yl)-ethyl]-2,8-diazaspiro[4.5]decan-1-one oxalate, 2-(4-Methoxyphenyl)-8-[2-(4,5,6,7-tetrahydrobenzo[b] thiophen-4-yl)-ethyl]-2,8-diazaspiro[4.5]decan-1-one, 2-(4-Methoxyphenyl)-8-[2-(4,5,6,7-tetrahydrobenzo[b] thiophen-4-yl)-ethyl]-2,8-diazaspiro[4.5]decan-1-one oxalate, 2-phenyl-8-[2-(4,5,6,7-tetrahydrobenzo[b]thiophen-4-yl)-ethyl]-2,8-diazaspiro[4.5]decan-1-one, 2-phenyl-8-[2-(4,5,6,7-tetrahydrobenzo[b]thiophen-4-yl)-ethyl]-2,8-diazaspiro[4.5]decan-1-one oxalate, 2-(4-trifluoromethylphenyl)-8-[2-(4,5,6,7-tetrahydrobenzo[b]thiophen-4-yl)-ethyl]-2,8-diazaspiro[4.5]decan-1-one, 2-(4-trifluoromethylphenyl)-8-[2-(4,5,6,7-tetrahydrobenzo[b]thiophen-4-yl)-ethyl]-2,8-diazaspiro[4.5]decan-1-one oxalate, 5-bromo-2-(2-(4,5,6,7-tetrahydrobenzo[b]thiophen-4-yl)ethyl)-1,2,3,4-tetrahydroisoquinoline, 5-bromo-2-(2-(4,5,6,7-tetrahydrobenzo[b]thiophen-4-yl)ethyl)-1,2,3,4-tetrahydroisoquinoline oxalate, 2-(2-(4,5,6,7-tetrahydrobenzo[b]thiophen-4-yl)ethyl)-1,2,3,4-tetrahydroisoquinoline-7-carbonitrile, 2-(2-(4,5,6,7-tetrahydrobenzo[b]thiophen-4-yl)ethyl)-1,2,3,4-tetrahydroisoquinoline-7-carbonitrile oxalate, 2-(4-Fluorophenyl)-8-[2-(4,5,6,7-tetrahydrobenzo[b] thiophen-4-yl)-ethyl]-2,8-diazaspiro[4.5]decan-1-one, and 2-(4-Fluorophenyl)-8-[2-(4,5,6,7-tetrahydrobenzo[b] thiophen-4-yl)-ethyl]-2,8-diazaspiro[4.5]decan-1-one oxalate;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

10. The method according to claim 1, wherein the compound of formula (I) is provided as a pharmaceutical composition which comprises a compound of formula (I) or a pharmaceutically acceptable salt thereof, and a pharmaceutically acceptable carrier, adjuvant or vehicle.

11. The method according to claim 1, wherein the pain is neuropathic pain, inflammatory pain or other pain conditions, allodynia and/or hyperalgesia, especially mechanical allodynia.

* * * * *